(12) United States Patent
Lockwood et al.

(10) Patent No.: US 7,691,901 B2
(45) Date of Patent: Apr. 6, 2010

(54) CAROTENOID ANALOGS OR DERIVATIVES FOR THE INHIBITION AND AMELIORATION OF INFLAMMATION

(75) Inventors: Samuel Fournier Lockwood, Lago Vista, TX (US); Sean O'Malley, Honolulu, HI (US); Henry Jackson, Honolulu, HI (US); Geoff Nadolski, Kaneohe, HI (US)

(73) Assignee: Cardax Pharmaceuticals Inc., Aiea, HI (US)

( * ) Notice: Subject to any disclaimer, the term of this patent is extended or adjusted under 35 U.S.C. 154(b) by 36 days.

(21) Appl. No.: 11/106,378

(22) Filed: Apr. 14, 2005

(65) Prior Publication Data

US 2005/0261254 A1 Nov. 24, 2005

Related U.S. Application Data

(60) Provisional application No. 60/562,195, filed on Apr. 14, 2004.

(51) Int. Cl.
*A61K 31/341* (2006.01)
*A61K 31/351* (2006.01)

(52) U.S. Cl. ...................... 514/460; 514/473

(58) Field of Classification Search ............ 514/460, 514/473
See application file for complete search history.

(56) References Cited

U.S. PATENT DOCUMENTS

| | | | |
|---|---|---|---|
| 3,354,218 A | 11/1967 | Surmatis |
| 3,755,422 A | 8/1973 | Morel |
| 3,965,261 A | 6/1976 | Gainer |
| 3,975,519 A | 8/1976 | Gainer |
| 3,989,757 A | 11/1976 | Surmatis |
| 4,009,270 A | 2/1977 | Gainer |
| 4,038,144 A | 7/1977 | Gainer |
| 4,046,880 A | 9/1977 | Gainer |
| 4,070,460 A | 1/1978 | Gainer |
| 4,176,179 A | 11/1979 | Gainer |
| 4,304,784 A | 12/1981 | Fujimura et al. |
| 4,435,427 A | 3/1984 | Hoppe et al. |
| 4,491,574 A | 1/1985 | Seifter et al. |
| 5,057,494 A | 10/1991 | Sheffield |
| 5,153,001 A | 10/1992 | Ismail |
| 5,221,668 A | 6/1993 | Henningfield et al. |
| 5,278,189 A | 1/1994 | Rath et al. |
| 5,310,554 A | 5/1994 | Haigh |
| 5,326,757 A | 7/1994 | Demopoulos |
| 5,328,845 A | 7/1994 | Finkelstein et al. |
| 5,346,488 A | 9/1994 | Prince et al. |
| 5,364,563 A | 11/1994 | Cathrein et al. |
| 5,422,247 A | 6/1995 | Finkelstein et al. |
| 5,455,362 A | 10/1995 | Ernst et al. |
| 5,457,135 A | 10/1995 | Baranowitz et al. |
| 5,492,701 A | 2/1996 | Cervos et al. |
| 5,527,533 A | 6/1996 | Tso et al. |
| 5,536,504 A | 7/1996 | Eugster et al. |
| 5,589,468 A | 12/1996 | Lin et al. |
| 5,607,707 A | 3/1997 | Ford et al. |
| 5,607,839 A | 3/1997 | Tsubokura et al. |
| 5,612,485 A | 3/1997 | Schlipalius |
| 5,643,943 A | 7/1997 | Gamache et al. |
| 5,668,183 A | 9/1997 | Leuenberger |
| 5,705,180 A | 1/1998 | Schlipalius |
| 5,744,502 A | 4/1998 | Lignell et al. |
| 5,773,026 A | 6/1998 | Schlipalius |
| 5,801,159 A | 9/1998 | Miller et al. |

(Continued)

FOREIGN PATENT DOCUMENTS

EP 204987 12/1986

(Continued)

OTHER PUBLICATIONS

Buchwald, M. and W.P. Jencks. "Optical properties of astaxanthin solutions and aggregates." *Biochemistry* 1968, 7: 834-843.
Reznikoff et al "Quantitative and Qualitative Studies of Chemical Transformation of Cloned C3H Mouse Embryo Cells Sensitive to Postconfluence Inhibition of Cell Division." *Cancer Research*, 1973, 33:2339-2349.
Andrewes et al. "Animal carotenoids. 9. On the absolute configuration of astaxanthin and actinioerythrin." *Acta Chem. Scand.* 1974, B28:730-736.

(Continued)

*Primary Examiner*—Taofiq A Solola
(74) *Attorney, Agent, or Firm*—Meyertons, Hood, Kivlin, Kowert & Goetzel, P.C.; Eric B. Meyertons

(57) ABSTRACT

A method for inhibiting and/or ameliorating the occurrence of diseases in a human subject whereby a subject is administered a carotenoid analog or derivative, either alone or in combination with another carotenoid analog or derivative. In some embodiments, the administration of analogs or derivatives of carotenoids may inhibit and/or ameliorate the occurrence of diseases in subjects. In some embodiments, analogs or derivatives of carotenoids may be water-soluble and/or water dispersible. Maladies that may be treated with analogs or derivatives of carotenoids embodied herein may include diseases that provoke or trigger an inflammatory response. In an embodiment, asthma may be treated with analogs or derivatives of carotenoids embodied herein. In an embodiment, administering analogs or derivatives of carotenoids embodied herein to a subject may control or affect the bioavailability of eicosanoids. In an embodiment, atherosclerosis may be treated with analogs or derivatives of carotenoids embodied herein. In an embodiment, administering the analogs or derivatives of carotenoids embodied herein to a subject may control or affect the bioavailability of 5-LO-catalyzed eicosanoid metabolites. In an embodiment, 5-LO-catalyzed eicosanoid metabolites that may be controlled or affected by administering analogs or derivatives of carotenoids to a subject may include proinflammatory effector molecules (e.g., leukotrienes).

34 Claims, 7 Drawing Sheets

U.S. PATENT DOCUMENTS

| | | | |
|---|---|---|---|
| 5,811,446 | A | 9/1998 | Thomas |
| 5,837,224 | A | 11/1998 | Voorhees et al. |
| 5,849,345 | A | 12/1998 | Giger et al. |
| 5,854,015 | A | 12/1998 | Garnett et al. |
| 5,858,700 | A | 1/1999 | Ausich et al. |
| 5,863,953 | A | 1/1999 | Luddecke et al. |
| 5,871,766 | A | 2/1999 | Hennekens |
| 5,876,782 | A | 3/1999 | Sas et al. |
| 5,886,053 | A | 3/1999 | Schmutzler et al. |
| 5,891,907 | A | 4/1999 | Kolter et al. |
| 5,895,659 | A | 4/1999 | Luddecke et al. |
| 5,897,871 | A | 4/1999 | Schlipalius |
| 5,925,684 | A | 7/1999 | Schweikert et al. |
| 5,959,138 | A | 9/1999 | Torres-Cardona et al. |
| 5,968,251 | A | 10/1999 | Auweter et al. |
| 5,976,575 | A | 11/1999 | Gellenbeck |
| 6,020,003 | A | 2/2000 | Stroh et al. |
| 6,040,147 | A | 3/2000 | Ridker et al. |
| 6,043,259 | A | 3/2000 | Dhalla et al. |
| 6,046,181 | A | 4/2000 | Oonishi et al. |
| 6,051,587 | A | 4/2000 | Dakashinamurti et al. |
| 6,054,491 | A | 4/2000 | Lignell et al. |
| 6,060,511 | A | 5/2000 | Gainer |
| 6,075,058 | A | 6/2000 | Handelman |
| 6,083,520 | A | 7/2000 | Toneby |
| 6,093,348 | A | 7/2000 | Kowalski et al. |
| 6,132,790 | A | 10/2000 | Schlipalius |
| 6,218,436 | B1 | 4/2001 | Howard et al. |
| 6,232,060 | B1 | 5/2001 | Miller et al. |
| 6,245,818 | B1 | 6/2001 | Lignell |
| 6,258,855 | B1 | 7/2001 | Lorenz et al. |
| 6,265,450 | B1 | 7/2001 | Asami et al. |
| 6,313,169 | B1 | 11/2001 | Bowen et al. |
| 6,331,537 | B1 | 12/2001 | Hamilton et al. |
| 6,335,015 | B1 | 1/2002 | Lignell et al. |
| 6,344,214 | B1 | 2/2002 | Lorenz |
| 6,426,362 | B1 | 7/2002 | Miller et al. |
| 6,428,816 | B1 | 8/2002 | Schlipalius et al. |
| 6,540,654 | B2 | 4/2003 | Levy et al. |
| 6,579,544 | B1 | 6/2003 | Rosenberg et al. |
| 2002/0032176 | A1 | 3/2002 | Maoka et al. |
| 2002/0110604 | A1 | 8/2002 | Babish et al. |
| 2003/0035821 | A1 | 2/2003 | Heaton et al. |
| 2003/0180406 | A1 | 9/2003 | Sies |

FOREIGN PATENT DOCUMENTS

| | | |
|---|---|---|
| JP | 7300421 | 11/1995 |
| JP | 08073312 | 3/1996 |
| JP | 08337592 | 12/1996 |
| JP | 09084591 | 3/1997 |
| JP | 09202730 | 8/1997 |
| JP | 10155459 | 6/1998 |
| JP | 10327865 | 12/1998 |
| JP | 2001114673 | 4/2001 |
| WO | WO 90/10440 | 9/1990 |
| WO | WO 92/05780 | 4/1992 |
| WO | WO 98/37874 | 9/1998 |
| WO | WO 99/11251 | 3/1999 |
| WO | WO 99/30701 | 6/1999 |
| WO | WO 02/47680 | 6/2002 |
| WO | WO 02 068385 | 9/2002 |
| WO | WO 03 066583 | 8/2003 |

OTHER PUBLICATIONS

Salares et al. "Resonance Raman spectra of lobster shell carotenoproteins and a model astaxanthin aggregate. A possible photobiological function for the yellow protein." *Biochemistry* 1977, 16:4751-4756.

Salares et al. "Excited state (exciton) interactions in polyene aggregates". *J. Raman Spectr.* 1977, 6:282-288.

Halliwell, B. "Superoxide-dependent formation of hydroxyl radicals in the presence of iron chelates. Is it a mechanism for hydroxyl radical production in biological systems?" *FEBS Lett* 1978, 92:321-326.

Harada et al. "Circular dichroic power due to chiral exciton coupling between two polyacene chromophores." *J. Am. Chem. Soc.* 1978, 100:4029-4036.

Stuber et al. "A new synthesis of L-*threo*-hex-2-enaro-1,4-lactone ("saccharoascorbic" acid): a method for the protection of the enediol of ascorbic acid." *Carb. Res.* 1978, 60:251-258.

Bock et al. "Preparation of some bromodeoxyaldonic acids." *Carb. Res.* 1979, 68:313-319.

Merriman and Bertram "Reversible inhibition by retinoids of 3-methylcholanthrene- induced neoplastic transformation in C3H10T1/2 cells." *Cancer Research* 1979, 39:1661-1666.

Noack and Thomson "Conformation and optical-activity of all-*trans*, mono-*cis*, and di-*cis* carotenoids—temperature-dependent circular-dichroism." *Helv. Chim. Acta* 1979, 62: 1902-1921.

Müller et al. "Contribution to the analytical separation and the synthesis of 3-hydroxy-4-oxocarotenoids." *Helv. Chim. Acta* 1980, 63:1654-1664. (German; Abstract English Language).

Sturzenegger et al. "Classification of the CD spectra of carotenoids." *Helv. Chim. Acta* 1980, 63:1074-1092.

Bernhard et al. "Synthesis of optically-active natural carotenoids and structurally related-compounds. 9. Synthesis of (3R)-hydroxyechinenone, (3R,3'R)-adonixanthin and (3R,3'S)-adonixanthin, (3R)-adonirubin their optical antipodes and related-compounds." *Helv. Chim. Acta.* 1981, 64:2469-2484.(Summary English) Article German.

Noack and Thomson "Temperature and concentration dependent circular-dichroism of mono-*cis* and di-*cis* isomers of (3R,3'S)-astaxanthin diacetate." *Helv. Chim. Acta.* 1981, 64: 2383-2392.

Braunwald and Kloner "The stunned myocardium-prolonged post-ischemic ventricular dysfunction." *Circulation* 1982, 66:1146-1149.

Harada and Nakanishi "Circular Dichroic Spectroscopy—Exciton Coupling in Organic Stereochemistry", 1983, University Science Books, Mill Valley (CA).

Goodman "Mechanisms of disease: Vitamin A and retinoids in health and disease." *New England Journal Medicine* 1984, 310:1023-1031.

Bertram. "Neoplastic Transformation in Cell Cultures: In Vitro/In-Vivo Correlations." *IARC Sci.Pub.* 1985, 67:77-91.

Myers et al. "Enhancement of recovery of myocardial function by oxygen free radical scavengers after reversible myocardial ischemia." *Circulation* 1985, 72:915-921.

Ambrosio et al. "Reduction in experimental infarct size by recombinant human superoxide dismutase: insights into the pathophysiology of reperfusion injury." *Circulation* 1986, 74:1424-1433.

Blaustein et al. "Influence of exogenously generated oxidant species on myocardial function." *American Journal of Physiology* 1986, 250: H595-H599.

Gey, K. F. "On the antioxidant hypothesis with regard to atherosclerosis." *Biblthca Nutr. Dieta* 1986, 37:53-91.

Bolli et al.. "The iron chelator desferioxamine attenuates postischemic ventricular dysfunction." *American Journal of Physiology* 1987, 7253:H1372-H1380.

Bolli et al.. "Attenuation of dysfunction in the postischemic 'stunned' myocardium by dimethylurea." *Circulation* 1987, 76:458-468.

Gross et al. "Beneficial actions of superoxide dismutase and catalase in stunned myocardium of dogs." *American Journal of Physiology* 1986, 250:H372-H377.

Hearse et al. "Xanthine oxidase: a critical mediator of myocardial injury during ischemia and reperfusion." *Acta Physiol Scand* 1986, 548:65-74.

Such et al. "Beneficial effects of N-acetylcysteine on acute myocardial infarction in open chest dogs." *Arch Pharmacol Toxicol* 1986, 12:37-40.

Bolli, R. "Oxygen-derived free radicals and post-ischemic myocardial dysfunction ('stunned myocardium')." *Journal of the American College of Cardiology* 1988, 12:239-249.

Cross et al. "Oxygen radicals and human disease." *Ann. Intern. Med.* 1987, 107:526-545.

Simpson et al. "Free radicals and myocardial ischemia and reperfusion injury." *J Lab Clin Med* 1987, 110:13-30.

Mehta et al.. "Neutrophils as potential participants in acute myocardial ischemia: relevance to reperfusion." *Journal of the American College of Cardiology* 1988, 11: 1309-1316.

Liao, M.-L., Ying, X.-Y., Chung, C., Liang, Y.-T. and Sieb, P.A. 1988 Synthesis of L-ascorbate and 6-phosphate. *Carb. Res.* 176: 73-77.

Hearse, D. J., and Tosaki, A. "Free radicals and calcium: simultaneous interacting triggers as determinants of vulnerability to reperfusion-arrhythmias in the rat heart". *Journal of Molecular and Cellular Cardiology* 1988, 20:213-223.

Mashovsky, M. D. Tocopherol acetate (Tocopheroli acetas) 6-Acetoxy-2-methyl-2-(4,8,12-trimethyltridecyl)-chromane. pp. 37-38. Aevit (Aevitum). p. 41. Acetysalicylic acid (Acidum acetylsalicylicum). p. 190. 1988, *In Medicinal Substances*, Part 2, 1988. (Russian, abstracts in English).

Pung et al. "b-Carotene and canthaxanthin inhibit chemically- and physically-induced neoplastic transformation in 10T1/2 cells." *Carcinogenesis*, 1988, 9: 533-1539.

Bertram, et al. "Development of in vitro systems for chemoprevention research". *Prev.Med.* 1989, 18:562-575.

Bolli et al. "Direct evidence that oxygen-derived free radicals contribute to post-ischemic myocardial dysfunction in the intact dog." *Proceeding of the National Academy of Sciences, U.S.A.* 1989, 86:4695-4699.

Opie, L. H. "Reperfusion injury and its pharmacologic modification." *Circulation* 1989, 80:1049-1092.

Steinberg et al. "Beyond cholesterol: modifications of low-density lipoprotein that increase its atherogenicity." *New England Journal of Medicine* 1989, 320: 915.

Terao, J. "Antioxidant activity of beta-carotene-related carotenoids in solution." *Lipids* 1989, 24: 659-661.

In *Drug Facts and Comparisons*. 1990 Ed. Sewester, C. S., Olin, B. R., Hebel, S. K., Eds. Facts and Comparisons Division, J. B. Lippincott Co., St. Louis, MO. pp. 6, 7, 13, 14, 60, 62, 997, 998.

Chopra et al. "Free radical scavenging: potentially beneficial action of thiol-containing angiotensin-converting enzyme inhibitors." *Biochem Soc Trans* 1990, 18:1184-1185.

Davies et al. "Lipid peroxidation associated with successful thrombolyis." *Lancet* 1990, 335:741-743.

Di Mascio et al. "Carotenoids, tocopherols, and thiols and biological singlet molecular oxygen quenchers." *Biochem Soc Trans* 1990; 18: 1054-1056.

Fedan, J. S.(1990) "Anticoagulant, antiplatelet, and fibrinolytic (thrombolytic) drugs." In *Modern Pharmacology*. Third Ed, Little, Brown and Co., Boston, MA.

Johansson et al. "Recombinant human extracellular superoxide dismutase reduces concentration of oxygen free radicals in the reperfused rat heart." *Cardiovascular Research* 1990, 24:500-503.

Kurashige et al. "Inhibition of oxidative injury of biological membranes by astaxanthin." *Physiol Chem Phys & Med NMR* 1990, 22:27-38.

Rogers et al. "Retinoid-enhanced gap junctional communication is achieved by increased levels of *connexin 43* mRNA and protein" *Molecular Carcinogenesis* 1990, 3: 335-343.

Shuter et al. "Studies on the effects of antioxidants and inhibitors of radical generation on free radical production in the reperfused rat heart using electron spin resonance spectroscopy." *Free Radicical Research Communications* 1990, 9: 223-232.

Williams et al. "The relationship between neutrophils and increased microvascular permeability in a model of myocardial ischemia and reperfusion in the rabbit." *British Journal of Pharmacology*, 1990, 100:729-734.

Bertram et al. "Diverse carotenoids protect against chemically induced neoplastic transformation." *Carcinogenesis* 1991, 12:671-678.

Di Mascio et al. "Antioxidant defense systems: the role of carotenoids, tocopherols, and thiols." *Am J Clin Nutr* 1991, 53: 194S-200S.

Axford-Gatley and Wilson "Reduction of experimental myocardial infarct size by oral administration of alpha-tocopherol." *Cardiovascular Research*, 1991, 25: 89-92.

Conorev et al. "Improvement in contractile recovery of isolated rat heart after cardioplegic ischemic arrest with endogenous phosphocreatine: involvement of antiperoxidative effect?" *Cardiovascular Research* 1991, 25: 164-171.

Esterbauer et al. "Effect of antioxidants on oxidative modification of LDL." *Ann Med* 1991, 23(5): 573-581.

McMurray and Chopra "Influence of ACE inhibitors on free radicals and reperfusion injury: pharmacological curiosity or therapeutic hope?" *British Journal of Pharmacology* 1991, 31: 373-379.

Petty et al. "Effect of a cardioselective alpha-tocopherol.analogue on reperfusion injury in rats induced by myocardial ischemia." *European Journal of Pharmacology* 1991, 192: 383-388.

Miki, W. "Biological functions and activities of animal carotenoids." *Pure Appl Chem* 1991, 63(1): 141-146.

Welbourn et al. "Pathophysiology of ischemia reperfusion injury: central role of the neutrophil." *British Journal of Surgery* 1991, 78: 651-655.

Gabrielson et al. "Measurement of neutrophil activation and epidermal cell toxicity by palytoxin and 12-O-tetradecanoylphorbol-13-acetate." *Carcinogenesis* 1992, 13 1671-1674.

Hearse and Bolli . "Reperfusion induced injury: manifestations, mechanisms, and clinical.relevance." *Cardiovascular Research* 1992, 26:101-108.

Kimura et al. "Moderation of myocardial ischemia reperfusion injury by calcium channel and calmodulin receptor inhibition." *Heart Vessels* 1992, 7:189-195.

Lim et al. "Antioxidant activity of xanthophylls on peroxyl radical-mediated phospholipid peroxidation." *Biochim. Biophys. Acta* 1992, 1126: 178-184.

Palozza, P. and Krinsky, N. I. "Astaxanthin and canthaxanthin are potent antioxidants in a membrane model." *Arch. Biochem. Biophys.* 1992, 297: 291-295.

Zhang et al. "Carotenoids up-regulate connexin 43 gene expression independent of their pro-vitamin A or antioxidant properties." *Cancer Res.*, 1992, 52: 5707-5712.

Ames et al. "Oxidants, antioxidants, and the degenerative diseases of aging." *Proceeding of the National Academy of Sciences, U.S.A.* 1993, 90:7915-7922.

Baxter, G. F., and Yellon, D. M. "Attenuation of reperfusion-induced ventricular fibrillation in the rat isolated hypertrophied heart by preischemic diltiazem treatment." *Cardiovasc Drugs Ther* (1993). 7: 225-231.

Clevidence, B. A., and Bieri, J. G. "Association of carotenoids with human plasma lipoproteins." *Methods in Enzymology* (1993) 214: 33-46.

Grech et al. "Free-radical generation during angioplasty reperfusion for acute myocardial infarction." *Lancet* (1993). 341: 990-991.

Grech et al. "Differential free-radical activity after successful and unsuccessful thrombolytic reperfusion in acute myocardial infarction." *Coron. Artery Dis.* (1993). 4(9): 769-74.

Hossain et al. "Retinoids and carotenoids upregulate gap junctional communication: correlation with enhanced growth control and cancer prevention." In *Progess in Cell Research vol. 3: Gap Junctions.* (1993) Elsiever, Amsterdam, pp. 301-309.

Jimenez, C., and Pick, U. "Differential reactivity of beta-carotene isomers from *Dunaliella bardawil* toward oxygen radicals." *Plant Physiol* (1993). 101: 385-390.

Oshima et al. "Inhibitory effect of beta-carotene and astaxanthin on photosensitized oxidation of phospholipid bilayers." *J Nutrit Sci Vitaminol* (1993). 39: 607-615.

Bertram, J.S. and Zhang, L.-X. Assays for the regulation of gap junctional communication and connexin expression by carotenoids. (1994) *Methods Enzymol.* 234: 235-244.

MacIsaac et al. "Toward the quiescent coronary plaque." *Journal of the American College of Cardiology* (1993) 22:1228-1241.

Oliveros et al. Quenching of singlet oxygen by carotenoid derivatives: kinetic analysis by near-infrared luminescence *New J. Chem.* (1994) 18:535-539.

Singh et al. "Plasma levels of antioxidant vitamins and oxidative stress in patients with acute myocardial infarction." *Acta Cardiologica* (1994) vol. XLIX 5: 441-452.

Tinkler et al. "Dietary carotenoids protect human cells from damage." *Journal of Photochemistry and Photobiology.* (1994) 26: 283-285.

Britton, G. "Structure and properties of carotenoids in relation to function." *The FASEB Journal*, (1995) 9: 1551-1558.

Leist et al. "Tumor necrosis factor-induced hepatocyte apoptosis precedes liver failure in experimental murine shock models." *American Journal of Pathology* (1995) 146: 1220-1234.

Navab et al. "Pathogenesis of atherosclerosis." *American Journal of Cardiology* (1995) 76(9): 18C-23C.

Peters, N. S. "Myocardial gap junction organization in ischemia and infarction." *Microsc. Res. Tech.* (1995) 31, 375-386.

Singh et al. "Effect of antioxidant-rich foods on plasma ascorbic acid, cardiac enzymes, and lipid peroxide levels in patients hospitalized with acute myocardial infarction." *J Am Diet Assoc* (1995). 95: 775-780.

Torrissen, 0. J., and Christiansen, R. "Requirements for carotenoids in fish diets." *J Appl Ichthyol* (1995). 11: 225-230.

Aviram, M. "Interaction of oxidized low density lipoprotein with macrophages in atherosclerosis, and the antiatherogenicity of antioxidants." *Eur J Clin Chem Clin Biochem* (1996). 34(8): 599-608.

Ben-Amotz, A., and Levy, Y. "Bioavailability of a natural isomer mixture compared with synthetic all-*trans* beta-carotene in human serum." *Am J Clin Nutr* (1996). 63: 729-734.

Mayne, S. "Beta-carotene, carotenoids, and disease prevention in humans." *The FASEB Journal* (1996). 10: 690-701.

Moore, A.S., and Papas, A. M. "Biochemistry and health significance of Vitamin E." *J. Adv. Med.* (1996). 9 11-29.

Parker, R. S. Absorption, metabolism, and transport of carotenoids. *The FASEB Journal* (1996) 10: 542-551.

Peters, T. "Ligand binding by albumin." In *All About Albumin*, Academic Press, San Diego (CA), 1996. pp. 76-128.

Schaer et al. "Beneficial effects of RheothRx injection in patients receiving thrombolytic therapy for acute myocardial infarction. Results of a randomized, double-blind, placebo-controlled trial." *Circulation* (1996) 94(3): 298-307.

Shimidzu et al. "Carotenoids as singlet oxygen quenchers in marine organisms." *Fisheries Science* (1996). 62(1): 134-137.

Serrano et al. "Superoxide and hydrogen peroxide induce CD18-mediated adhesion in the postischemic heart." *Biochim. Biophys. Acta* (1996). 1316: 191-202.

Singh et al. "Usefulness of antioxidant vitamins in suspected acute myocardial infarction (the Indian experiment of infarct survival-3." *Am J Cardiol* (1996). 77: 232-236.

Stephens et al. "Randomised controlled trial of vitamin E in patients with coronary disease: Cambridge Heart Antioxidant Study (CHAOS)." *Lancet* (1996). 347(9004): 781-6.

Goulinet, S., and Chapman, M. J. "Plasma LDL and HDL subspecies are heterogeneous in particle content of tocopherols and oxygenated and hydrocarbon carotenoids: relevance to oxidative resistance and atherogenesis." *Arterioscler Thromb Vasc Biol* (1997). 17: 786-796.

Kim et al. "Zeaxanthin dipalmitate from *Lycium chinense* has hepatoprotective activity." *Res. Comm. Mol. Path. Pharm.* (1997). 97: 301-314.

Maxwell and Lip "Reperfusion injury: a review of the pathophysiology, clinical manifestations and therapeutic options." *Int J Cardiol* (1997). 58: 95-117.

Mortensen et al. "Comparative mechanisms and rates of free radical scavenging by carotenoid antioxidants." *FEBS Lett.* (1997) 418: 91-97.

Oshima et al. "Accumulation and clearance of capsanthin in blood plasma after the ingestion of paprika juice in men." *J Nutr* (1997). 127: 1475-1479.

Perkins et al. "Three-dimensional structure of the gap junction connexon." *Biophysical Journal*, (1997) 72, 533-544.

Turujman et al. "Rapid liquid chromatographic method to distinguish wild salmon from aquacultured salmon fed synthetic astaxanthin." *Journal of AOAC International* (1997): 80(3): 622-632.

Holvoet et al. "Oxidized LDL and malondialdehyde-modified LDL in patients with acute coronary syndromes and stable coronary artery disease." *Circulation* (1998) 98: 1487-1494.

Kaprielian et al. "Downregulation of immunodetectable connexin 43 and decreased gap junction size in the pathogenesis of chronic hibernation in the human left ventricle." *Circulation* (1998). 97: 651-60.

Levy et al. "Plasma antioxidants and lipid peroxidation in acute myocardial infarction and thrombolysis." *J Am Coll Nutr* (1998). 17 (4): 337-341.

Saez et al. "Regulation of gap junctions by protein phosphorylation." *Braz.J.Med.Biol.Res.*, (1998) 31, 593- 600.

Saffitz, J. E., and Yamada, K. A. "Do alterations in intercellular coupling play a role in cardiac contractile dysfunction?" *Circulation* (1998). 97: 630-632.

Singh et al. "Randomized, double-blind placebo-controlled trial of coenzyme Q10 in patients with acute myocardial infarction." *Cardiovasc. Drugs Ther.* (1998). 12: 347-353.

Bertram, J. S. "Carotenoids and gene regulation." *Nutr Rev* (1999). 57(6): 182-191.

Boileau et al. "Carotenoids and vitamin A", In *Antioxidant status, diet, nutrition, and health*. CRC Press, (1999). Boca Raton, FL, pp. 133-158.

Boileau et al. "*Cis*-lycopene is more bioavailable than *trans*-lycopene in vitro and in vivo in lymph-cannulated ferrets." *J Nutr* (1999). 129: 1176-1181.

Buffon et al. "Preprocedural serum levels of C-reactive protein predict early complications and late restenosis after coronary angioplasty." *Journal of the American College of Cardiology* (1999). 34(5): 1512-21.

Curry et al. "Fatty acid binding to human serum albumin: new insights from crystallographic studies". Biochim. Biophys. Acta. 1999, 1441:131-140.

Fernandez-Cobo et al. "Downregulation of connexin 43 gene expression in rat heart during inflammation: The role of tumor necrosis factor". 1999, *Cytokine* 11(3):216-24.

Hennekens, "Antioxidant vitamins and cardiovascular disease" In *Antioxidant status, diet, nutrition, and health*. CRC press, (1999) Boca Raton, FL pp. 463-477.

Horwitz et al. "Timing of treatment for myocardial reperfusion injury." *J Cardiovasc Pharmacol* (1999). 33 (1): 19-29.

Huang et al. "Heterogeneous loss of connexin 43 protein in ischemic dog hearts." *J Cardiovasc Electrophysiol* (1999) 10(1): 79-91.

Jewell and O'Brien. "Effect of dietary supplementation with carotenoids on xenobiotic metabolizing enzymes in the liver, lung, kidney and small intestine of the rat." *British Journal of Nutrition*. (1999) 81(3):235-42.

Lagrand et al. "C-reactive protein as a cardiovascular risk factor: more than an epiphenomenon?" *Circulation*, 1999, 100(1):96-102.

Lowe et al. "Carotenoid composition and antioxidant potential in subfractions of human low-density lipoprotein." *Ann Clin Biochem* (1999), 36: 323-332.

Mahaffey et al. "Adenosine as an adjunct to thrombolytic therapy for acute myocardial infarction." *Journal of the American College of Cardiology* (1999). 34(6): 1711-1720.

Papas, A.M. "Antioxidant status: diet, health and disease; Part I: Factors affecting antioxidant status and its role." *Mature Medicine* (1999) 315-319.

Sajkowska et al. "Fibrinolytic therapy and n-acetylcysteine in the treatment of patients with acute myocardial infarction: its influence on authentic plasma hydroperoxide levels and polymorphonuclear neutrophil oxygen metabolism." *Cardiology* (1999). 91: 60-65.

Arab and Steck "Lycopene and cardiovascular disease." *Am J Clin Nutr*(2000). 71 (supp):1691S-1695S.

Bhattacharya et al. Crystallographic analysis reveals common modes of binding of medium and long-chain fatty acids to human serum albumin. *J. Mol. Biol.* (2000) 303: 721-732.

Ding and Hu: "The synthesis of vicinal halohydrin phosphates via highly regioselective ring opening of epoxides with dialkyl halophophate." *J. Chem. Chem. Soc., Perkin. Trans.* 2000 1:1651-1655.

Devaraj and Jialal "Alpha tocopherol supplementation decreases serum C-reactive protein and monocyte interleukin-6 levels-in normal volunteers and type 2 diabetic patients." *Free Radical Biology Medicine* (2000). 29(8): 790-2.

Iwamoto et al. "Inhibition of low-density lipoprotein oxidation by astaxanthin." *Journal of Atherosclerosis and Thrombosis* (2000). 7: 216-222.

Jollis, J. G. and Romano, P. S. "Volume-outcome relationship in acute myocardial infarction." *J. Am. Med. Soc.* (2000). 284(24): 3169-3171.

Jyonouchi et al. "Antitumor activity of astaxanthin and its mode of action." *Nutrition and Cancer* 2000, 36(1):59-65.

Lee et al. "Biphasic regulation of leukocyte superoxide generation by nitric oxide and peroxynitrite." *Journal of Biological Chemistry* (2000). 275: 38965-38972.

Magid et al. "Relation between hospital primary angioplasty volume and mortality for patients with acute MI treated with primary angioplasty vs thrombolytic therapy." *Journal of the American Medical Association*, 2000, 284(24):3169-71.

Mycek et al. *Lippincott's Illustrated Reviews: Pharmacology.* (2000). Lippincott Williams & Wilkins, pp. 201-204.

Orset and Young "Exposure to low irradiances favors the synthesis of 9-cis beta,beta carotene in *Dunaliella salina* (Teod.)." *Plant Physiol* (2000). 122: 609-617.

Osterlie et al. "Plasma appearance and distribution of astaxanthin E/Z and R/S isomers in plasma lipoproteins of men after single dose administration of astaxanthin." *J Nutr Biochem* (2000). 11: 482-490.

Ounpuu et al. "The global burden of cardiovascular disease." *Medscape Cardiology* (2000). 04: 1-5.

Peters and Wit "Gap junction remodeling in infarction: does it play a role in arrhythmogenesis?" *J Cardiovasc Electrophysiol* (2000). 11(4): 488-90.

Sethi et al. "Beneficial effects of vitamin E treatment in acute myocardial infarction." *J Cardiovasc Pharmacol Ther* (2000). 5: 51-58.

Upritchard et al. "Effect of supplementation with tomato juice, vitamin E, and vitamin C on LDL oxidation and products of inflammatory activity in type 2 diabetes." *Diabetes Care* (2000). 23(6): 733-738.

Watanabe et al. "Role of Arg-410 and Tyr-411 in human serum albumin for ligand binding and esterase-like activity." *Biochemical Journal* (2000) 349: 813-819.

Di Napoli et al. "C-reactive protein in ischemic stroke: an independent prognostic factor." *Stroke* (2001). 32(4): 917-24.

Duilio et al. "Neutrophils are primary source of $O_2$ radicals during reperfusion after prolonged myocardial ischemia." *Am. J. Physiol. Heart Circ. Physiol.* (2001). 280 H2649-H2657.

Goto et al. "Efficient radical trapping at the surface and inside the phospholipids membrane is responsible for highly potent antiperoxidative activity of the carotenoid astaxanthin." *Biochimica et Biophysica Acta* (2001). 1512: 251-258.

Jialal et al. "Is there a vitamin E paradox?" *Current Opinions in Lipidology* (2001). 12: 49-53.

Kang et al. "Effect of astaxanthin on the hepatotoxicity, lipid peroxidation and antioxidative enzymes in the liver of CC14-treated rats." *Methods Find Exp Clin Pharmacol.* (2001). 23(2): 79-84.

Petitpas et al. "Crystal structures of human serum albumin complexed with monounsaturated and polyunsaturated fatty acids." *The Journal of Molecular Biology* (2001). 314: 955-960.

Lutnaes et al. "Is (9Z)-'meso'-zeaxanthin optically active?" *Chirality* (2001). 13: 224-229.

Roe et al. "Shifting the open-artery hypothesis downstream: the quest for optimal reperfusion." *Journal of the American College of Cardiology* (2001). 37: 9-18.

Zsila et al. "Investigation of the self-organization of lutein and lutein diacetate by electronic absorption, circular dichroism spectroscopy, and atomic force microscopy." *J. Phys. Chem.* (2001) B 105: 9413-9421.

Zsila et al. "Induced chirality upon crocetin binding to human serum albumin: origin and nature." *Tetrahedron: Assymmetry* (2001) 12: 3125-3137.

Zsila et al.. "Supramolecular assemblies of carotenoids." *Chirality*, 2001, 13:739-744.

Barrett et al. "C-reactive protein associated increase in myocardial infarct size after ischemia/reperfusion." *Journal of Pharmacology and Experimental Therapeutics* (2002). 303(3): 1007-1013.

Bikádi et al. "The supramolecular structure of self-assembly formed by capsanthin derivatives." *Enantiomer* (2002) 7: 67-76.

Choi et al. "Interactions of very long-chain saturated fatty acids with serum albumin." *J. Lipid Res.* (2002) 43: 1000-1010.

Kistler et al. "Metabolism and CYP-inducer properties of astaxanthin in man and primary human hepatocytes." *Arch. Toxicol.* (2002) 75: 665-675.

Kragh-Hansen et al. "Practical aspects of the ligand-binding and enzymatic properties of human serum albumin." *Biol. Pharm. Bull.* (2002) 25: 695-704.

Rao and Agarwal "Bioavailability and in vivo antioxidant properties of lycopene from tomato products and their possible role in the prevention of cancer." *Nutrition and Cancer* 1998, vol. 31, pp. 199-203.

Kim et al. "Electronic absorption and Raman studies of the radical anion and dianion of a polyene molecule (19,19',20,20'-tetranor-b,b-carotene)." *Chemical Physical Letters* 1997, vol. 276, pp. 418-422.

Duhamel et al., "Terminally substituted linear conjugated polyenes: precursors of molecular wires." *Tetrahedron Letters* 1993, vol. 34, pp. 7399-7400.

Xu et al. "TXA2-PGI2 balance disorder in rat brain with incomplete cerebral ischemia and reperfusion, and the correction of this imbalance by carthamic xanthophyll." *Jinan Daxue Xuebao, Ziran Kexue Yu Yixueban*, 1993, vol. 14, pp. 34-38 (Abstract only).

Engster, "Beilstein Institut zur Foerderung der chemischen Wissenschaft, Tunaxanthin, Database accession No. 2313964." Carotenoid Chemistry and Biochemistry, Proceedings of the 6th International Symposium on Carotenoids, 1981, pp. 1-9 (Abstract only).

Baldus et al. "Myeloperoxidase Serum Levels Predict Risk in Patients With Acute Coronary Syndromes", *Circulation*, 2003, vol. 108, pp. 1440-1445.

Drazen et al., "Treamnet od Asthma With Drugs Modifyingthe Leukotriene Pathway", 2004, *N. Engl. J, Med.* vol. 340, pp. 197-206.

Dwyer et al., "Arachidonate 5-Lipoxygenase Promoter Genotype, Dietary Arachidonic Acid, and Atherosclerosis", 2004, *N. Engl. J. Med.*, vol. 350, pp. 29-37.

Hellagotir et al., "The gene encoding 5-lipoxygenase activating protein confers risk of myocardial infarction and stroke", 2004, *Nat. Genetics*, vol. 36, pp. 223-239.

Lee et al., "Astaxanthin inhibits Nitric Oxide production and inflammatory gene expression by suppressing IκB kinase-dependent NF-κB activation", 2003, *Mol. Cells*, vol. 16, pp. 97-105.

Shishehbor, et al., "Statins promote potent systemic antioxidant effects through specific inflammatory pathways", 2003, *Circulation*, vol. 108, pp. 426-431.

Spanbroek et al., "Expanding expression of the 5-lipoxygenase pathway within the arterial wall during human atherogenesis", 2003, *Proc. Nat'l Acad. Sci. U.S.A.*, vol. 100, pp. 1238-1243.

Spector et al., "Hydroxyeicosatetraenoic Acids (HETEs)", 1988, *Prog. Lipid Res.*, vol. 27, pp. 271-323.

Zhang et al., "Myeloperoxidase functions as a major enzymatic catalyst for initiation of lipid peroxidation at sites of inflammation", 2002, *J. Biol. Chem.*, vol. 277, pp. 46116-46122.

A. disuccinic acid astaxanthin ester

B. disodium disuccinic acid ester astaxanthin salt (DDA; Cardax™)

C. divitamin C disuccinate astaxanthin ester

CAROTENOID ANALOGS OR DERIVATIVES FOR THE INHIBITION AND AMELIORATION OF INFLAMMATION

PRIORITY CLAIM

This application claims priority to Provisional Patent Application No. 60/562,195 entitled "CAROTENOID ANALOGS OR DERIVATIVES FOR THE INHIBITION AND AMELIORATION OF INFLAMMATION" filed on Apr. 14, 2004.

BACKGROUND OF THE INVENTION

1. Field of the Invention

The invention generally relates to the fields of medicinal and synthetic chemistry. More specifically, the invention relates to the synthesis and use of carotenoid analogs or derivatives.

2. Description of the Relevant Art

Recent studies have demonstrated that initiation of lipid peroxidation and formation of bioactive eicosanoids are critical processes occurring in inflammation, particularly in both atherosclerosis and asthma (reactive airways disease; Zhang et al. 2002; Spanbroek et al. 2003; Dwyer et al. 2004; Helgadottir et al. 2004 are each incorporated herein). The current state of knowledge suggests that lipoxygenases, cyclooxygenases, and cytochrome P450 monooxygenases (CYPs) are the primary enzymatic participants in these lipid peroxidation events (Spector et al. 1988 (incorporated herein); Zhang et al. 2002). In addition, myeloperoxidase (MPO), a heme protein secreted by activated leukocytes, can also generate reactive intermediates that promote lipid peroxidation in vitro and in vivo (Baldus et al. 2003; Brennan et al. 2003 which are each incorporated herein).

In addition to their potent bronchoconstrictor properties, leukotrienes and other products of the 5-lipoxygenase pathway induce pathophysiologic responses similar to those associated with asthma. Specifically, 5-lipoxygenase products can cause tissue edema and migration of eosinophils and can stimulate airway secretions. The leukotrienes also stimulate cell cycling and proliferation of both smooth muscle and various hematopoietic cells; these observations provide further evidence of a potential role of leukotriene modifiers in altering the biology of the airway wall in asthma. Since all these responses contribute to asthma, the pharmaceutical industry initiated research programs to identify substances that could inhibit the action or synthesis of the leukotrienes.

Inhibition of 5-LO pathway activity in vivo will likely find application in those anti-inflammatory applications (e.g. atherosclerosis, asthma) for which downstream mediators of 5-LO activity (e.g. leukotriene B4 or $LTB_4$) are involved in the pathogenesis of disease.

SUMMARY

In some embodiments, the administration of analogs or derivatives of carotenoids may inhibit and/or ameliorate the occurrence of certain maladies in subjects. Maladies that may be treated with analogs or derivatives of carotenoids embodied herein may include diseases that provoke, trigger or are associated with an inflammatory response. In some embodiments, analogs or derivatives of carotenoids may be water-soluble.

In an embodiment, at least a portion of the pathological complications associated with asthma may be ameliorated or inhibited in a patient by administering analogs or derivatives of carotenoids embodied herein.

In an embodiment, administering analogs or derivatives of carotenoids embodied herein to a subject may modulate or affect the bioavailability of eicosanoids.

In an embodiment, at least a portion of the pathological complications associated with atherosclerosis may be ameliorated or inhibited in a patient by administering analogs or derivatives of carotenoids embodied herein.

In an embodiment, administering the analogs or derivatives of carotenoids embodied herein to a subject may control or affect the bioavailability of 5-lipoxygenase (LO)-catalyzed eicosanoid metabolites. In an embodiment, 5-LO-catalyzed eicosanoid metabolites that may be controlled or affected by administering analogs or derivatives of carotenoids to a subject may include proinflammatory effector molecules (e.g., leukotrienes). Administration of analogs or derivatives of carotenoids according to the preceding embodiments may at least partially inhibit and/or influence the pathological complications associated with inflammation.

In some embodiments, the administration of structural analogs or derivatives of carotenoids by one skilled in the art—including consideration of the pharmacokinetics and pharmacodynamics of therapeutic drug delivery—is expected to inhibit and/or ameliorate disease conditions.

In some of the foregoing embodiments, analogs or derivatives of carotenoids administered to cells may be at least partially water-soluble.

Water-soluble carotenoid analogs or derivatives may have a water solubility of greater than about 1 mg/mL in some embodiments. In certain embodiments, water-soluble carotenoid analogs or derivatives may have a water solubility of greater than about 10 mg/mL. In some embodiments, water-soluble carotenoid analogs or derivatives may have a water solubility of greater than about 50 mg/mL.

In an embodiment, the administration of water soluble analogs or derivatives of carotenoids to a subject may inhibit and/or ameliorate some types of diseases that provoke or trigger an inflammatory response. In some embodiments, water-soluble analogs or derivatives of carotenoids may be administered to a subject alone or in combination with other carotenoid analogs or derivatives.

Embodiments may be further directed to pharmaceutical compositions comprising combinations of structural carotenoid analogs or derivatives to said subjects. The composition of an injectable structural carotenoid analog or derivative of astaxanthin may be particularly useful in the therapeutic methods described herein. In yet a further embodiment, an injectable astaxanthin structural analog or derivative is administered with another astaxanthin structural analog or derivative and/or other carotenoid structural analogs or derivatives, or in formulation with antioxidants and/or excipients that further the intended purpose. In some embodiments, one or more of the astaxanthin structural analogs or derivatives are water-soluble.

In some embodiments, the administration of structural analogs or derivatives of carotenoids by one skilled in the art—including consideration of the pharmacokinetics and pharmacodynamics of therapeutic drug delivery—is expected to inhibit and/or ameliorate disease conditions associated with elevated inflammation. In some of the foregoing embodiments, analogs or derivatives of carotenoids administered to cells may be at least partially water-soluble.

"Water-soluble" structural carotenoid analogs or derivatives are those analogs or derivatives that may be formulated in aqueous solution, either alone or with one or more excipients. Water-soluble carotenoid analogs or derivatives may include those compounds and synthetic derivatives that form molecular self-assemblies, and may be more properly termed "water dispersible" carotenoid analogs or derivatives. Water-soluble and/or "water-dispersible" carotenoid analogs or derivatives may be preferred in some embodiments.

Water-soluble carotenoid analogs or derivatives may have a water solubility of greater than about 1 mg/mL in some embodiments. In certain embodiments, water-soluble carotenoid analogs or derivatives may have a water solubility of greater than about 5 mg/ml-10 mg/mL. In certain embodiments, water-soluble carotenoid analogs or derivatives may have a water solubility of greater than about 20 mg/mL. In certain embodiments, water-soluble carotenoid analogs or derivatives may have a water solubility of greater than about 25 mg/mL. In some embodiments, water-soluble carotenoid analogs or derivatives may have a water solubility of greater than about 50 mg/mL.

In some embodiments, water-soluble analogs or derivatives of carotenoids may be administered to a subject alone or in combination with additional carotenoid analogs or derivatives.

In some embodiments, methods of modulating pathological complications associated with inflammation in a body tissue of a subject may include administering to the subject an effective amount of a pharmaceutically acceptable formulation including a synthetic analog or derivative of a carotenoid. The synthetic analog or derivative of the carotenoid may have the structure

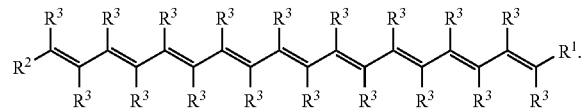

Each $R^3$ may be independently hydrogen or methyl. $R^1$ and $R^2$ may be independently a cyclic ring including at least one substituent W or acyclic group including at least one substituent W. Each cyclic ring may be independently:

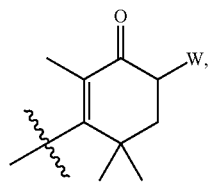 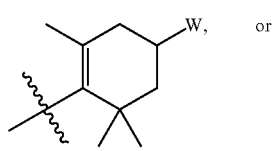 or

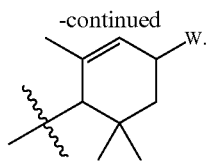

The acyclic group may have the structure

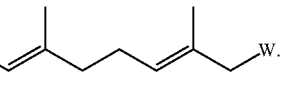

In some embodiments, at least one substituent W independently comprises

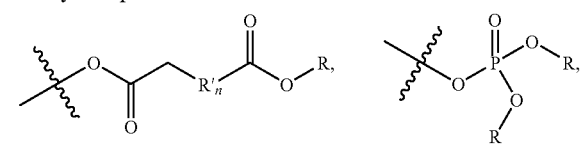

or a co-antioxidant. Each R' may be $CH_2$. n may range from 1 to 9. Each R may be independently H, alkyl, aryl, benzyl, Group IA metal, or a co-antioxidant. Each co-antioxidant may be independently Vitamin C, Vitamin C analogs, Vitamin C derivatives, Vitamin E, Vitamin E analogs, Vitamin E derivatives, flavonoids, flavonoid derivatives, or flavonoid analogs. Flavonoids may include, for example, quercetin, xanthohumol, isoxanthohumol, or genistein.

In some embodiments, a method of treating inflammation may include administering to the subject an effective amount of a pharmaceutically acceptable formulation including a synthetic analog or derivative of a carotenoid. The synthetic analog or derivative of the carotenoid may have the structure

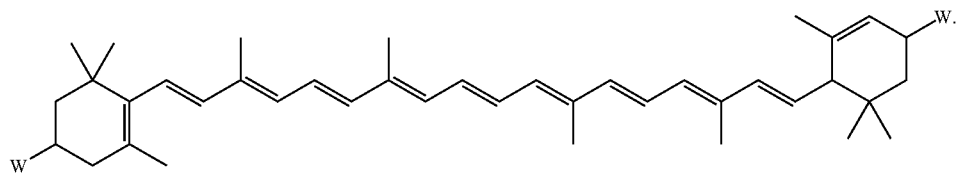

At least one substituent W may independently include

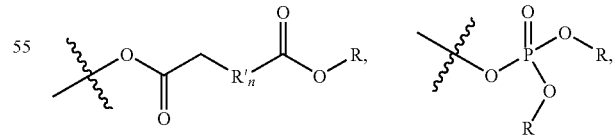

or a co-antioxidant. Each R' may be $CH_2$. n may range from 1 to 9. Each R may be independently H, alkyl, aryl, benzyl, Group IA metal, or a co-antioxidant. Each co-antioxidant may be independently Vitamin C, Vitamin C analogs, Vitamin C derivatives, Vitamin E, Vitamin E analogs, Vitamin E derivatives, flavonoids, flavonoid analogs, or flavonoid derivatives. Flavonoids may include, for example, quercetin, xanthohumol, isoxanthohumol, or genistein.

In some embodiments, the carotenoid analog or derivative may have the structure

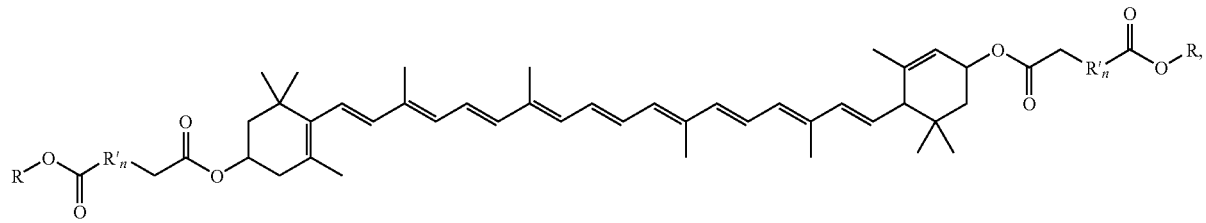

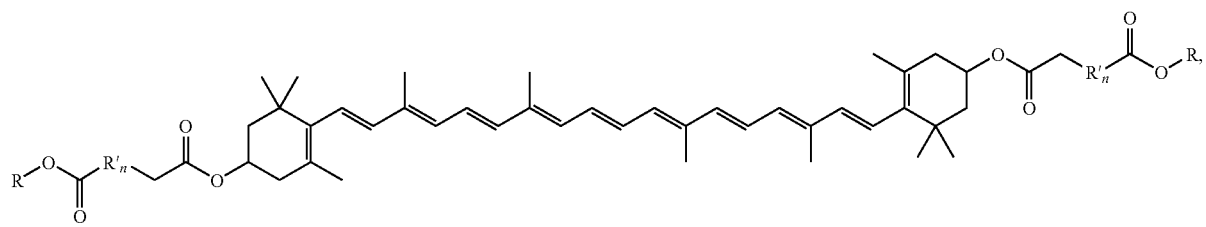

or

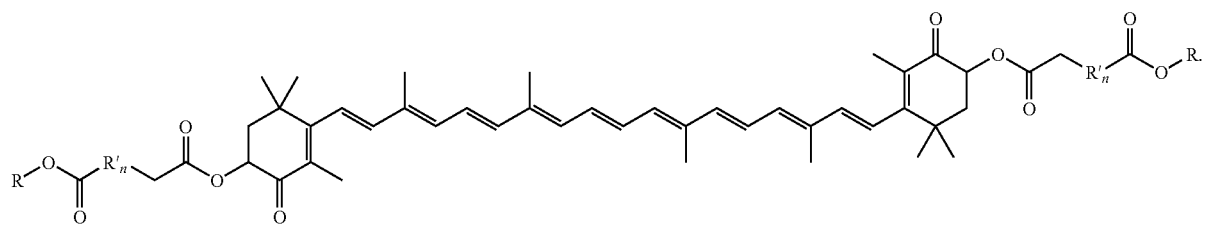

Each R' may be CH$_2$. n may range from 1 to 9. Each R may be independently H, alkyl, aryl, benzyl, a Group IA metal (e.g., Na, K, Li or the like), or a co-antioxidant. Each co-antioxidant may be independently Vitamin C, Vitamin C analogs, Vitamin C derivatives, Vitamin E, Vitamin E analogs, Vitamin E derivatives, flavonoids, flavonoid analogs, or flavonoid derivatives. Flavonoids may include, for example, quercetin, xanthohumol, isoxanthohumol, or genistein. In an embodiment, R' is CH$_2$, n is 1, and R is sodium.

In some embodiments, the carotenoid analog or derivative may have the structure

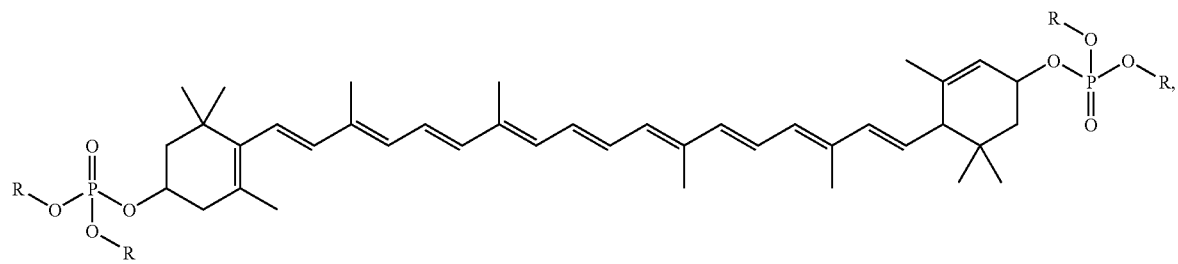

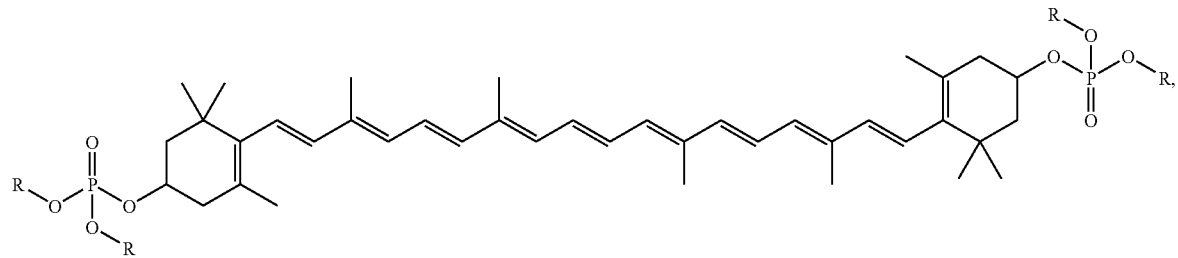

or

-continued

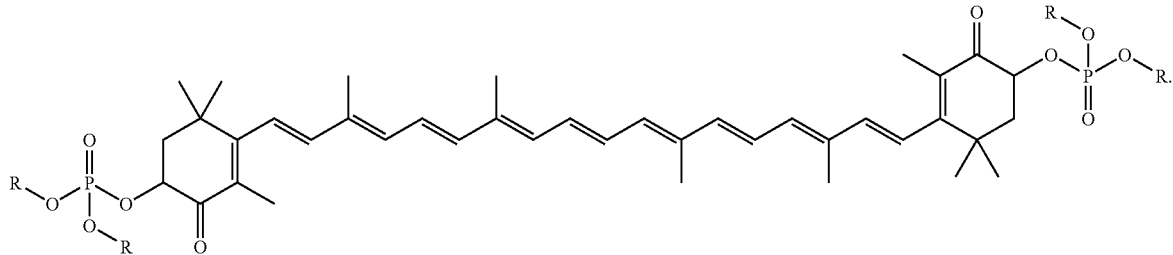

Each R may be independently H, alkyl, aryl, benzyl, a Group IA metal (e.g., Na, K, Li, or the like), or a co-antioxidant. Each co-antioxidant may be independently Vitamin C, Vitamin C analogs, Vitamin C derivatives, Vitamin E, Vitamin E analogs, Vitamin E derivatives, flavonoids, flavonoid analogs, or flavonoid derivatives. Flavonoids may include, for example, quercetin, xanthohumol, isoxanthohumol, or genistein. In an embodiment, R is sodium. When R includes Vitamin C, Vitamin C analogs, or Vitamin C derivatives, some embodiments may include carotenoid analogs or derivatives having the structure most desired). Pharmaceutical compositions including injectable structural carotenoid analogs or derivatives of astaxanthin, lutein or zeaxanthin may be particularly advantageous for the methods described herein. In yet a further embodiment, an injectable astaxanthin structural analog or derivative may be administered with a astaxanthin, zeaxanthin or lutein structural analog or derivative and/or other carotenoid structural analogs or derivatives, or in formulation with antioxidants and/or excipients that further the intended purpose. In

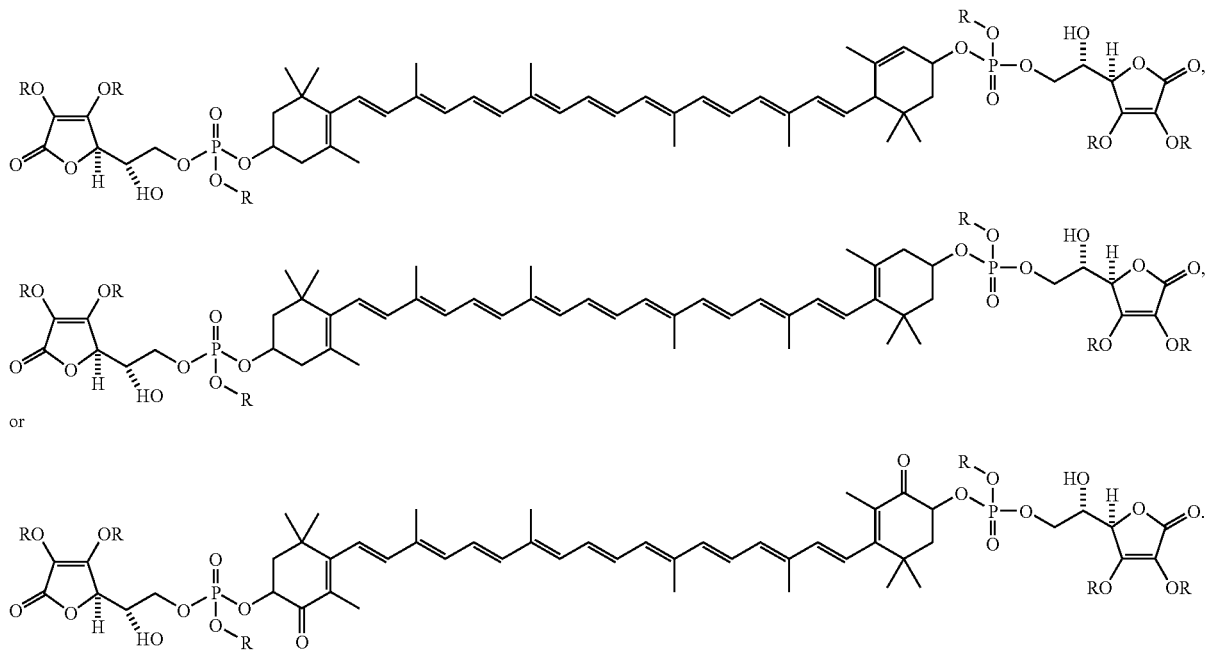

Each R may be independently H, alkyl, aryl, benzyl, or a Group IA metal.

Certain embodiments may further directed to pharmaceutical compositions including combinations two or more structural carotenoid analogs or derivatives. Embodiments directed to pharmaceutical compositions may further include appropriate vehicles for delivery of said pharmaceutical composition to a desired site of action (i.e., the site a subject's body where the biological effect of the pharmaceutical composition is most desired).

some embodiments, one or more of the astaxanthin, lutein or zeaxanthin structural analogs or derivatives are water-soluble.

BRIEF DESCRIPTION OF THE DRAWINGS

The above brief description as well as further objects, features and advantages of the methods and apparatus of the present invention will be more fully appreciated by reference to the following detailed description of presently preferred but nonetheless illustrative embodiments in accordance with the present invention when taken in conjunction with the accompanying drawings.

Figure 1:
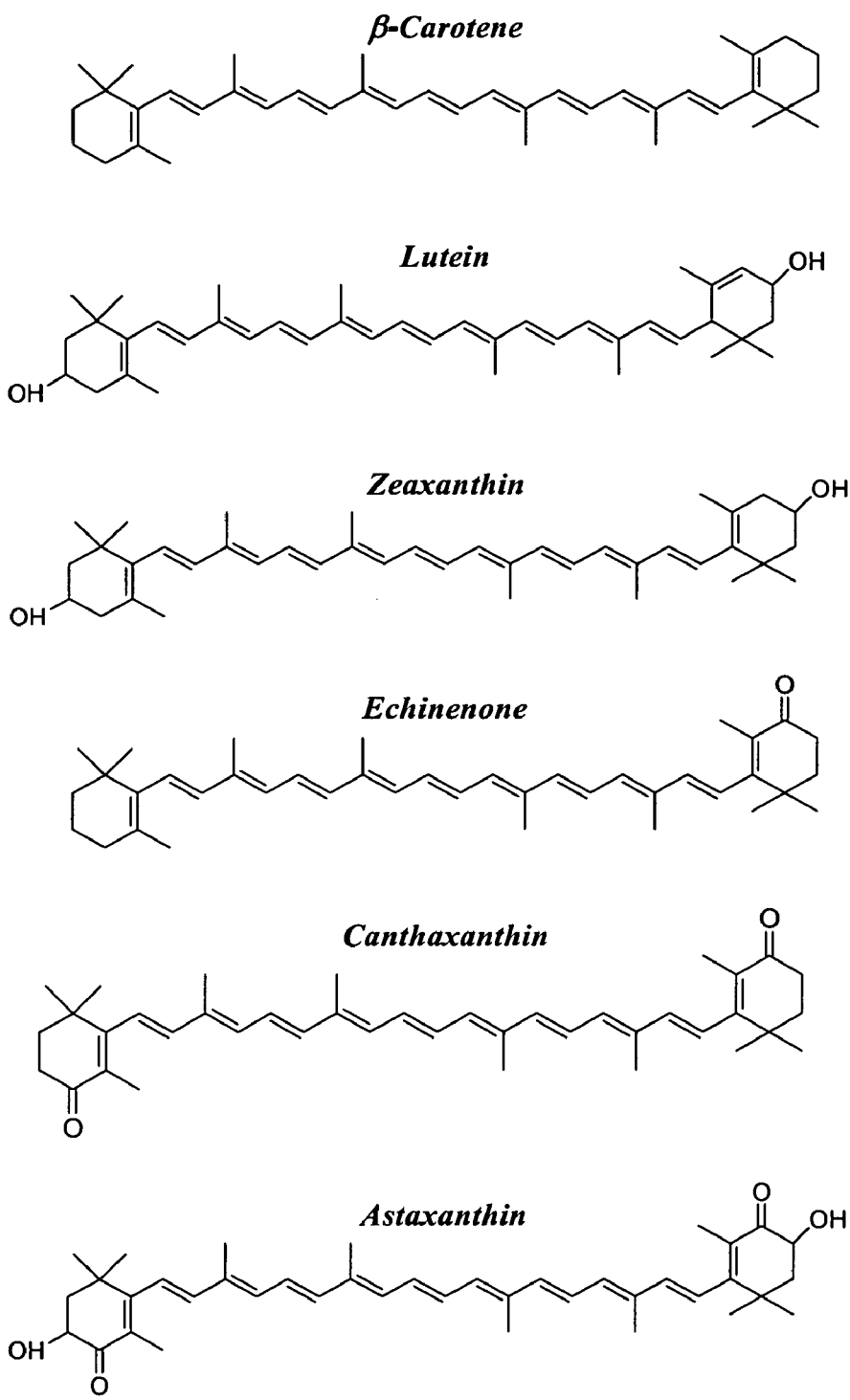
FIG. 1 is a depiction of several examples of "parent" carotenoid structures as found in nature.

While the invention is susceptible to various modifications and alternative forms, specific embodiments thereof are shown by way of example in the drawings and may herein be described in detail. The drawings may not be to scale. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION

Definitions

In order to facilitate understanding of the invention, a number of terms are defined below. It will further be understood that, unless otherwise defined, all technical and scientific terminology used herein has the same meaning as commonly understood by a practitioner of ordinary skill in the art to which this invention pertains.

Figure 10:
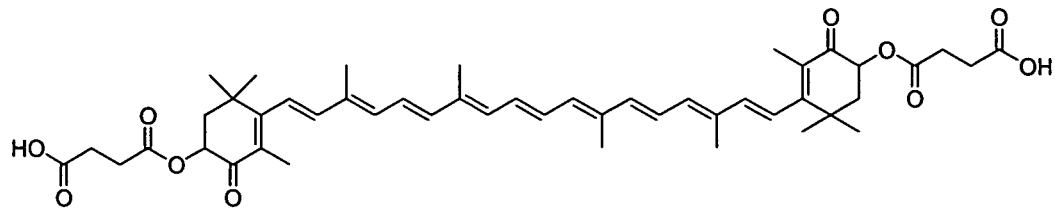
FIG. 10 is a depiction of the chemical structures of three synthetic water-soluble carotenoid analogs or derivatives according to certain embodiments. (A) disuccinic acid astaxanthin ester; (B) disodium disuccinic acid ester astaxanthin salt (Cardax™); and (C) divitamin C disuccinate astaxanthin ester.
Figure 10:
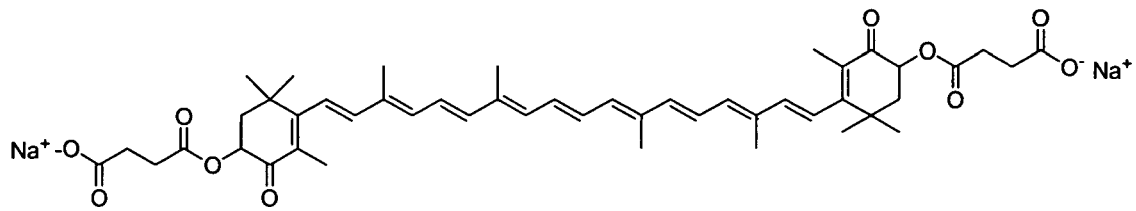
Figure 10:
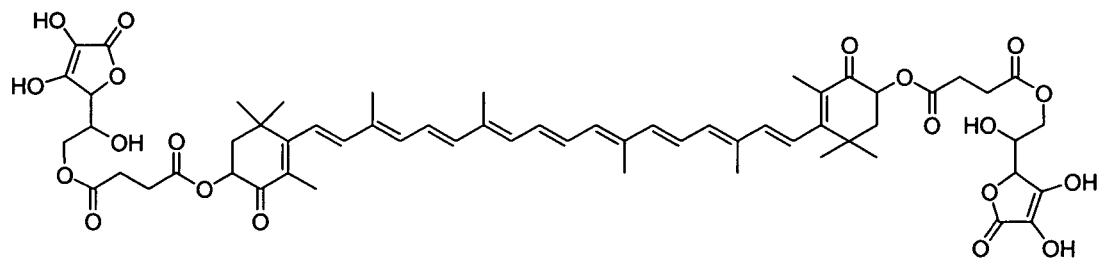

As used herein, terms such as "carotenoid analog" and "carotenoid derivative" generally refer to chemical compounds or compositions derived from a naturally occurring or synthetic carotenoid. Terms such as carotenoid analog and carotenoid derivative may also generally refer to chemical compounds or compositions that are synthetically derived from non-carotenoid based parent compounds; however, which ultimately substantially resemble a carotenoid derived analog. Non-limiting examples of carotenoid analogs and derivatives that may be used according to some of the embodiments described herein are depicted schematically in FIG. 10.

As used herein, the terms "disodium salt disuccinate astaxanthin derivative", "dAST", "ddAST", "Cardax", "Cardax™", "rac", "disodium disuccinate astaxanthin (DDA)", and "astaxanthin disuccinate derivative (ADD)" represent varying nomenclature for the use of the disodium salt disuccinate astaxanthin derivative in various stereoisomer and aqueous formulations, and represent illustrative embodiments for the intended use of this structural carotenoid analog. The diacid disuccinate astaxanthin derivative (astaCOOH) is the protonated form of the derivative utilized for flash photolysis studies for direct comparison with non-esterified, "racemic" (i.e., mixture of stereoisomers) astaxanthin.

As used herein, the term "organ", when used in reference to a part of the body of an animal or of a human generally refers to the collection of cells, tissues, connective tissues, fluids and structures that are part of a structure in an animal or a human that is capable of performing some specialized physiological function. Groups of organs constitute one or more specialized body systems. The specialized function performed by an organ is typically essential to the life or to the overall well being of the animal or human. Non-limiting examples of body organs include the heart, lungs, kidney, ureter, urinary bladder, adrenal glands, pituitary gland, skin, prostate, uterus, reproductive organs (e.g., genitalia and accessory organs), liver, gall-bladder, brain, spinal cord, stomach, intestine, appendix, pancreas, lymph nodes, breast, salivary glands, lacrimal glands, eyes, spleen, thymus, bone marrow. Non-limiting examples of body systems include the respiratory, circulatory, cardiovascular, lymphatic, immune, musculoskeletal, nervous, digestive, endocrine, exocrine, hepato-biliary, reproductive, and urinary systems. In animals, the organs are generally made up of several tissues, one of which usually predominates, and determines the principal function of the organ.

As used herein, the term "tissue", when used in reference to a part of a body or of an organ, generally refers to an aggregation or collection of morphologically similar cells and associated accessory and support cells and intercellular matter, including extracellular matrix material, vascular supply, and fluids, acting together to perform specific functions in the body. There are generally four basic types of tissue in animals and humans including muscle, nerve, epithelial, and connective tissues.

As used herein, terms such as "biological availability," "bioavailablity," or the like generally refer to the relative amount of a biologically active factor or substance that is available to carry out a biological function.

As used herein, terms such as "inflammation," "inflammatory response," or the like, generally refer to an important biological process that is a component of the immune system. Inflammation is the first response of the immune system to infection, injury or irritation in a body. Though inflammation is an important component of innate immunity, if left unabated, it may result in severe and sometimes irreparable tissue damage. Inflammation also contributes to the pathophysiology of numerous disorders such as, for example, tissue reperfusion injury following myocardial infarction, system lupus erythematosis, Crohn's disease, asthma, atherosclerosis, and the like. An inflammatory response may include bringing leukocytes and plasma molecules to sites of infection or tissue injury. Inflammation may generally be characterized as causing a tissue to have one or more of the following characteristics: redness, heat, swelling, pain and dysfunction of the organs involved. At the tissue level, the principle effects of an inflammatory response may include increased vascular permeability, recruitment of leukocytes and other inflammatory cells to the site of the inflammatory response, changes in smooth muscle contraction and the synthesis and release of proinflammatory mediator molecules, including eicosanoids.

As used herein, the term "eicosanoid" generally refers to oxygenation products of long-chain fatty acids, including any of the physiologically active substances derived from arachidonic acid. Examples of eicosanoids include, but are not limited to, prostaglandins (PGs), prostacyclins (PCs), leukotrienes (LTs), epoxyeicosatrienoic acids (EETs), and thromboxanes (TXs). Further examples of eicosanoids include those intermediate metabolites that are part of the synthetic pathways of prostaglandins, prostacyclins, leukotrienes, EETs and thromboxanes such as, for example, HETEs, HPETEs, isoprostanes, HODEs, and other such intermediate metabolites that would be readily recognized by an ordinary practitioner of the art.

As used herein, the term "lipoxygenase", or "LO" generally refers to a class of enzymes that catalyze the oxidative conversion of arachidonic acid to the hydroxyeicosetrinoic acid (HETE) structure in the synthesis of leukotrienes. The term "5-lipoxygenase", or "5-LO" generally refers to one member of this class of enzymes that has lipoxygenase and dehydrase activity, and that catalyzes the conversion of arachidonic acid to 5-hydroperoxyeicatetraenoic acid (HPETE) and leukotriene $A_4$ ($LTA_4$).

As used herein, the term "leukotriene", or "LT" generally refers to any of several physiologically active lipid compounds that contain 20 carbon atoms, are related to prostaglandins, and mediate an inflammatory response. Leukotrienes are eicosanoids that are generated in basophils, mast cells, macrophages, and human lung tissue by lipoxygenase-catalyzed oxygenation of long-chain fatty acids, especially of arachidonic acid, and that participate in allergic responses (as bronchoconstriction in asthma). Exemplary leukotrienes include $LTA_4$, $LTC_4$, $LTD_4$, $LTE_4$ and the lipoxins (LXs).

The term "modulate," as used herein, generally refers to a change or an alteration in a biological parameter. Examples of biological parameters subject to modulation according to certain embodiments described herein may include, by way of non-limiting example only: inflammation, initiation of an inflammatory reaction, enzymatic activity, protein expression, cellular activity, production of hormonal intermediates, the relative levels of hormones or effector molecules such as, for example, eicosanoids, leukotrienes, prostaglandins, or intermediates thereof, or the like. "Modulation" may refer to a net increase or a net decrease in the biological parameter. Furthermore, it will be readily apparent to one of ordinary skill in the art that modulating a biological parameter can, in some instances, affect biological processes that themselves depend on that parameter. As used herein the terms "inhibiting" and "ameliorating," when used in the context of modulating a pathological or disease state, generally refers to the prevention and/or reduction of at least a portion of the negative consequences of the disease state. When used in the context of biochemical pathway or of protein function, the term "inhibiting" generally refers to a net reduction in the activity of the pathway or function.

As used herein the terms "subject" generally refers to a mammal, and in particular to a human.

As used herein the terms "administering," when used in the context of providing a pharmaceutical composition to a subject generally refers to providing to the subject one or more pharmaceutical, "over-the-counter" (OTC) or nutraceutical compositions via an appropriate delivery vehicle such that the administered compound achieves one or more biological effects for which the compound was administered. By way of non-limiting example, a composition may be administered parenteral, subcutaneous, intravenous, intracoronary, rectal, intramuscular, intra-peritoneal, transdermal, or buccal routes of delivery. The dosage of pharmacologically active compound that is administered will be dependent upon the age, health, weight, and/or disease state of the recipient, concurrent treatments, if any, the frequency of treatment, and/or the nature and magnitude of the biological effect that is desired.

As used herein, terms such as "pharmaceutical composition," "pharmaceutical formulation," "pharmaceutical preparation," or the like, generally refer to formulations that are adapted to deliver a prescribed dosage of one or more pharmacologically active compounds to a cell, a group of cells, an organ or tissue, an animal or a human. The determination of an appropriate prescribed dosage of a pharmacologically active compound to include in a pharmaceutical composition in order to achieve a desired biological outcome is within the skill level of an ordinary practitioner of the art. Pharmaceutical preparations may be prepared as solids, semi-solids, gels, hydrogels, liquids, solutions, suspensions, emulsions, aerosols, powders, or combinations thereof. Included in a pharmaceutical preparation may be one or more carriers, preservatives, flavorings, excipients, coatings, stabilizers, binders, solvents and/or auxiliaries. Methods of incorporating pharmacologically active compounds into pharmaceutical preparations are widely known in the art.

A "pharmaceutically acceptable formulation," as used herein, generally refers to a non-toxic formulation containing a predetermined dosage of a pharmaceutical composition, wherein the dosage of the pharmaceutical composition is adequate to achieve a desired biological outcome. A component of a pharmaceutically acceptable formulation may generally include an appropriate delivery vehicle that is suitable for the proper delivery of the pharmaceutical composition to achieve the desired biological outcome.

As used herein the term "antioxidant" may be generally refer to any one or more of various substances (as beta-carotene, vitamin C, and α-tocopherol) that inhibit oxidation or reactions promoted by Reactive Oxygen Species (ROS) and other radical and non-radical species.

As used herein the term "co-antioxidant" may be generally defined as an antioxidant that is used and that acts in combination with another antioxidant (e.g., two antioxidants that are chemically and/or functionally coupled, or two antioxidants that are combined and function with each another in a pharmaceutical preparation). The effects of co-antioxidants may be additive (i.e., the anti-oxidative potential of one or more anti-oxidants acting additively is approximately the sum of the oxidative potential of each component anti-oxidant) or synergistic (i.e., the anti-oxidative potential of one or more anti-oxidants acting synergistically may be greater than the sum of the oxidative potential of each component anti-oxidant).

Compounds described herein embrace isomers mixtures, racemic, optically active, and optically inactive stereoisomers and compounds.

Eicosanoids and Inflammation

Eicosanoids are a class of lipid-based hormones that are derived from the oxidation of polyunsaturated long chain fatty acids (e.g., linoleic and arachidonic acid). Arachidonic acid (AA), also known as arachidonate, is the most abundant and physiologically important eicosanoid precursor. The immediate cellular precursor to AA is linoleic acid (LA). Oxidation of AA by enzymes of cyclooxygenase (COX), lipoxygenase (LO) or cytochrome-P450 monooxygenase (CYP) families results in the formation of prostaglandins (PG), leukotrienes (LT) and epoxyeicosatrienoic acids (EETs), respectively. Eicosanoids may also arise through the non-enzymatic oxidation of AA. Exemplary though non-limiting eicosanoids arising through non-enzymatic oxidation of AA include the $F_2$-isoprostanoids (e.g. 8-iso-F2α) and 9-hydroxyeicosatetraenoic acid (HETE). Eicosanoids regulate many cellular functions and play crucial roles in a variety of physiological and pathophysiological processes, including for example regulation of smooth muscle contractility and various immune and inflammatory functions.

Leukotrienes and the 5-Lipoxygenase Pathway

The first step in the enzymatic synthesis of leukotrienes is catalyzed by LO enzymes. Mammals express a family of LO enzymes that catalyze the ultimate oxygenation of AA to leukotrienes at different sites. The products of LO catalysis have numerous important physiological functions.

The most widely studied leukotrienes are those whose production is acatalyzed by the 5-Lipoxygenase (5-LO) pathway. 5-LO is expressed in the cytosol of leukocytes, including basophils, Mast cells, eosinophils, monocytes and macrophages, where the enzyme catalyzes the conversion of arachidonate to 5-HPETE (5-hydroperoxyeicosatetraenoic acid). 5-HPETE is then converted to various leukotrienes that cause inflammation and asthmatic constriction of the bronchioles. Leukotrienes participate in numerous physiological processes, which may include host defense reactions and pathophysiological conditions such as immediate hypersensitivity and inflammation. Leukotrienes may have potent actions on many essential organs and systems, which may include the cardiovascular, pulmonary, and central nervous system as well as the gastrointestinal tract and the immune system.

The metabolism of AA by the enzymes 5-, 12-, and 15-LO results in the production of HPETEs, which may be converted to hydroxyl derivatives HETEs or LTs. The most widely investigated LO metabolites are the leukotrienes produced by 5-LO. 5-LO is an enzyme expressed in cells capable of eliciting inflammatory responses in mammals, such as polymorphonuclear (PMNs) cells, basophils, mast cells, eosinophils, monocytes/macrophages and epithelial cells. 5-LO requires the presence of the membrane protein 5-Lipoxygenase-activating protein (FLAP). FLAP binds AA, facilitating its interaction with the 5-LO. 5-LO, FLAP, and Phospholipase $A_2$ (which catalyzes release of arachidonate from phospholipids) form a complex in association with the nuclear envelope during leukotriene synthesis in leukocytes. The 5-LO pathway is of great clinical significance, since it may be associated with inflammatory disorders such as asthma or atherosclerosis. 5-LO oxidizes AA to form 5-hydroperoxyeicosatetraenoic acid (HPETE). 5-HPETE may then be further reduced to for 5-HETE or the intermediate leukotriene $LTA_4$. $LTA_4$ may then be catalyzed into the effector molecules $LTB_4$ through the action of a hydrolase, or to $LTC_4$, $LTD_4$, and $LTE_4$ through the action of glutathione-S-transferase, or acted on by other lipoxygenases to form lipoxins. The various LO pathways and leukotriene biosynthetic pathways are discussed in detail in Drazen et al., 1999 and Spector et al., 1988, both of which are incorporated by reference as though fully set forth herein. $LTB_4$ is a potent inducer of leukocyte chemotaxis and aggregation, vascular permeability, lymphocyte proliferation and the secretion of immuno-modulatory cytokines which may include interferon (IFN)-γ, inteleukin (IL)-1 and IL-2. $LTC_4$, $LTD_4$, and $LTE_4$ increase vascular permeability, are potent bronchoconstrictors and are components of the slow-reacting substance of anaphylaxis (SRS-A), which is secreted during asthmatic and anaphylactic episodes.

Because of the function of leukotrienes as proinflammatory hormones, it may be desirable to develop anti-leukotriene therapies as potential treatments for maladies that may be in part attributable to the induction of an inflammatory response, such as asthma or atherosclerosis. Strategies to reduce the biological availability of leukotrienes may include the development of 5-lipoxygenase inhibitors, leukotrienene receptor antagonists, inhibitors of FLAP, or inhibitors of phospholipase-$A_2$, which catalyzes the production of AA.

Anti-leukotriene therapies may include therapies that modulate 5-LO function. As used herein therapies that "modulate 5-LO function" may include for example therapies that modulate 5-LO enzyme activity, 5-LO expression, 5-LO stability, 5-LO cellular localization, and/or any other means of controlling the biological activity of the 5-LO pathway in vivo such that the biological availability of metabolized synthesized by 5-LO catalysis is at least partially reduced.

In some embodiments, administration of analogs or derivatives of carotenoids embodied herein to a subject may reduce the severity of an inflammatory response. In an embodiment, administering the analogs or derivatives of carotenoids embodied herein to a subject may reduce the severity of an asthmatic episode in a subject. In an embodiment, administering the analogs or derivatives of carotenoids embodied herein to a subject may reduce the severity of atherosclerosis in a subject. In an embodiment, administering the analogs or derivatives of carotenoids embodied herein to a subject may control the biological availability of arachidonic acid, linoleic acid and/or eicosanoids that are synthesized therefrom. In an embodiment, administering the analogs or derivatives of carotenoids embodied herein to a subject may substantially reduce the biological availability of 5-lipoxygenase (5-LO)-catalyzed eicosanoids including, but not limited to, leukotrienes (LTs)-$A_4$, $B_4$, $C_4$, $D_4$ and $E_4$, and/or other eicosanoids that result from 5-LO catalytic activity.

In some embodiments, carotenoid analogs or derivatives may be employed in "self-formulating" aqueous solutions, in which the compounds spontaneously self-assemble into macromolecular complexes. These complexes may provide stable formulations in terms of shelf life. The same formulations may be parenterally administered, upon which the spontaneous self-assembly is overcome by interactions with serum and/or tissue components in vivo.

Some specific embodiments may include phosphate derivatives, succinate derivatives, co-antioxidant derivatives (e.g., Vitamin C, Vitamin C analogs, Vitamin C derivatives, Vitamin E, Vitamin E analogs, Vitamin E derivatives, flavonoids, flavonoid analogs, or flavonoid derivatives), or combinations thereof derivatives or analogs of carotenoids. Flavonoids may include, for example, quercetin, xanthohumol, isoxanthohumol, or genistein. Derivatives or analogs may be derived from any known carotenoid (naturally or synthetically derived). Specific examples of naturally occurring carotenoids which compounds described herein may be derived from include for example zeaxanthin, lutein, lycophyll, astaxanthin, and lycopene.

In some embodiments, one or more co-antioxidants may be coupled to a carotenoid or carotenoid derivative or analog.

The synthesis of water-soluble and/or water-dispersible carotenoids (e.g., C40) analogs or derivatives—as potential parenteral agents for clinical applications may improve the injectability of these compounds as therapeutic agents, a result perhaps not achievable through other formulation methods. The methodology may be extended to carotenoids with fewer than 40 carbon atoms in the molecular skeleton and differing ionic character. The methodology may be extended to carotenoids with greater than 40 carbon atoms in the molecular skeleton. The methodology may be extended to non-symmetric carotenoids. The aqueous dispersibility of these compounds allows proof-of-concept studies in model systems (e.g. cell culture), where the high lipophilicity of these compounds previously limited their bioavailability and hence proper evaluation of efficacy. Esterification or etherification may be useful to increase oral bioavailability, a fortuitous side effect of the esterification process, which can increase solubility in gastric mixed micelles. The net overall effect is an improvement in potential clinical utility for the lipophilic carotenoid compounds as therapeutic agents.

In some embodiments, the principles of retrometabolic drug design may be utilized to produce novel soft drugs from the asymmetric parent carotenoid scaffold (e.g., RRR-lutein (β,ε-carotene-3,3'-diol)). For example, lutein scaffold for derivatization was obtained commercially as purified natural plant source material, and was primarily the RRR-stereoisomer (one of 8 potential stereoisomers). Lutein (Scheme 1) possesses key characteristics—similar to starting material astaxanthin—which make it an ideal starting platform for retrometabolic syntheses: (1) synthetic handles (hydroxyl groups) for conjugation, and (2) an excellent safety profile for the parent compound. As stated above, lutein is available commercially from multiple sources in bulk as primarily the RRR-stereoisomer, the primary isomer in the human diet and human retinal tissue.

In some embodiments, carotenoid analogs or derivatives may have increased water solubility and/or water dispersibility relative to some or all known naturally occurring carotenoids. Contradictory to previous research, improved results are obtained with derivatized carotenoids relative to the base carotenoid, wherein the base carotenoid is derivatized with substituents including hydrophilic substituents and/or co-antioxidants.

In some embodiments, the carotenoid derivatives may include compounds having a structure including a polyene chain (i.e., backbone of the molecule). The polyene chain may include between about 5 and about 15 unsaturated bonds. In certain embodiments, the polyene chain may include between about 7 and about 12 unsaturated bonds. In some embodiments a carotenoid derivative may include 7 or more conjugated double bonds to achieve acceptable antioxidant properties.

In some embodiments, decreased antioxidant properties associated with shorter polyene chains may be overcome by increasing the dosage administered to a subject or patient.

In some embodiments, a chemical compound including a carotenoid derivative or analog may have the general structure (126):

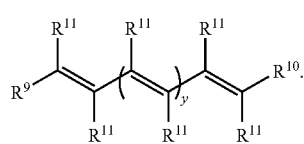

(126)

Each $R^{11}$ may be independently hydrogen or methyl. $R^9$ and $R^{10}$ may be independently H, an acyclic alkene with one or more substituents, or a cyclic ring including one or more substituents. y may be 5 to 12. In some embodiments, y may be 3 to 15. In certain embodiments, the maximum value of y may only be limited by the ultimate size of the chemical compound, particularly as it relates to the size of the chemical compound and the potential interference with the chemical compound's biological availability as discussed herein. In some embodiments, substituents may be at least partially hydrophilic. These carotenoid derivatives may be included in a pharmaceutical composition.

In some embodiments, the carotenoid derivatives may include compounds having the structure (128):

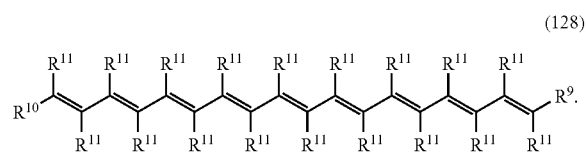

(128)

Each $R^{11}$ may be independently hydrogen, methyl, alkyl, alkenyl, or aromatic substituents. $R^9$ and $R^{10}$ may be independently H, an acyclic alkene with at least one substituent, or a cyclic ring with at least one substituent having general structure (130):

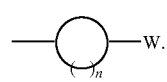

(130)

where n may be between 4 to 10 carbon atoms. W is the substituent.

In some embodiments, each cyclic ring may be independently two or more rings fused together to form a fused ring system (e.g., a bi-cyclic system). Each ring of the fused ring system may independently contain one or more degrees of unsaturation. Each ring of the fused ring system may be independently aromatic. Two or more of the rings forming the fused ring system may form an aromatic system.

In some embodiments, a chemical composition may include a carotenoid derivative having the structure

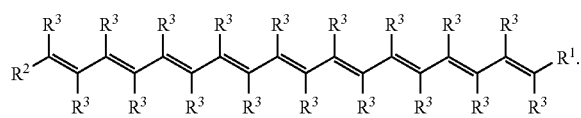

Each $R^3$ may be independently hydrogen or methyl. $R^1$ and $R^2$ may be a cyclic ring including at least one substituent. Each cyclic ring may be independently:

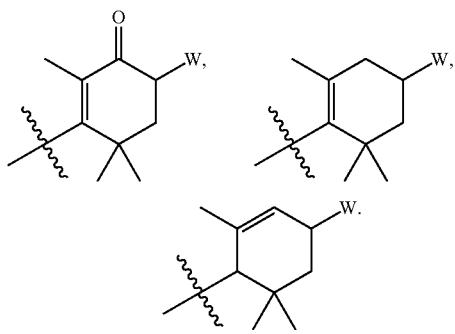

W is the substituent. In some embodiments $R^1$ and $R^2$ may be an acyclic group including at least one substituent. Each acyclic may be:

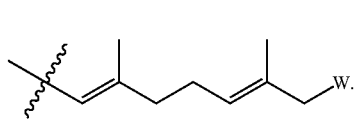

In some embodiments, a chemical composition may include a carotenoid derivative having the structure

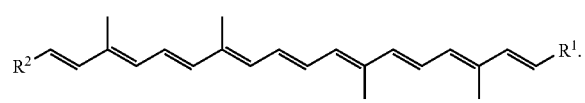

$R^1$ and $R^2$ may be a cyclic ring including at least one substituent. Each cyclic ring may be independently:

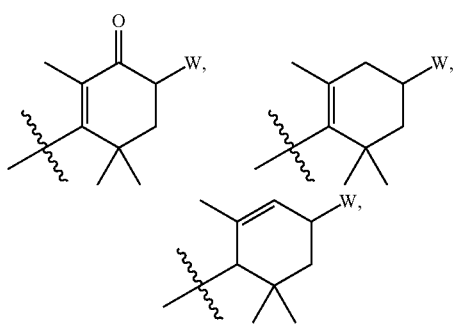

where W is the substituent. In some embodiments $R^1$ and $R^2$ may be an acyclic group including at least one substituent. Each acyclic group may be:

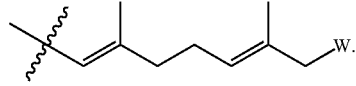

In some embodiments, a method of treating a proliferative disorder may include administering to the subject an effective amount of a pharmaceutically acceptable formulation including a synthetic analog or derivative of a carotenoid. The synthetic analog or derivative of the carotenoid may have the structure

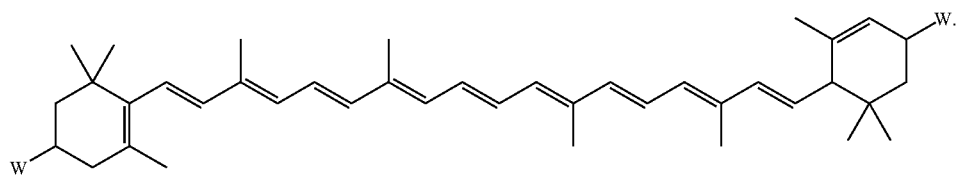

At least one substituent W may independently include

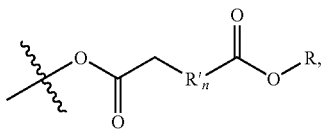 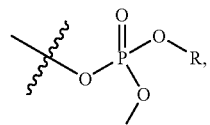

or a co-antioxidant. Each R' may be $CH_2$. n may range from 1 to 9. Each R may be independently H, alkyl, aryl, benzyl, Group IA metal, or a co-antioxidant. Each co-antioxidant may be independently Vitamin C, Vitamin C analogs, Vitamin C derivatives, Vitamin E, Vitamin E analogs, Vitamin E derivatives, flavonoids, flavonoid analogs, or flavonoid derivatives. Flavonoids may include, for example, quercetin, xanthohumol, isoxanthohumol, or genistein.

Vitamin E may generally be divided into two categories including tocopherols having a general structure

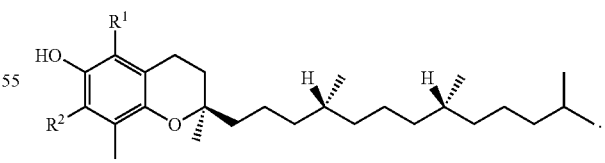

Alpha-tocopherol is used to designate when $R^1=R^2=CH_3$. Beta-tocopherol is used to designate when $R^1=CH_3$ and $R^2=H$. Gamma-tocopherol is used to designate when $R^1=H$ and $R^2=CH_3$. Delta-tocopherol is used to designate when $R^1=R^2=H$.

The second category of Vitamin E may include tocotrienols having a general structure

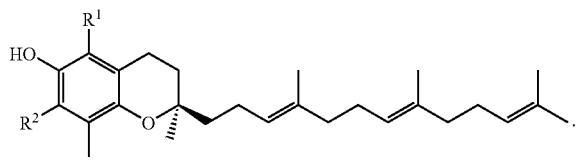

Alpha-tocotrienol is used to designate when $R^1=R^2=CH_3$. Beta-tocotrienol is used to designate when $R^1=CH_3$ and $R^2=H$. Gamma—tocotrienol is used to designate when $R^1=H$ and $R^2=CH_3$. Delta—tocotrienol is used to designate when $R^1=R^2=H$.

Quercetin, a flavonoid, may have the structure

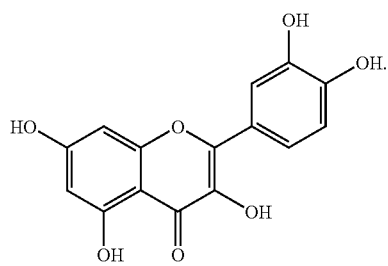

In some embodiments, the carotenoid analog or derivative may have the structure

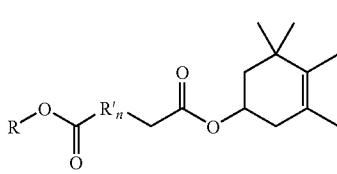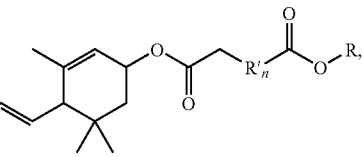

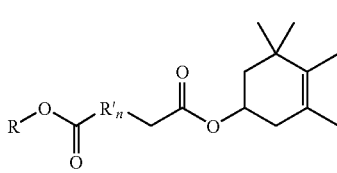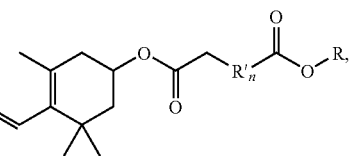

or

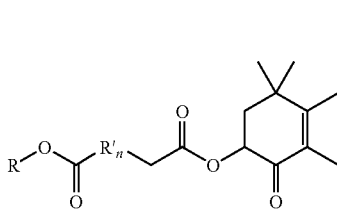

Each R may be independently H, alkyl, aryl, benzyl, Group IA metal, or a co-antioxidant. Each co-antioxidant may be independently Vitamin C, Vitamin C analogs, Vitamin C derivatives, Vitamin E, Vitamin E analogs, Vitamin E derivatives, flavonoids, flavonoid analogs, or flavonoid derivatives. Flavonoids may include, for example, quercetin, xanthohumol, isoxanthohumol, or genistein.

In some embodiments, the carotenoid analog or derivative may have the structure

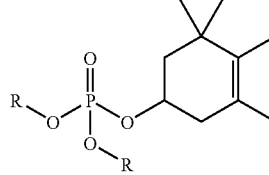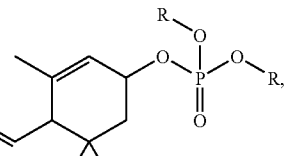

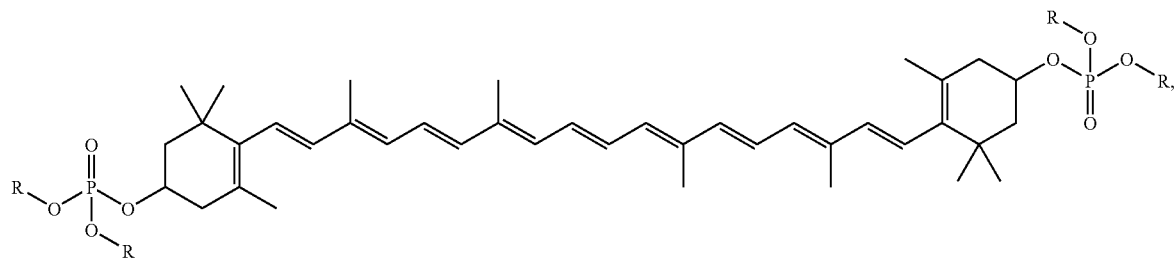

or

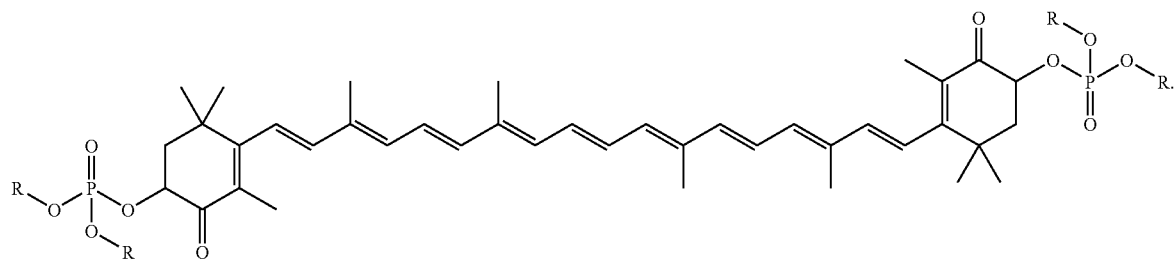

Each R may be independently H, alkyl, aryl, benzyl, Group IA metal (e.g., sodium), or a co-antioxidant. Each co-antioxidant may be independently Vitamin C, Vitamin C analogs, Vitamin C derivatives, Vitamin E, Vitamin E analogs, Vitamin E derivatives, flavonoids, flavonoid analogs, or flavonoid derivatives. Flavonoids may include, for example, quercetin, xanthohumol, isoxanthohumol, or genistein. When R includes Vitamin C, Vitamin C analogs, or Vitamin C derivatives, some embodiments may include carotenoid analogs or derivatives having the structure

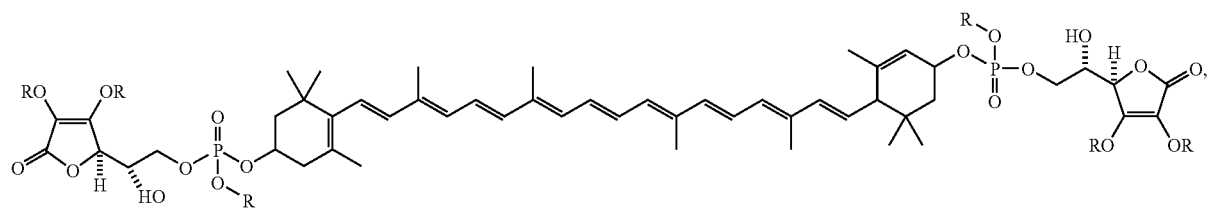

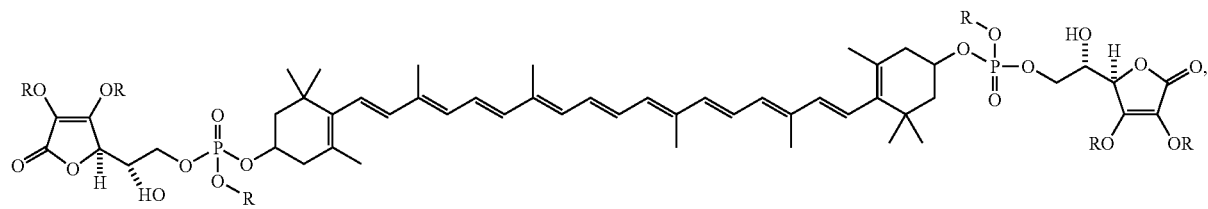

or

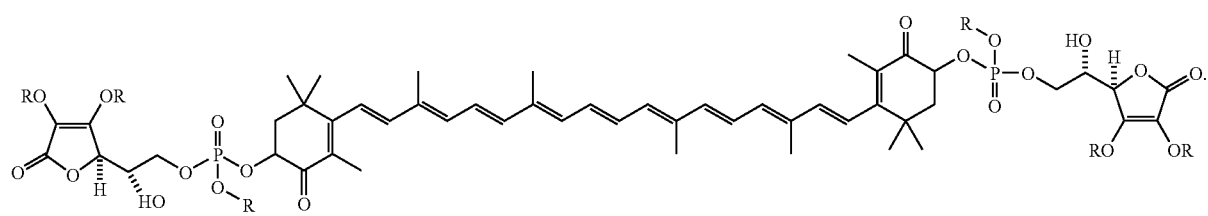

Each R may be independently H, alkyl, aryl, benzyl, or Group IA metal.

In some embodiments, a chemical compound including a carotenoid derivative may have the general structure (132):

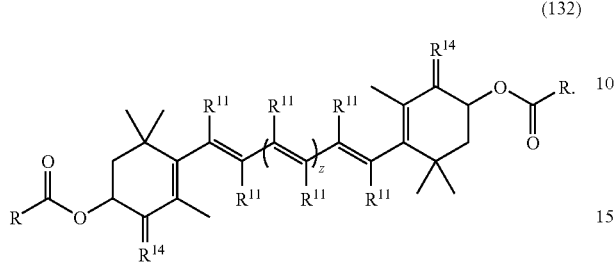

(132)

Each $R^{11}$ may be independently hydrogen or methyl. Each $R^{14}$ may be independently O or $H_2$. Each R may be independently $OR^{12}$ or $R^{12}$. Each $R^{12}$ may be independently -alkyl-$NR^{13}_3{}^+$, -aromatic-$NR^{13}_3{}^+$, -alkyl-$CO_2{}^-$, -aromatic-$CO_2{}^-$, -amino acid-$NH_3{}^+$, -phosphorylated amino acid-$NH_3{}^+$, polyethylene glycol, dextran, H, alkyl, co-antioxidant (e.g. Vitamin C, Vitamin C analogs, Vitamin C derivatives, Vitamin E, Vitamin E analogs, Vitamin E derivatives, flavonoids, flavonoid analogs, or flavonoid derivatives), or aryl. Each $R^{13}$ may be independently H, alkyl, or aryl. z may range from 5 to 12. In some embodiments, z may range from about 3 to about 15. In certain embodiments, the maximum value of z may only be limited by the ultimate size of the chemical compound, particularly as it relates to the size of the chemical compound and the potential interference with the chemical compound's biological availability as discussed herein. In some embodiments, substituents may be at least partially hydrophilic. These carotenoid derivatives may be used in a pharmaceutical composition.

In some embodiments, a chemical compound including a carotenoid derivative may have the general structure (134):

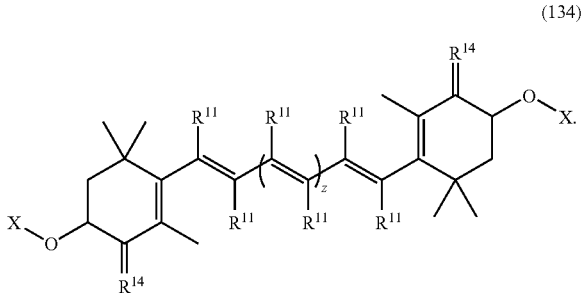

(134)

Each $R^{11}$ may be independently hydrogen or methyl. Each $R^{14}$ may be independently O or $H_2$. Each X may be independently

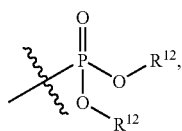  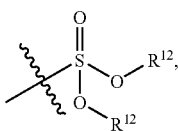

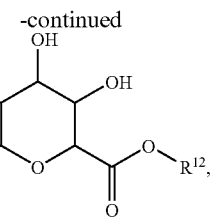

-alkyl-$NR^{12}_3{}^+$, -aromatic-$NR^{12}_3{}^+$, -alkyl-$CO_2{}^-$, -aromatic-$CO_2{}^-$, -amino acid-$NH_3{}^+$, -phosphorylated amino acid-$NH_3{}^+$, polyethylene glycol, dextran, alkyl, Group IA metal, co-antioxidant (e.g. Vitamin C, Vitamin C analogs, Vitamin C derivatives, Vitamin E, Vitamin E analogs, Vitamin E derivatives, flavonoids, flavonoid analogs, or flavonoid derivatives), or aryl. Each $R^{12}$ is independently -alkyl-N $R^{13}_3{}^+$, -aromatic-$NR^{13}_3{}^+$, -alkyl-$CO_2{}^-$, -aromatic-$CO_2{}^-$, -amino acid-$NH_3{}^+$, -phosphorylated amino acid-$NH_3{}^+$, polyethylene glycol, dextran, H, alkyl, aryl, benzyl, Group IA metal, co-antioxidant (e.g. Vitamin C, Vitamin C analogs, Vitamin C derivatives, Vitamin E, Vitamin E analogs, Vitamin E derivatives, flavonoids, flavonoid analogs, or flavonoid derivatives), or Group IA salt. Each $R^{13}$ may be independently H, alkyl, or aryl. z may range from 5 to 12. In some embodiments, z may range from about 3 to about 15. In certain embodiments, the maximum value of z may only be limited by the ultimate size of the chemical compound, particularly as it relates to the size of the chemical compound and the potential interference with the chemical compound's biological availability as discussed herein. In some embodiments, substituents may be at least partially hydrophilic. These carotenoid derivatives may be used in a pharmaceutical composition.

In some non-limiting examples, five- and/or six-membered ring carotenoid derivatives may be more easily synthesized. Synthesis may come more easily due to, for example, the natural stability of five- and six-membered rings. Synthesis of carotenoid derivatives including five- and/or six-membered rings may be more easily synthesized due to, for example, the availability of naturally occurring carotenoids including five- and/or six-membered rings. In some embodiments, five-membered rings may decrease steric hindrance associated with rotation of the cyclic ring around the molecular bond connecting the cyclic ring to the polyene chain. Reducing steric hindrance may allow greater overlap of any π oribitals within a cyclic ring with the polyene chain, thereby increasing the degree of conjugation and effective chromophore length of the molecule. This may have the salutatory effect of increasing antioxidant capacity of the carotenoid derivatives.

In some embodiments, a substituent (W) may be at least partially hydrophilic. A hydrophilic substituent may assist in increasing the water solubility of a carotenoid derivative. In some embodiments, a carotenoid derivative may be at least partially water-soluble. The cyclic ring may include at least one chiral center. The acyclic alkene may include at least one chiral center. The cyclic ring may include at least one degree of unsaturation. In some cyclic ring embodiments, the cyclic ring may be aromatic. One or more degrees of unsaturation within the ring may assist in extending the conjugation of the carotenoid derivative. Extending conjugation within the carotenoid derivative may have the salutatory effect of increasing the antioxidant properties of the carotenoid derivatives. In some embodiments, the substituent W may include, for example, a carboxylic acid, an amino acid, an ester, an alkanol, an amine, a phosphate, a succinate, a glycinate, an ether, a glucoside, a sugar, or a carboxylate salt.

In some embodiments, each substituent —W may independently include —XR. Each X may independently include O, N, or S. In some embodiments, each substituent —W may independently comprise amino acids, esters, carbamates, amides, carbonates, alcohol, phosphates, or sulfonates. In some substituent embodiments, the substituent may include, for example (d) through (uu):

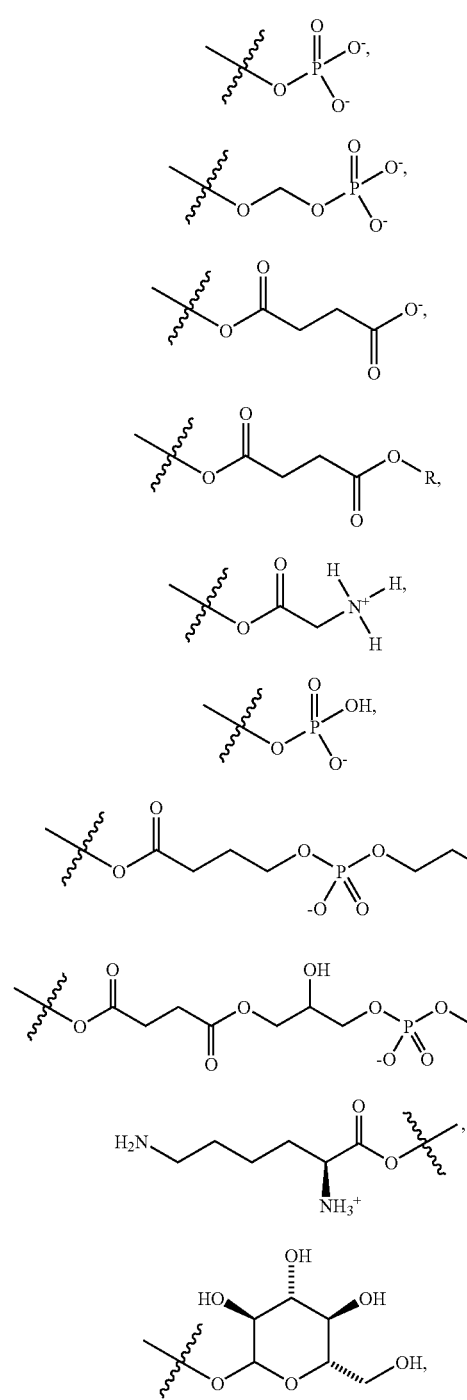

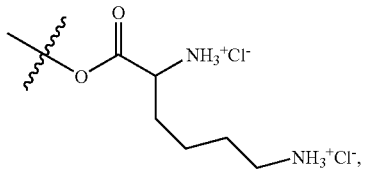

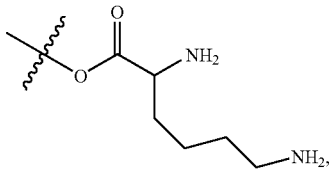

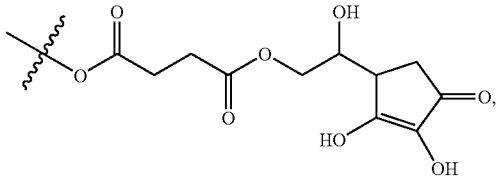

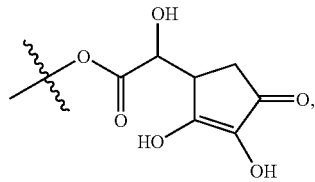

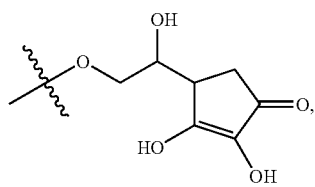

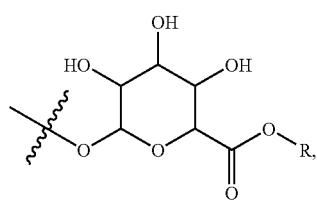

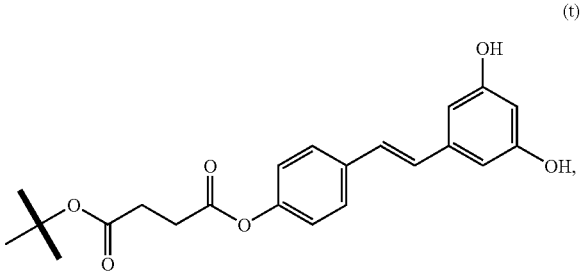

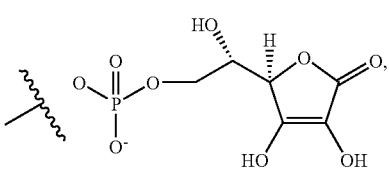

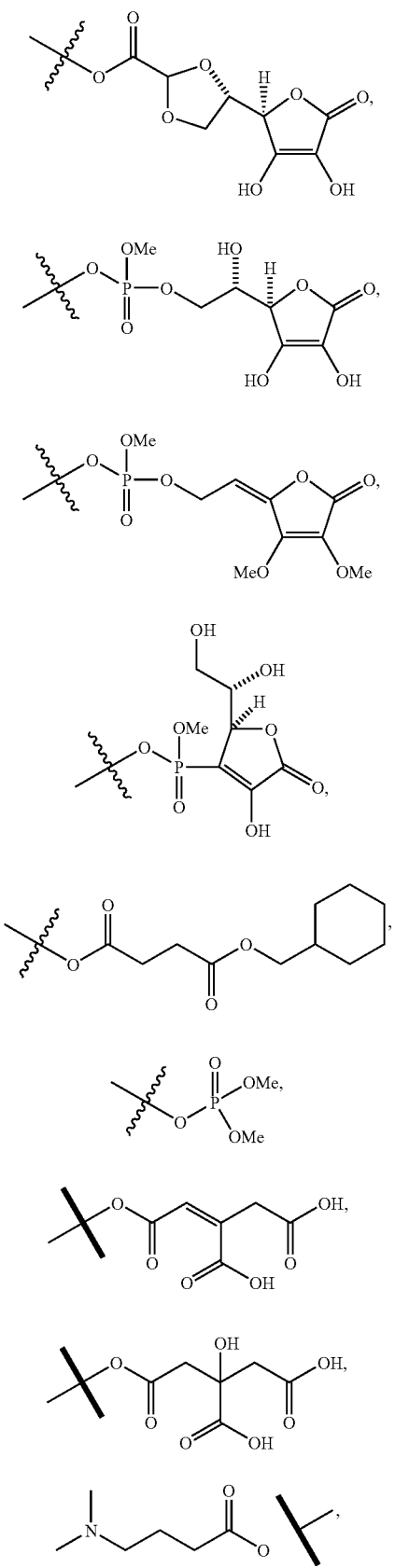
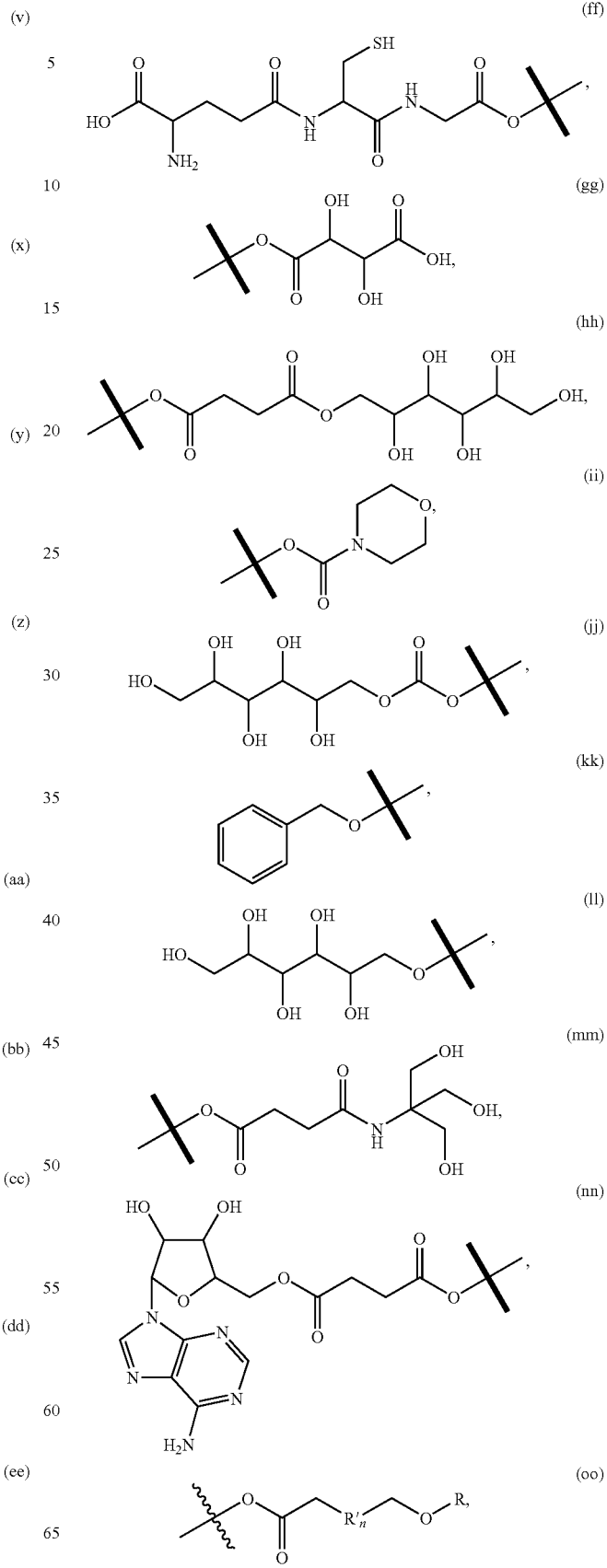

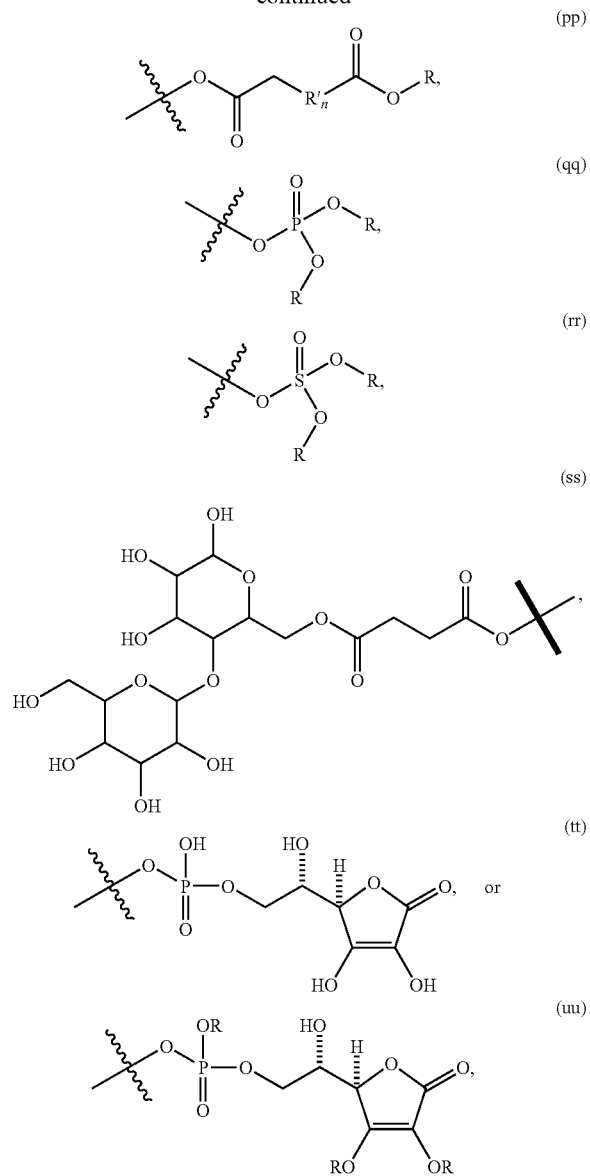

where each R is, for example, independently -alkyl-$NR^{12}_3{}^+$, -aromatic-$NR^{12}_3{}^+$, -alkyl-$CO_2{}^-$, -aromatic-$CO_2{}^-$, -amino acid-$NH_3{}^+$, -phosphorylated amino acid-$NH_3{}^+$, polyethylene glycol, dextran, H, alkyl, Group IA metal, co-antioxidant (e.g. Vitamin C, Vitamin C analogs, Vitamin C derivatives, Vitamin E, Vitamin E analogs, Vitamin E derivatives, flavonoids, flavonoid analogs, or flavonoid derivatives), or aryl. Each R' may be $CH_2$. n may range from 1 to 9. In some embodiments, substituents may include any combination of (d) through (uu). In some embodiments, negatively charged substituents may include Group IA metals, one metal or a combination of different Group IA metals in an embodiment with more than one negatively charged substituent, as counter ions. Group IA metals may include, but are not limited to, sodium, potassium, and/or lithium.

Water-soluble carotenoid analogs or derivatives may have a water solubility of greater than about 1 mg/mL in some embodiments. In certain embodiments, water-soluble carotenoid analogs or derivatives may have a water solubility of greater than about 5 mg/mL. In certain embodiments, water-soluble carotenoid analogs or derivatives may have a water solubility of greater than about 10 mg/mL. In certain embodiments, water-soluble carotenoid analogs or derivatives may have a water solubility of greater than about 20 mg/mL. In some embodiments, water-soluble carotenoid analogs or derivatives may have a water solubility of greater than about 50 mg/mL.

Naturally occurring carotenoids such as xanthophyll carotenoids of the C40 series, which includes commercially important compounds such as lutein, zeaxanthin, and astaxanthin, have poor aqueous solubility in the native state. Varying the chemical structure(s) of the esterified moieties may vastly increase the aqueous solubility and/or dispersibility of derivatized carotenoids.

In some embodiments, highly water-dispersible C40 carotenoid derivatives may include natural source RRR-lutein (β,ε-carotene-3,3'-diol) derivatives. Derivatives may be synthesized by esterification with inorganic phosphate and succinic acid, respectively, and subsequently converted to the sodium salts. Deep orange, evenly colored aqueous suspensions were obtained after addition of these derivatives to USP-purified water. Aqueous dispersibility of the disuccinate sodium salt of natural lutein was 2.85 mg/mL; the diphosphate salt demonstrated a >10-fold increase in dispersibility at 29.27 mg/mL. Aqueous suspensions may be obtained without the addition of heat, detergents, co-solvents, or other additives.

The direct aqueous superoxide scavenging abilities of these derivatives were subsequently evaluated by electron paramagnetic resonance (EPR) spectroscopy in a well-characterized in vitro isolated human neutrophil assay. The derivatives may be potent (millimolar concentration) and nearly identical aqueous-phase scavengers, demonstrating dose-dependent suppression of the superoxide anion signal (as detected by spin-trap adducts of DEPMPO) in the millimolar range. Evidence of card-pack aggregation was obtained for the diphosphate derivative with UV-Vis spectroscopy (discussed herein), whereas limited card-pack and/or head-to-tail aggregation was noted for the disuccinate derivative. These lutein-based soft drugs may find utility in those commercial and clinical applications for which aqueous-phase singlet oxygen quenching and direct radical scavenging may be required.

The absolute size of a carotenoid derivative (in 3 dimensions) is important when considering its use in biological and/or medicinal applications. Some of the largest naturally occurring carotenoids are no greater than about $C_{50}$. This is probably due to size limits imposed on molecules requiring incorporation into and/or interaction with cellular membranes. Cellular membranes may be particularly co-evolved with molecules of a length of approximately 30 nm. In some embodiments, carotenoid derivatives may be greater than or less than about 30 nm in size. In certain embodiments, carotenoid derivatives may be able to change conformation and/or otherwise assume an appropriate shape, which effectively enables the carotenoid derivative to efficiently interact with a cellular membrane.

Although the above structure, and subsequent structures, depict alkenes in the E configuration this should not be seen as limiting. Compounds discussed herein may include embodiments where alkenes are in the Z configuration or include alkenes in a combination of Z and E configurations within the same molecule. The compounds depicted herein may naturally convert between the Z and E configuration and/or exist in equilibrium between the two configurations.

In an embodiment, a chemical compound may include a carotenoid derivative having the structure (136)

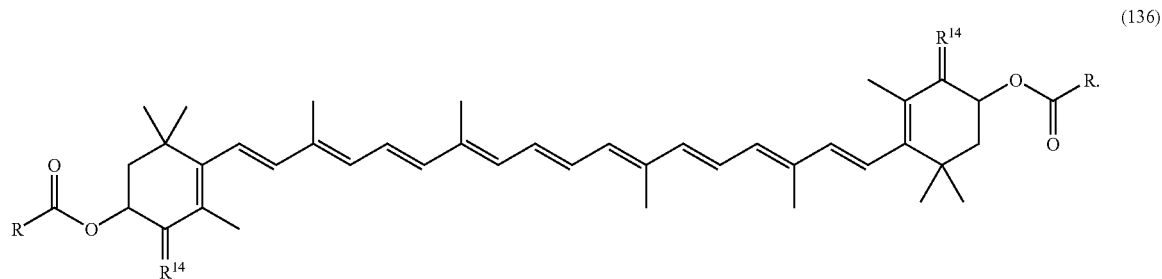

(136)

Each $R^{14}$ may be independently O or $H_2$. Each R may be independently $OR^{12}$ or $R^{12}$. Each $R^{12}$ may be independently -alkyl-$NR^{13}_3{}^+$, -aromatic-$NR^{13}_3{}^+$, -alkyl-$CO_2{}^-$, -aromatic-$CO_2{}^-$, -amino acid-$NH_3{}^+$, -phosphorylated amino acid-$NH_3{}^+$, polyethylene glycol, dextran, H, alkyl, peptides, polylysine, co-antioxidant (e.g. Vitamin C, Vitamin C analogs, Vitamin C derivatives, Vitamin E, Vitamin E analogs, Vitamin E derivatives, flavonoids, flavonoid analogs, or flavonoid derivatives), or aryl. In addition, each $R^{13}$ may be independently H, alkyl, or aryl. The carotenoid derivative may include at least one chiral center.

In a specific embodiment where $R^{14}$ is $H_2$, the carotenoid derivative may have the structure (138)

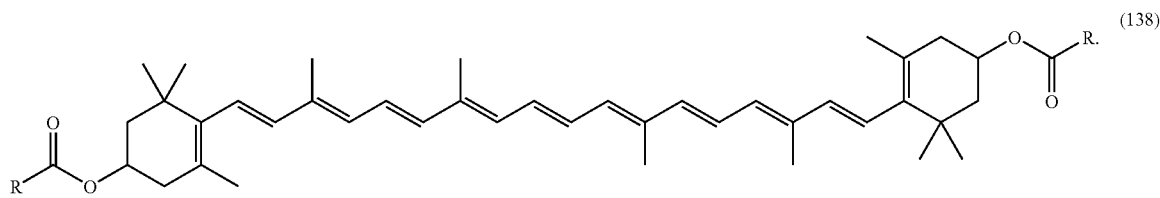

(138)

In a specific embodiment where $R^{14}$ is O, the carotenoid derivative may have the structure (140)

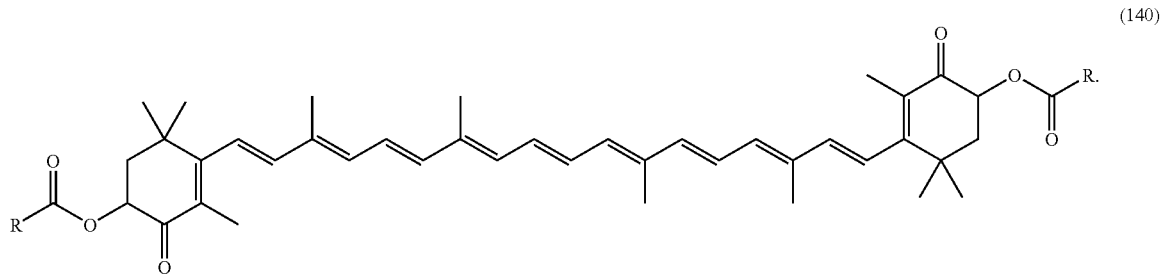

(140)

In an embodiment, a chemical compound may include a carotenoid derivative having the structure (142)

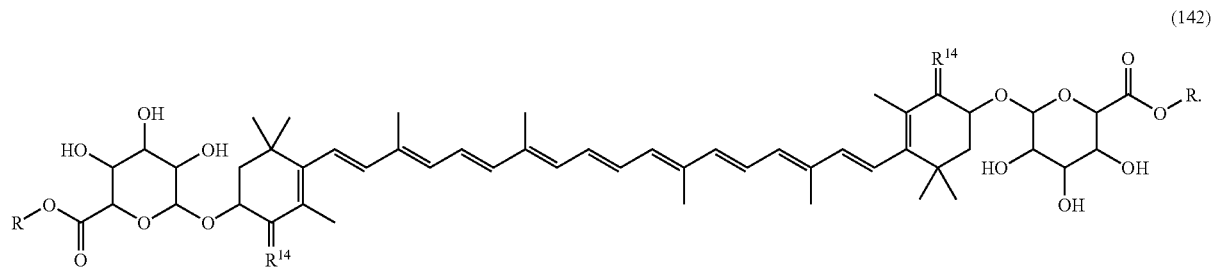

(142)

Each $R^{14}$ may be independently O or $H_2$. Each R may be independently H, alkyl, benzyl, Group IA metal, co-antioxidant, or aryl. The carotenoid derivative may include at least one chiral center. In a specific embodiment $R^{14}$ may be $H_2$, the carotenoid derivative having the structure (144)

Group IA metal, or co-antioxidant (e.g. Vitamin C, Vitamin C analogs, Vitamin C derivatives, Vitamin E, Vitamin E analogs, Vitamin E derivatives, flavonoids, flavonoid analogs, or flavonoid derivatives). Each R may be independently -alkyl- (144)

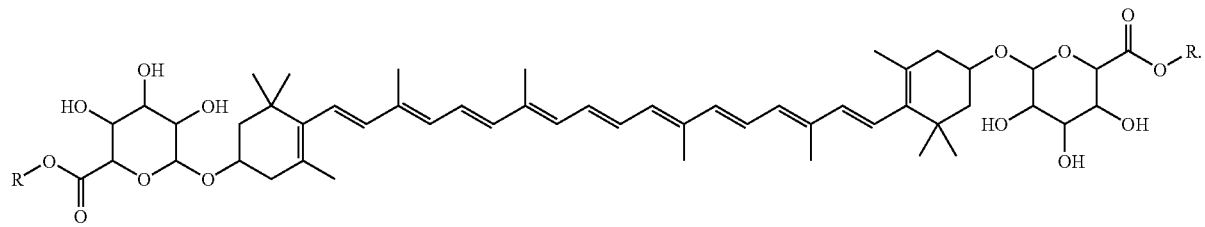

In a specific embodiment where $R^{14}$ is O, the carotenoid derivative may have the structure (146)

(146)

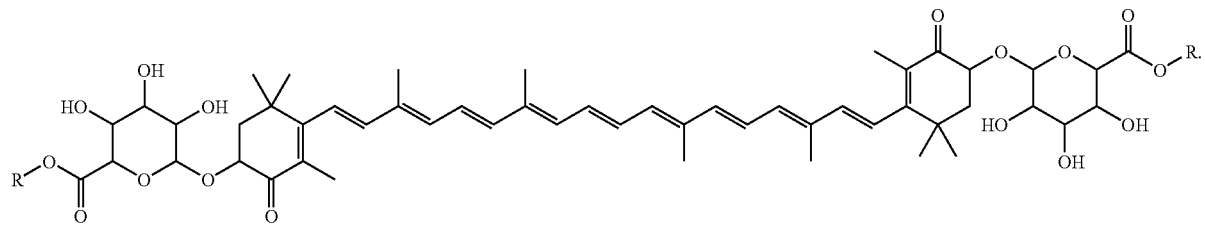

In an embodiment, a chemical compound may include a carotenoid derivative having the structure (148)

(148)

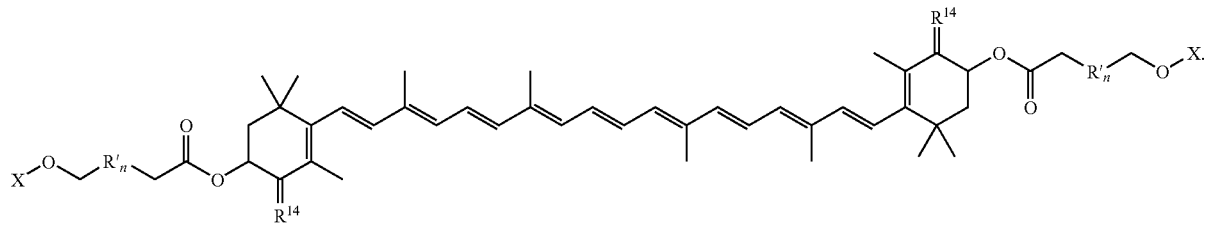

Each $R^{14}$ may be independently O or $H_2$. Each R' may be $CH_2$. n may range from 1 to 9. Each X may be independently

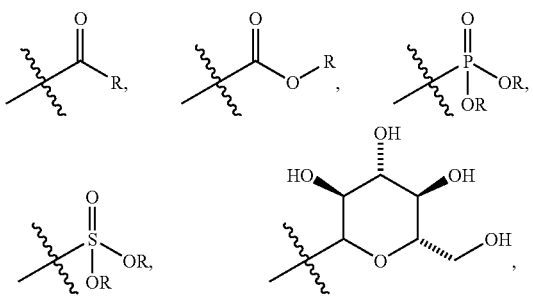

$NR^{12}{}_3{}^+$, -aromatic-$NR^{12}{}_3{}^+$, -alkyl-$CO_2{}^-$, -aromatic-$CO_2{}^-$, -amino acid-$NH_3{}^+$, -phosphorylated amino acid-$NH_3{}^+$, polyethylene glycol, dextran, H, alkyl, Group IA metal, benzyl, co-antioxidant (e.g. Vitamin C, Vitamin C analogs, Vitamin C derivatives, Vitamin E, Vitamin E analogs, Vitamin E derivatives, flavonoids, flavonoid analogs, or flavonoid derivatives), or aryl. Each $R^{12}$ may be independently H, alkyl, or aryl. The carotenoid derivative may include at least one chiral center.

In a specific embodiment where $R^{14}$ is $H_2$, the carotenoid derivative may have the structure (150)

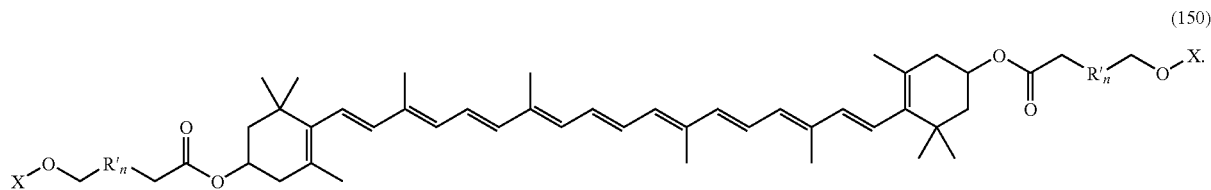

(150)

In a specific embodiment where $R^{14}$ is O, the carotenoid derivative may have the structure (152)

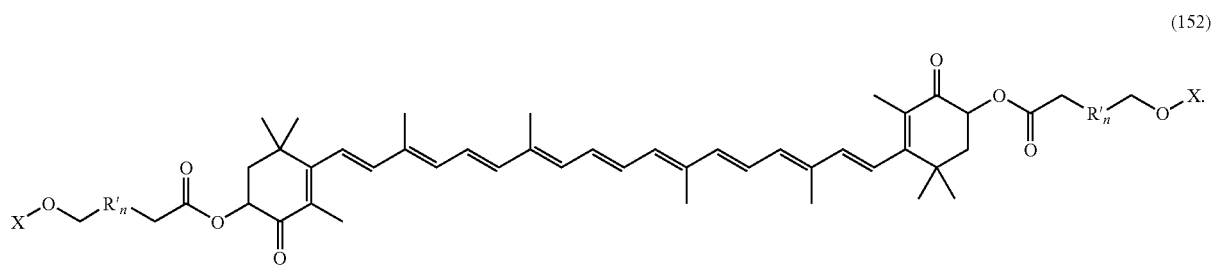

(152)

In an embodiment, a chemical compound may include a carotenoid derivative having the structure (148)

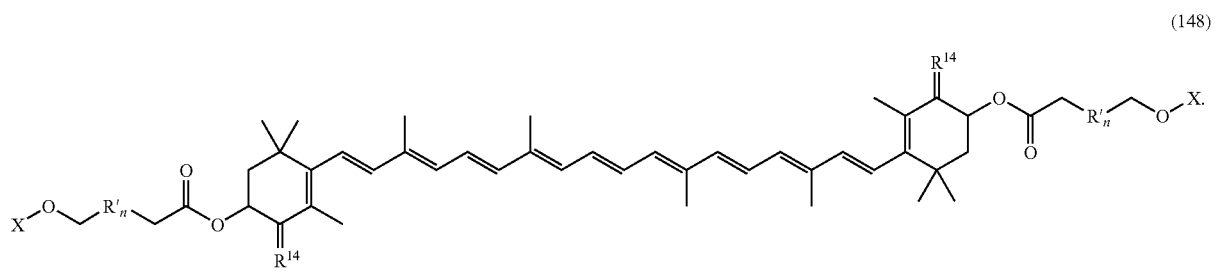

(148)

Each $R^{14}$ may be independently O or $H_2$. Each R' may be $CH_2$. n may range from 1 to 9. Each X may be independently

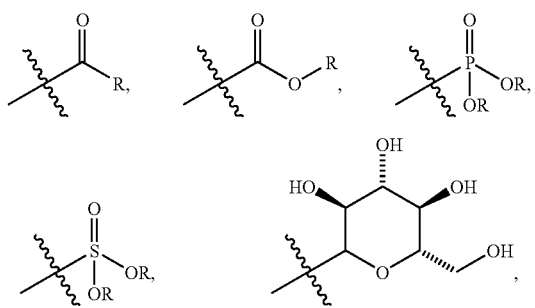

Group IA metal, or co-antioxidant (e.g. Vitamin C, Vitamin C analogs, Vitamin C derivatives, Vitamin E, Vitamin E analogs, Vitamin E derivatives, flavonoids, flavonoid analogs, or flavonoid derivatives). Each R may be independently -alkyl-$NR^{12}{}_3{}^+$, -aromatic-$NR^{12}{}_3{}^+$, -alkyl-$CO_2{}^-$, -aromatic-$CO_2{}^-$, -amino acid-$NH_3{}^+$, -phosphorylated amino acid-$NH_3{}^+$, polyethylene glycol, dextran, H, alkyl, Group IA metal, co-antioxidant (e.g. Vitamin C, Vitamin C analogs, Vitamin C derivatives, Vitamin E, Vitamin E analogs, Vitamin E derivatives, flavonoids, flavonoid analogs, or flavonoid derivatives), or aryl. Each $R^{12}$ may be independently H, alkyl, or aryl. The carotenoid derivative may include at least one chiral center.

In a specific embodiment where $R^{14}$ is $H_2$, the carotenoid derivative may have the structure (150)

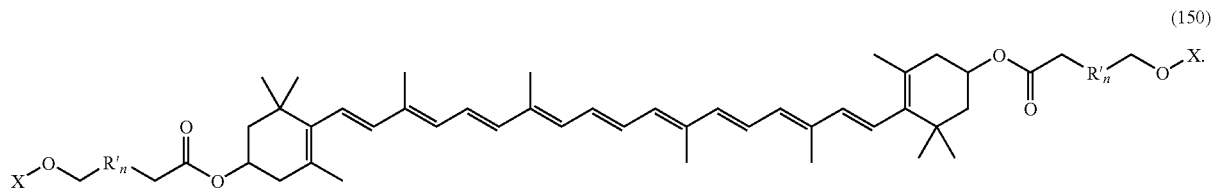

(150)

In a specific embodiment where $R^{14}$ is O, the carotenoid derivative may have the structure (152)

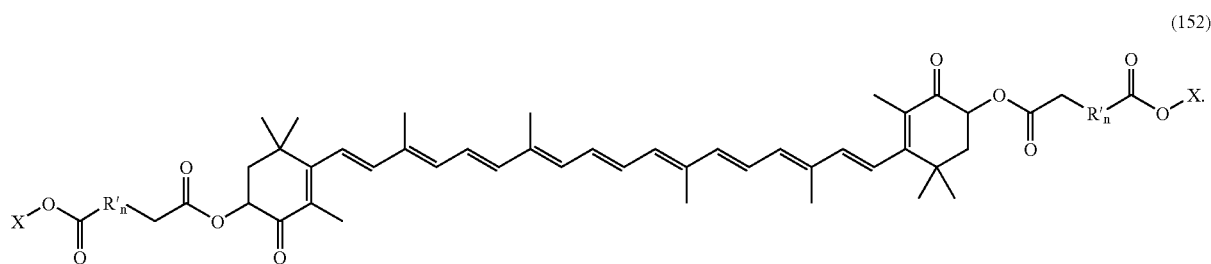

(152)

In an embodiment, a chemical compound may include a carotenoid derivative having the structure (154)

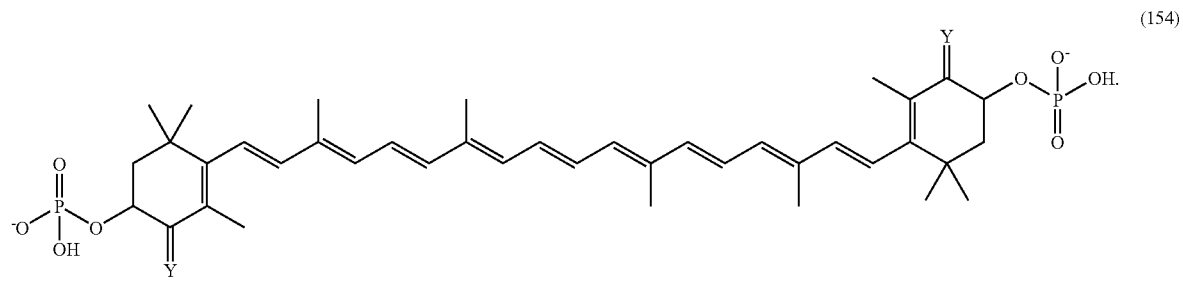

(154)

Each $R^{14}$ may be independently O or $H_2$. The carotenoid derivative may include at least one chiral center. In a specific embodiment $R^{14}$ may be $H_2$, the carotenoid derivative having the structure (156)

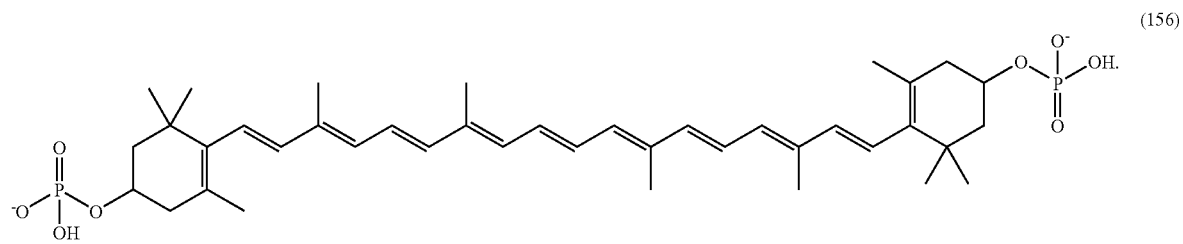

(156)

In a specific embodiment where $R^{14}$ is O, the carotenoid derivative may have the structure (158)

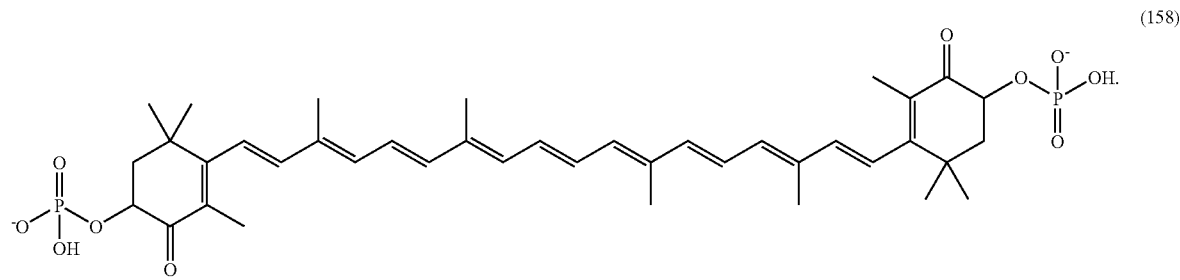

(158)

In some embodiments, a chemical compound may include a disuccinic acid ester carotenoid derivative having the structure (160)

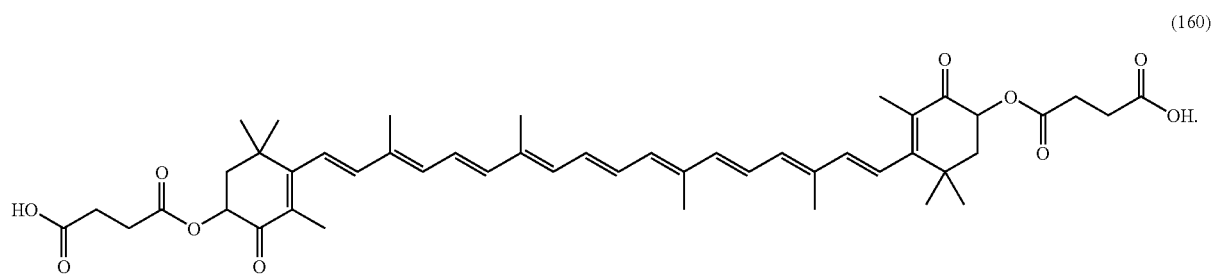

(160)

In some embodiments, a chemical compound may include a disodium salt disuccinic acid ester carotenoid derivative having the structure (162)

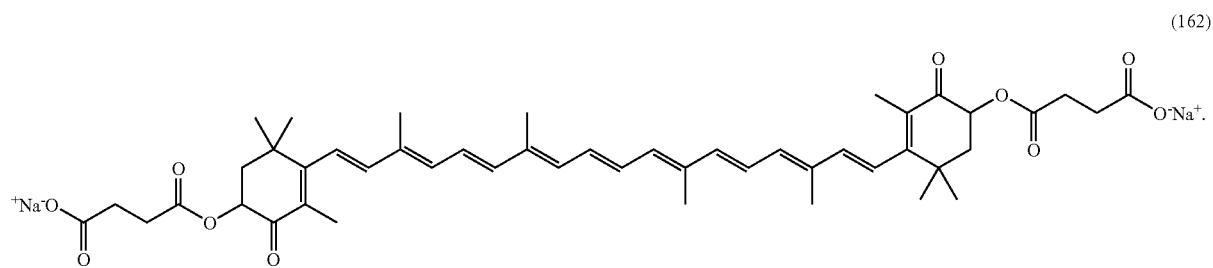

(162)

In some embodiments, a chemical compound may include a carotenoid derivative with a co-antioxidant, in particular one or more analogs or derivatives of vitamin C (i.e., L ascorbic acid) coupled to a carotenoid. Some embodiments may include carboxylic acid and/or carboxylate derivatives of vitamin C coupled to a carotenoid (e.g., structure (164))

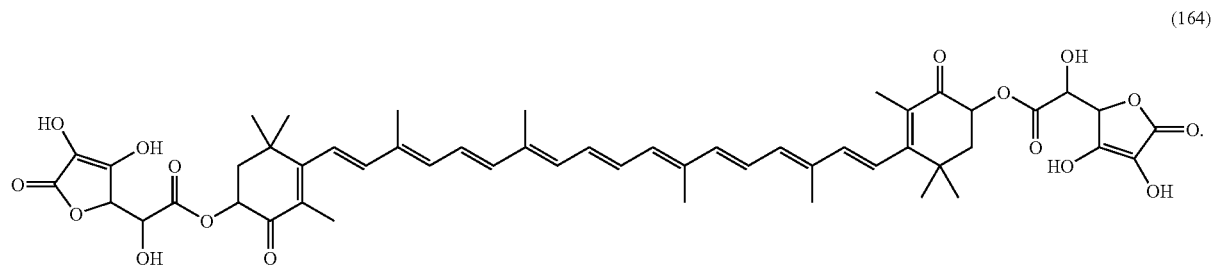

(164)

Carbohydr. Res. 1978, 60, 251-258 herein incorporated by reference, discloses oxidation at C-6 of ascorbic acid as depicted in EQN. 5.

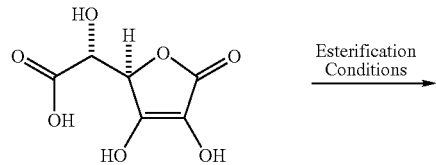 Esterification Conditions →

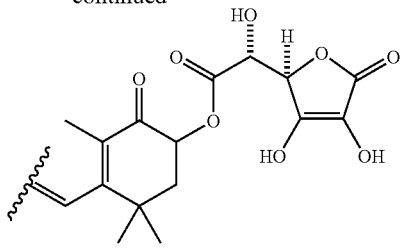

(5)

Some embodiments may include vitamin C and/or vitamin C analogs or derivatives coupled to a carotenoid. Vitamin C may be coupled to the carotenoid via an ether linkage (e.g., structure (166))

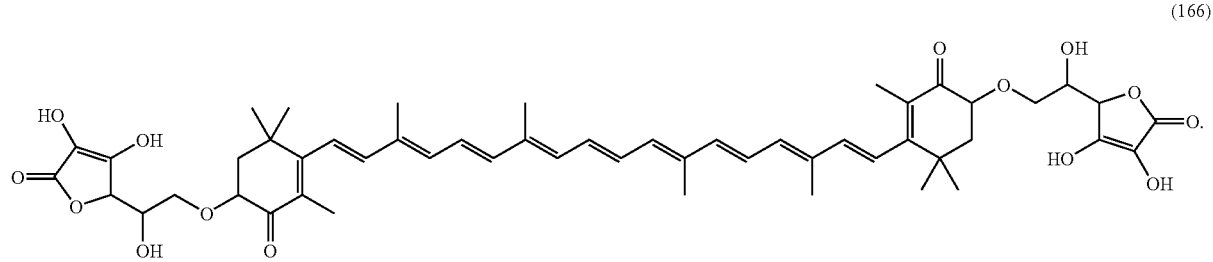

(166)

Some embodiments may include vitamin C disuccinate analogs or derivatives coupled to a carotenoid (e.g., structure (168))

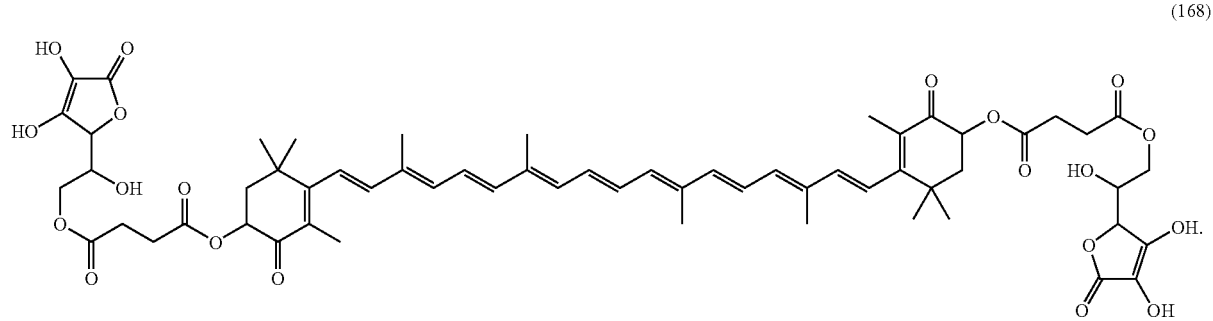

(168)

Some embodiments may include solutions or pharmaceutical preparations of carotenoids and/or carotenoid derivatives combined with co-antioxidants, in particular vitamin C and/or vitamin C analogs or derivatives. Pharmaceutical preparations may include about a 2:1 ratio of vitamin C to carotenoid respectively.

In some embodiments, co-antioxidants (e.g., vitamin C) may increase solubility of the chemical compound. In certain embodiments, co-antioxidants (e.g., vitamin C) may decrease toxicity associated with at least some carotenoid analogs or derivatives. In certain embodiments, co-antioxidants (e.g., vitamin C) may increase the potency of the chemical compound synergistically. Co-antioxidants may be coupled (e.g., a covalent bond) to the carotenoid derivative. Co-antioxidants may be included as a part of a pharmaceutically acceptable formulation.

In some embodiments, a carotenoid (e.g., astaxanthin) may be coupled to vitamin C forming an ether linkage. The ether linkage may be formed using the Mitsunobu reaction as in EQN. 1.

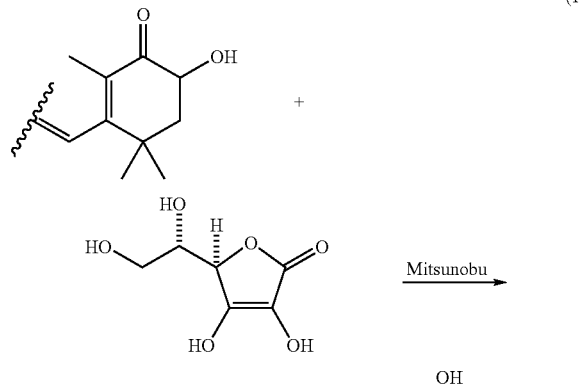

(1)

In some embodiments, vitamin C may be selectively esterified. Vitamin C may be selectively esterified at the C-3 position (e.g., EQN. 2). *J. Org. Chem.* 2000, 65, 911-913, herein incorporated by reference, discloses selective esterification at C-3 of unprotected ascorbic acid with primary alcohols.

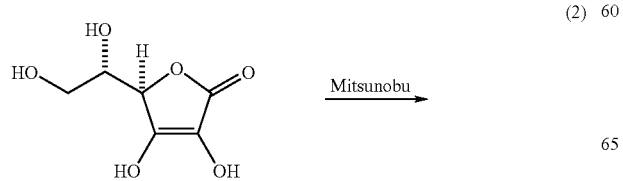

(2)

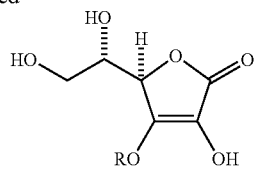

R = Me, 77%
Propyl, 63%
Octyl, 72%
allyl, 72%
benzyl, 64%

In some embodiments, a carotenoid may be coupled to vitamin C. Vitamin C may be coupled to the carotenoid at the C-6, C-5 diol position as depicted in EQNS. 3 and 4 forming an acetal.

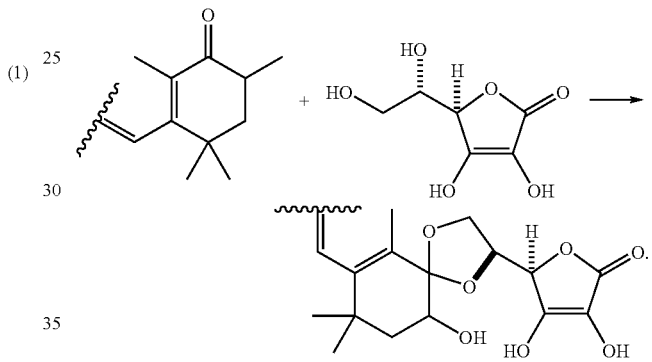

(3)

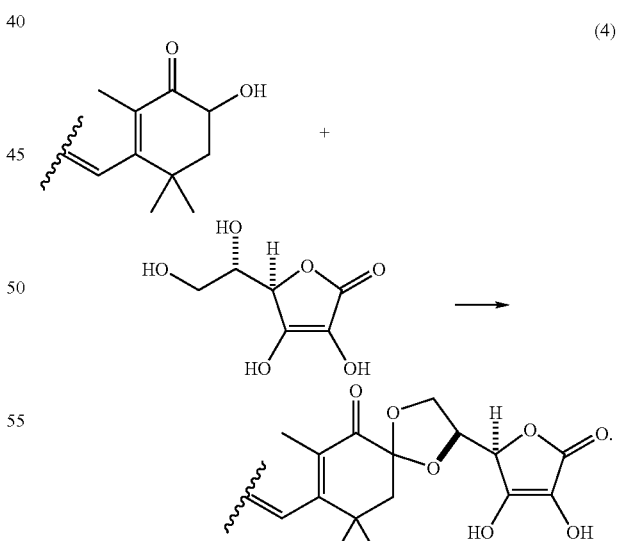

(4)

In some embodiments, a carotenoid may be coupled to a water-soluble moiety (e.g., vitamin C) with a glyoxylate linker as depicted in EQN. 6. *Tetrahedron* 1989, 22, 6987-6998, herein incorporated by reference, discloses similar acetal formations.

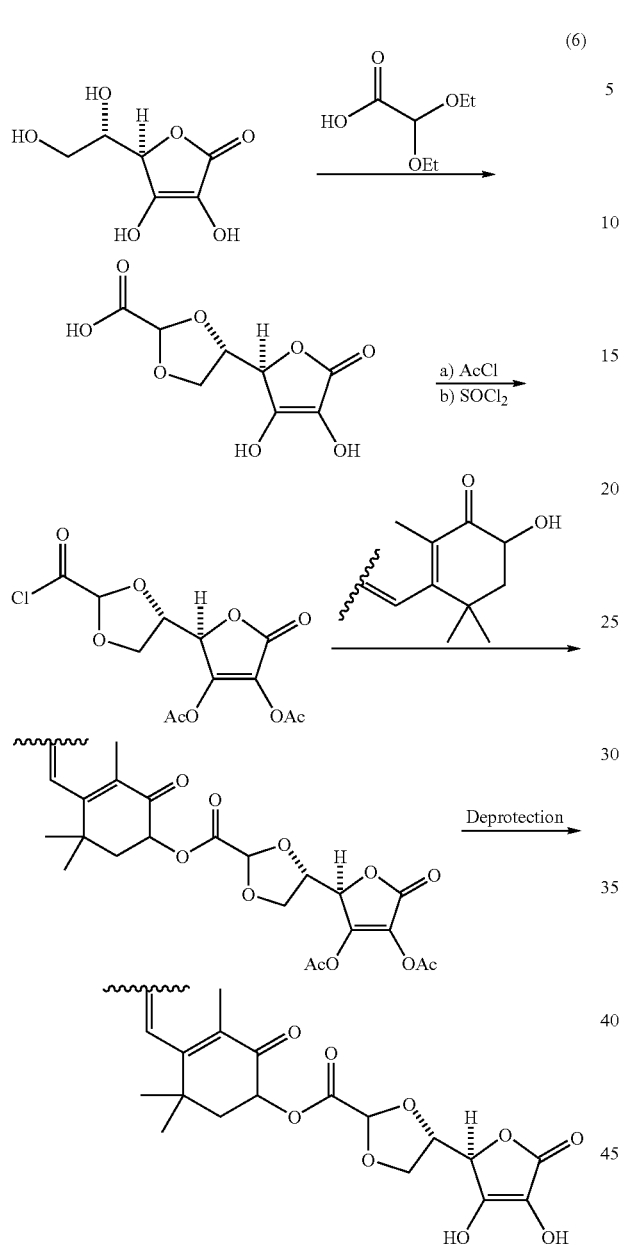

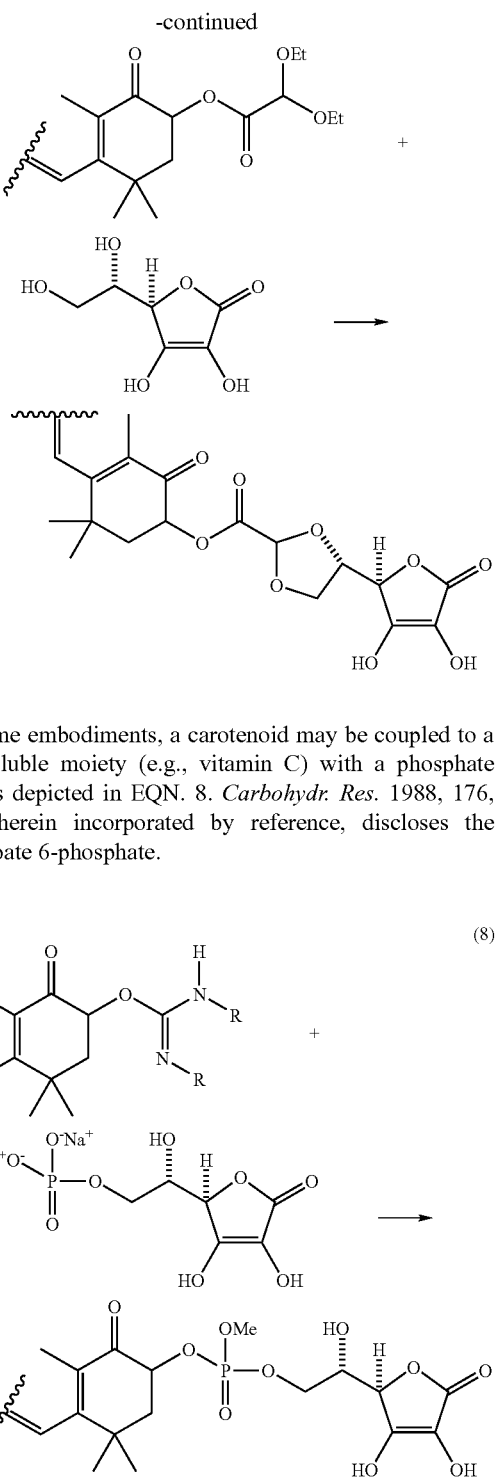

In some embodiments, a carotenoid may be coupled to a water-soluble moiety (e.g., vitamin C) with a glyoxylate linker as depicted in EQN. 7. *J. Med. Chem.* 1988, 31, 1363-1368, herein incorporated by reference, discloses the glyoxylic acid chloride.

In some embodiments, a carotenoid may be coupled to a water-soluble moiety (e.g., vitamin C) with a phosphate linker as depicted in EQN. 8. *Carbohydr. Res.* 1988, 176, 73-78, herein incorporated by reference, discloses the L-ascorbate 6-phosphate.

In some embodiments, a carotenoid may be coupled to a water-soluble moiety (e.g., vitamin C) with a phosphate linker as depicted in EQN. 9. *Carbohydr. Res.* 1979, 68, 313-319, herein incorporated by reference, discloses the 6-bromo derivative of vitamin C. *Carbohydr. Res.* 1988, 176, 73-78, herein incorporated by reference, discloses the 6-bromo derivative of vitamin C's reaction with phosphates.

(9)

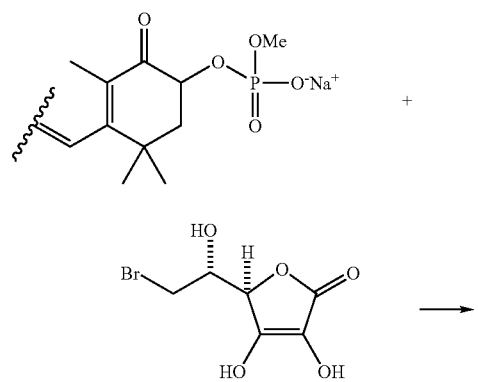

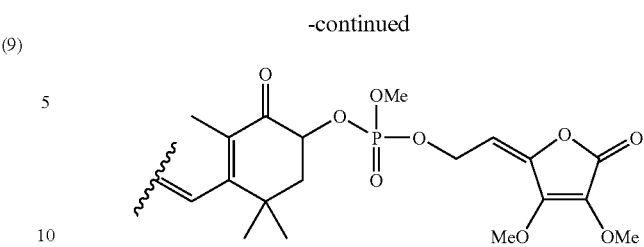

In some embodiments, a carotenoid may be coupled to a water-soluble moiety (e.g., vitamin C) with a phosphate linker as depicted in EQN. 11. Vitamin C may be coupled to the carotenoid using selective esterification at C-3 of unprotected ascorbic acid with primary alcohols.

In some embodiments, a carotenoid may be coupled to a water-soluble moiety (e.g., vitamin C) with a phosphate linker as depicted in EQN. 10. *J. Med. Chem.* 2001, 44, 1749-1757 and *J. Med. Chem.* 2001, 44, 3710-3720, herein incorporated by reference, disclose the allyl chloride derivative and its reaction with nucleophiles, including phosphates, under mild basic conditions.

(10)

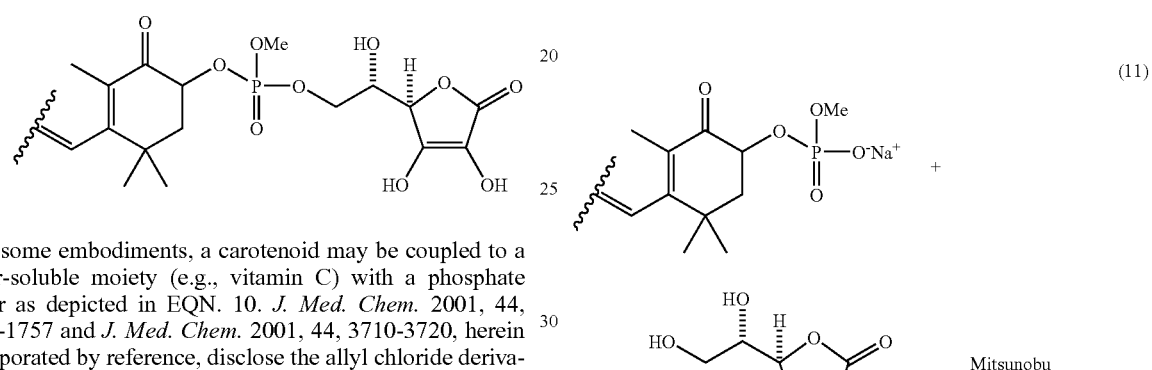

(11)

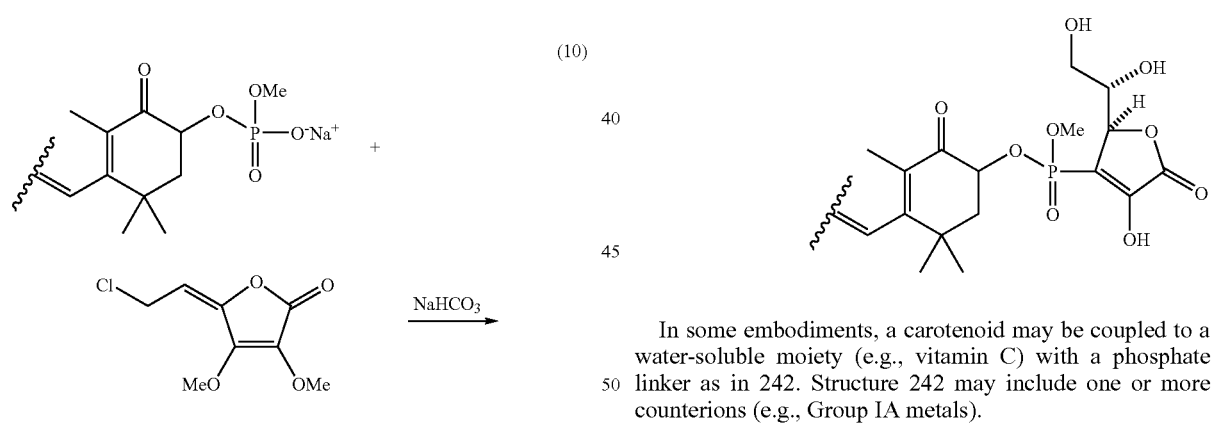

In some embodiments, a carotenoid may be coupled to a water-soluble moiety (e.g., vitamin C) with a phosphate linker as in 242. Structure 242 may include one or more counterions (e.g., Group IA metals).

242

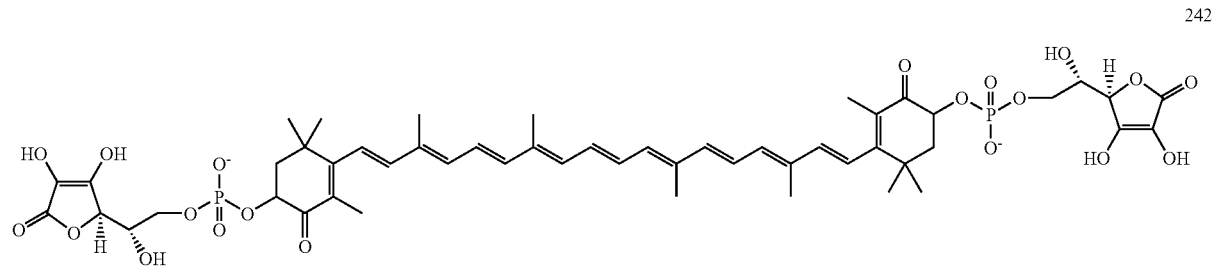

EQN. 12 depicts an example of a synthesis of a protected form of 242.

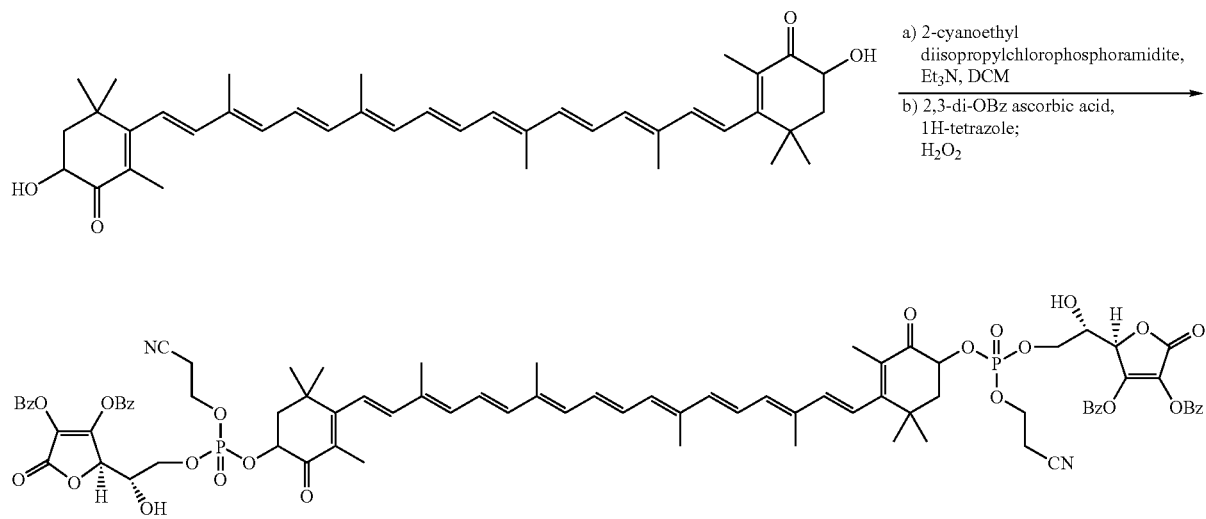

(12)

a) 2-cyanoethyl diisopropylchlorophosphoramidite, Et₃N, DCM
b) 2,3-di-OBz ascorbic acid, 1H-tetrazole; H₂O₂

In some embodiments, a chemical compound may include a carotenoid derivative including one or more amino acids (e.g., lysine) and/or amino acid analogs or derivatives (e.g., lysine hydrochloric acid salt) coupled to a carotenoid (e.g., structure (170)).

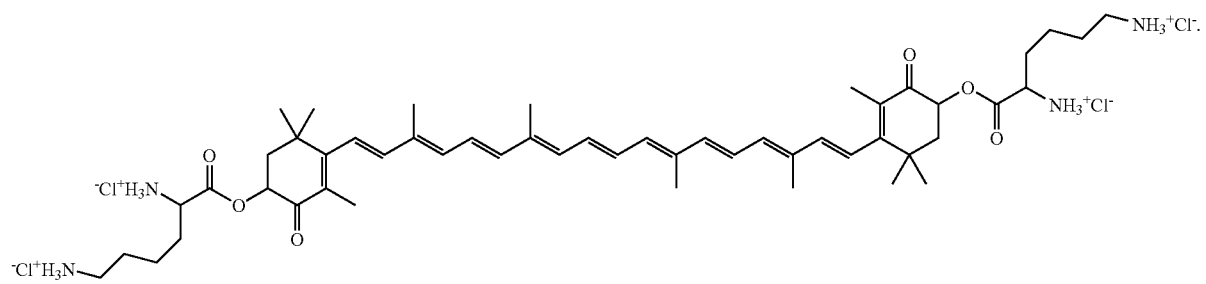

(170)

In some embodiments, a carotenoid analog or derivative may include:

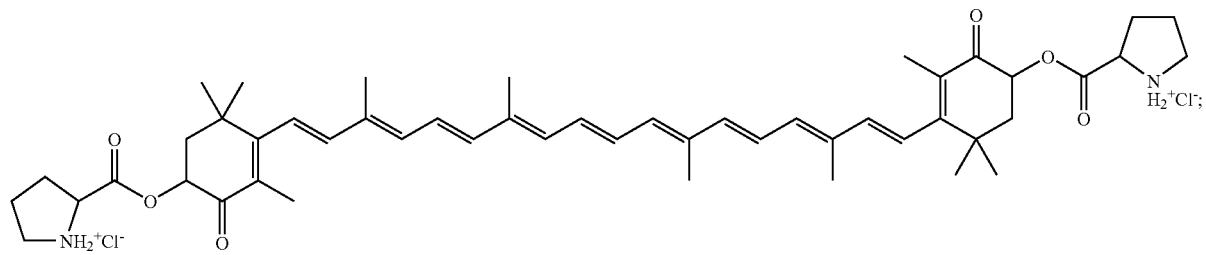

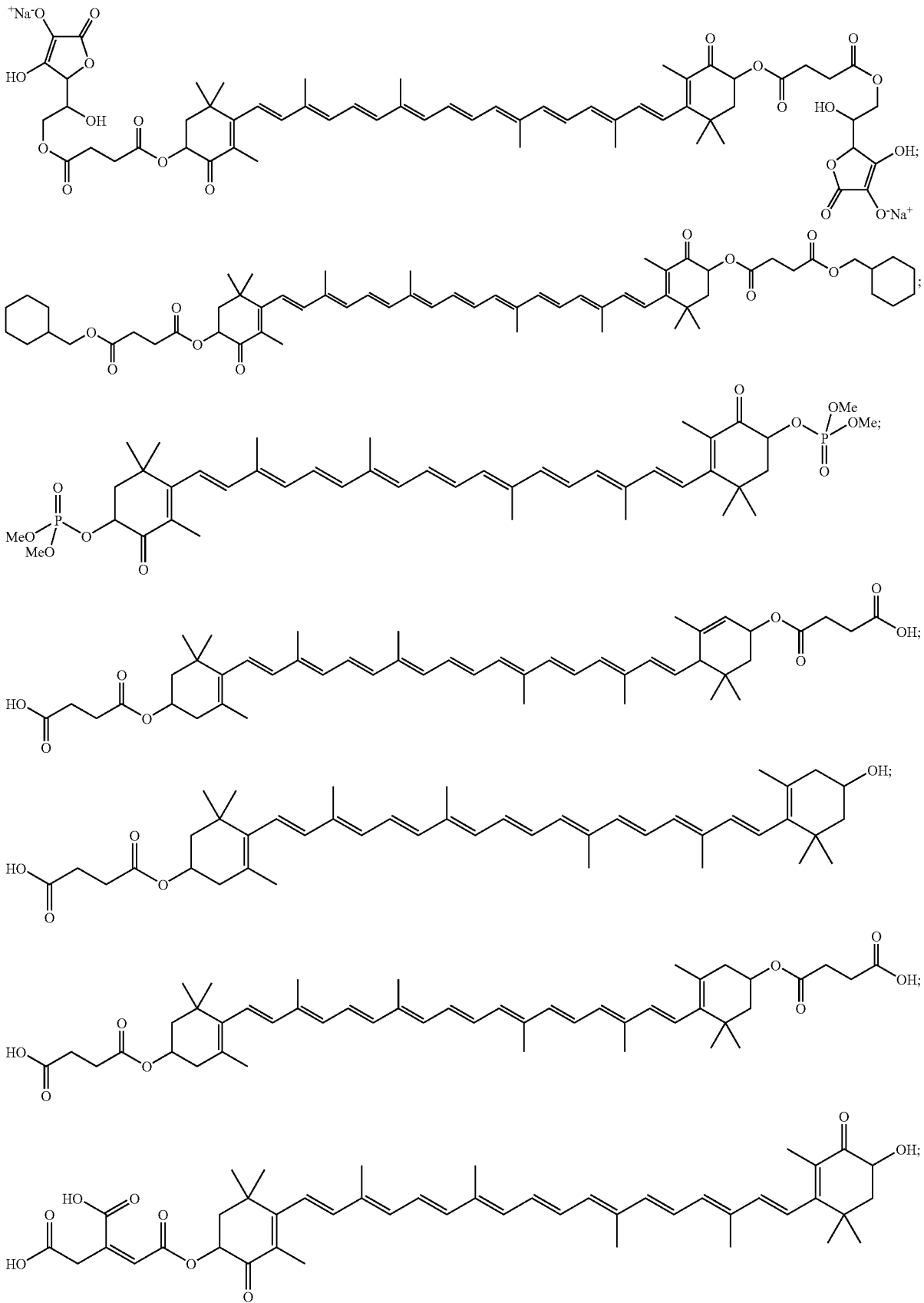

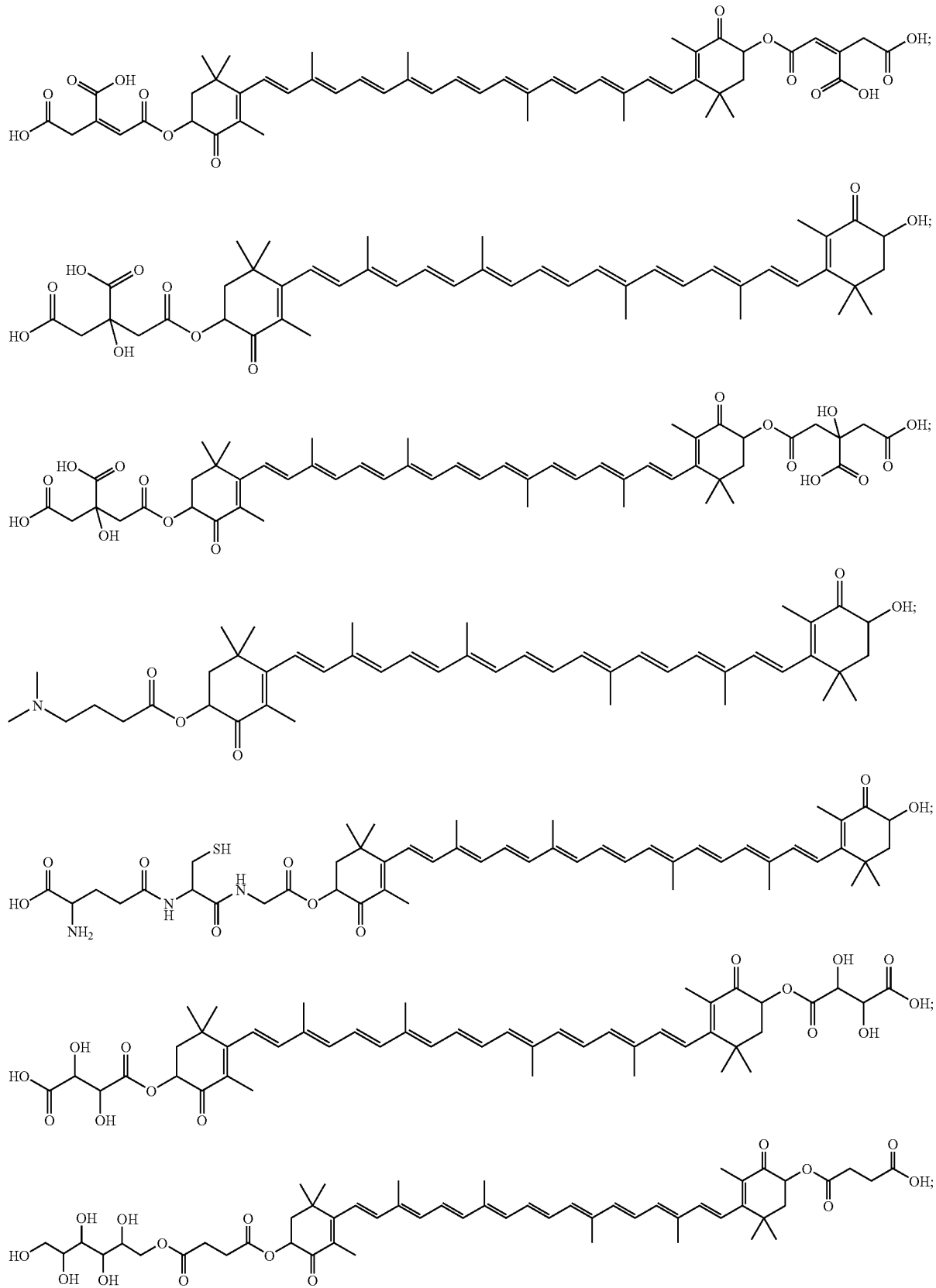

-continued
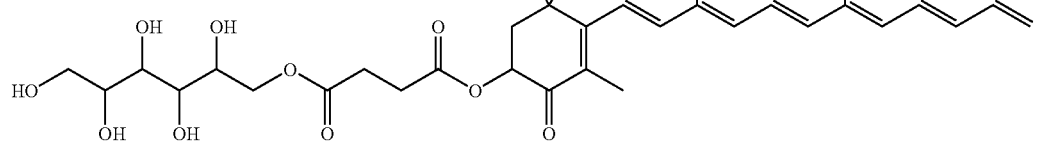
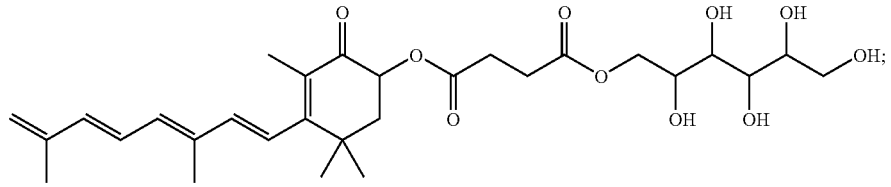
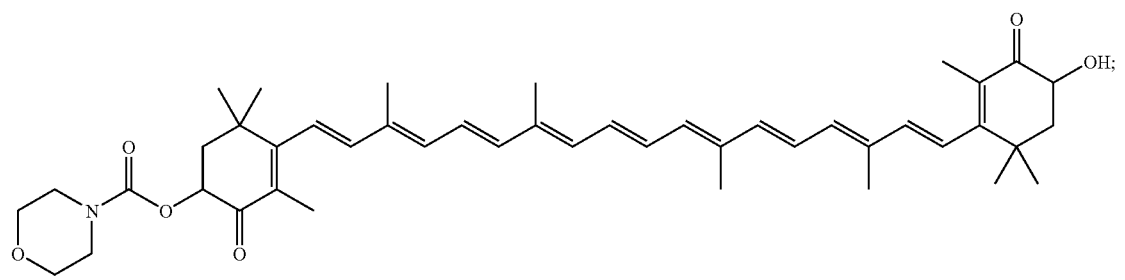
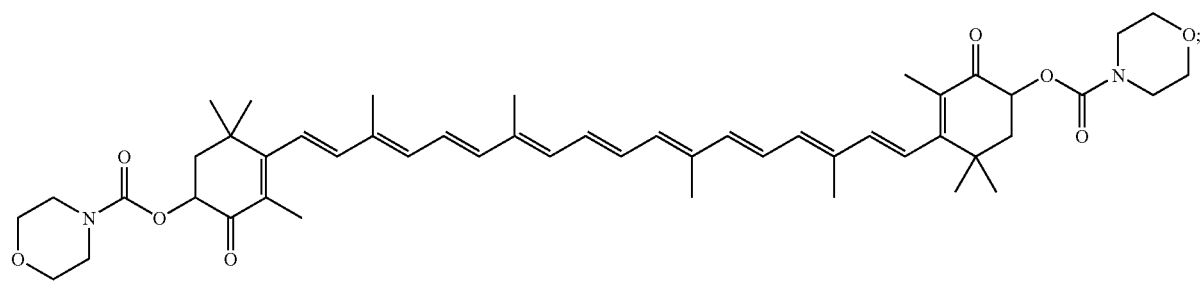
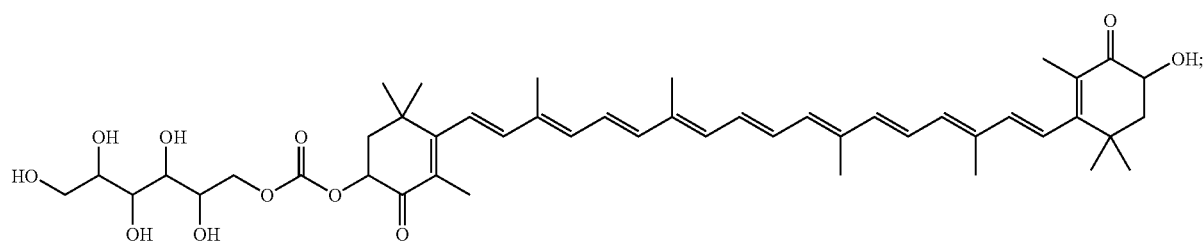
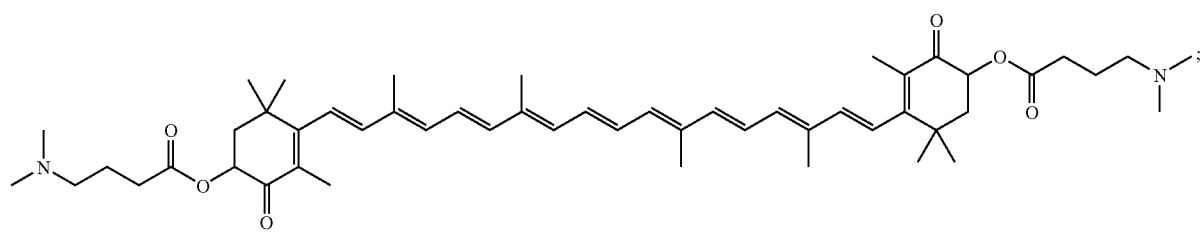
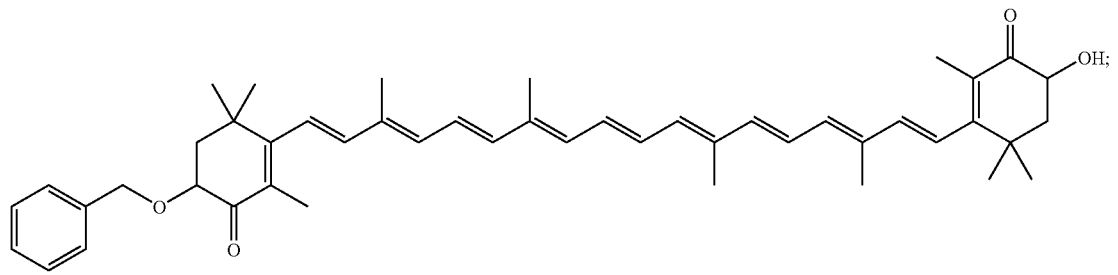

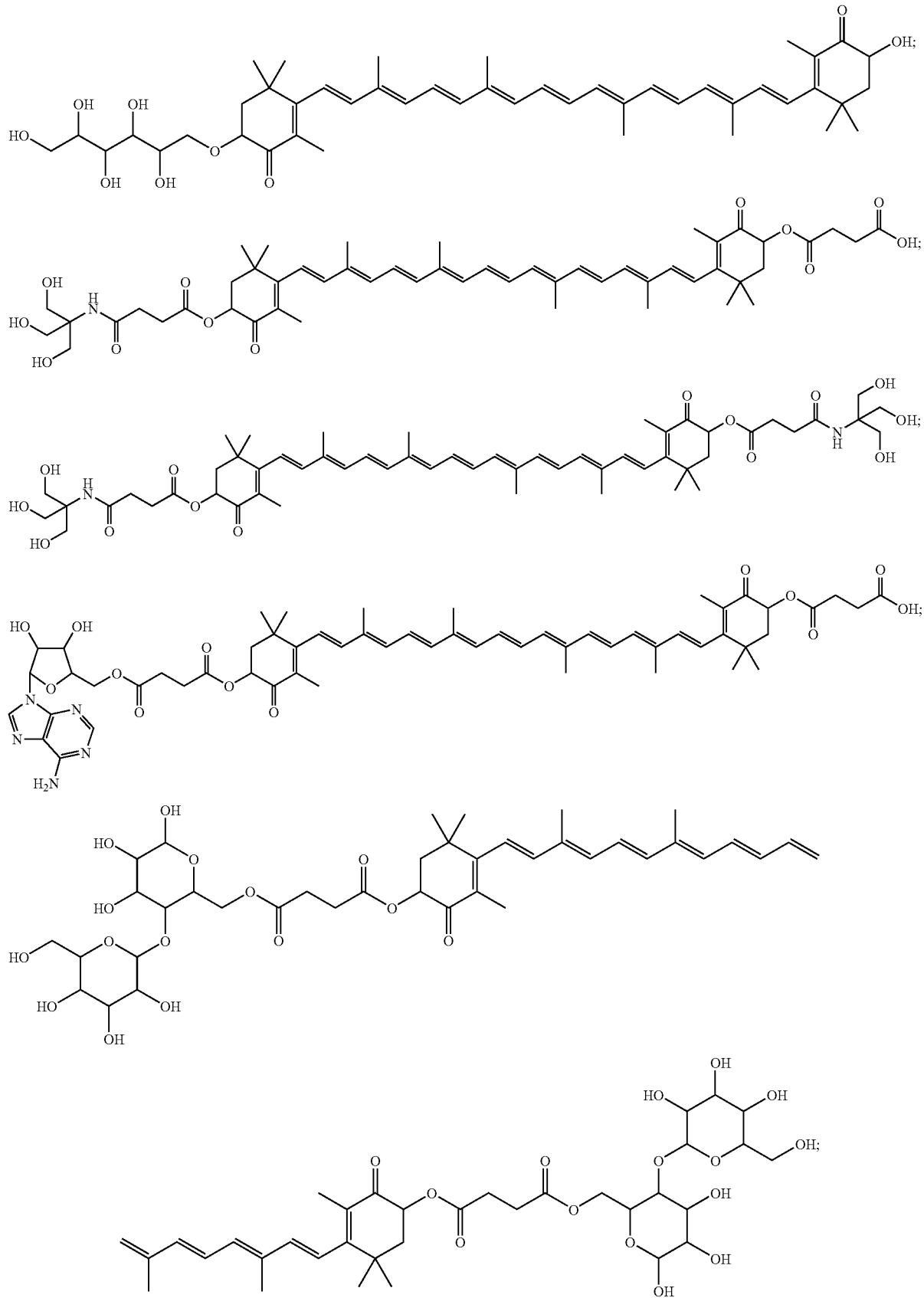

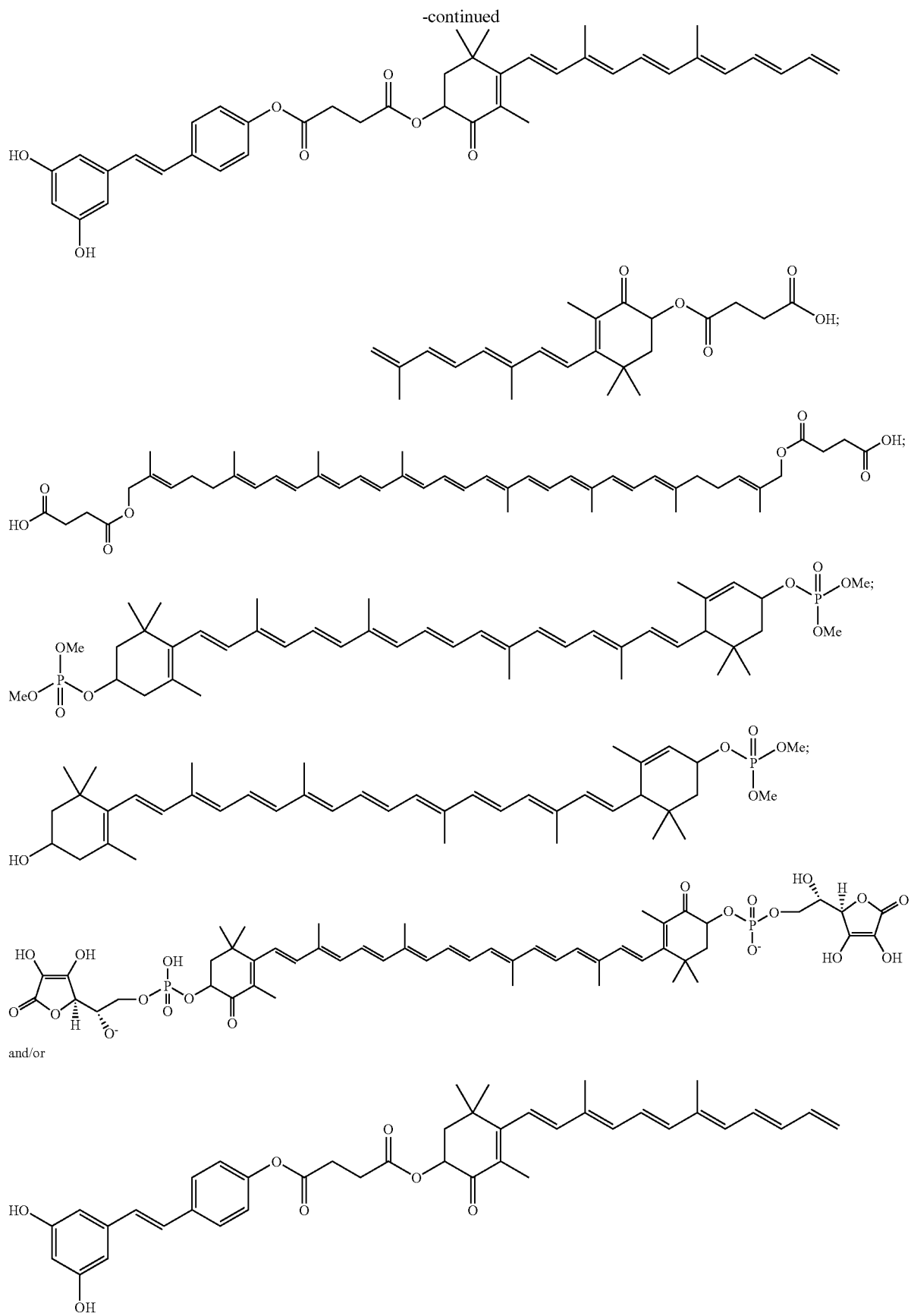

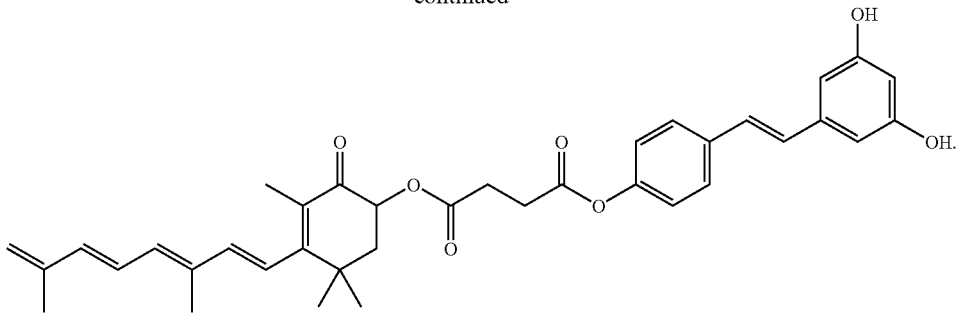

In some embodiments, a chemical compound may include a disuccinic acid ester carotenoid derivative having the structure (160)

Some specific embodiments may include phosphate, succinate, co-antioxidant (e.g., Vitamin C, Vitamin C analogs, Vitamin C derivatives, Vitamin E, Vitamin E analogs, Vitamin E derivatives, or flavonoids), or combinations thereof derivatives or analogs of carotenoids. Flavonoids may include, for example, quercetin, xanthohumol, isoxanthohumol, or genistein. Derivatives or analogs may be derived from any known carotenoid (naturally or synthetically derived). Specific examples of naturally occurring carotenoids which compounds described herein may be derived from include for example zeaxanthin, lutein, lycophyll, astaxanthin, and lycopene.

(160)

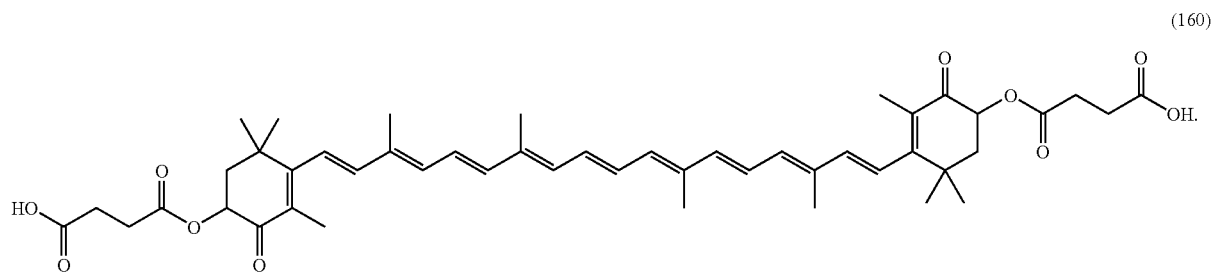

In some embodiments, a chemical compound may include a disodium salt disuccinic acid ester carotenoid derivative having the structure (162)

(162)

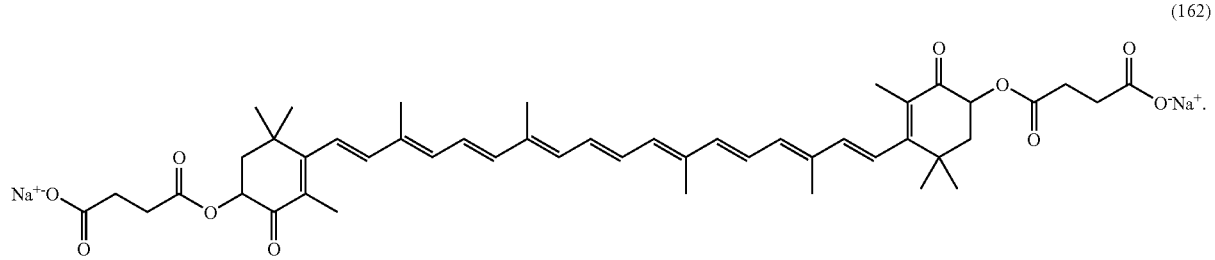

Compounds described herein embrace isomers mixtures, racemic, optically active, and optically inactive stereoisomers and compounds. Carotenoid analogs or derivatives may have increased water solubility and/or water dispersibility relative to some or all known naturally occurring carotenoids. In some embodiments, one or more co-antioxidants may be coupled to a carotenoid or carotenoid derivative or analog.

In some embodiments, carotenoid analogs or derivatives may be employed in "self-formulating" aqueous solutions, in which the compounds spontaneously self-assemble into macromolecular complexes. These complexes may provide stable formulations in terms of shelf life. The same formulations may be parenterally administered, upon which the spontaneous self-assembly is overcome by interactions with serum and/or tissue components in vivo.

The synthesis of water-soluble and/or water-dispersible carotenoids (e.g., C40) analogs or derivatives—as potential parenteral agents for clinical applications may improve the injectability of these compounds as therapeutic agents, a result perhaps not achievable through other formulation methods. The methodology may be extended to carotenoids with fewer than 40 carbon atoms in the molecular skeleton and differing ionic character. The methodology may be extended to carotenoids with greater than 40 carbon atoms in the molecular skeleton. The methodology may be extended to non-symmetric carotenoids. The aqueous dispersibility of these compounds allows proof-of-concept studies in model systems (e.g. cell culture), where the high lipophilicity of these compounds previously limited their bioavailability and hence proper evaluation of efficacy. Esterification or etherification may be useful to increase oral bioavailability, a fortuitous side effect of the esterification process, which can increase solubility in gastric mixed micelles. The net overall effect is an improvement in potential clinical utility for the lipophilic carotenoid compounds as therapeutic agents.

In some embodiments, the principles of retrometabolic drug design may be utilized to produce novel soft drugs from the asymmetric parent carotenoid scaffold (e.g., RRR-lutein (β,ε-carotene-3,3'-diol)). For example, lutein scaffold for derivatization was obtained commercially as purified natural plant source material, and was primarily the RRR-stereoisomer (one of 8 potential stereoisomers). Lutein (Scheme 1) possesses key characteristics—similar to starting material astaxanthin—which make it an ideal starting platform for retrometabolic syntheses: (1) synthetic handles (hydroxyl groups) for conjugation, and (2) an excellent safety profile for the parent compound.

In some embodiments, carotenoid analogs or derivatives may have increased water solubility and/or water dispersibility relative to some or all known naturally occurring carotenoids.

In some embodiments, the carotenoid derivatives may include compounds having a structure including a polyene chain (i.e., backbone of the molecule). The polyene chain may include between about 5 and about 15 unsaturated bonds. In certain embodiments, the polyene chain may include between about 7 and about 12 unsaturated bonds. In some embodiments a carotenoid derivative may include 7 or more conjugated double bonds to achieve acceptable antioxidant properties.

In some embodiments, decreased antioxidant properties associated with shorter polyene chains may be overcome by increasing the dosage administered to a subject or patient.

In some embodiments, the carotenoid derivatives or analogs may be synthesized from naturally occurring carotenoids. In some embodiments, the carotenoid derivatives may be synthesized from any naturally occurring carotenoid including one or more alcohol substituents. In other embodiments, the carotenoid derivatives may be synthesized from a derivative of a naturally occurring carotenoid including one or more alcohol substituents. The synthesis may result in a single stereoisomer. The synthesis may result in a single geometric isomer of the carotenoid derivative. The synthesis/synthetic sequence may include any prior purification or isolation steps carried out on the parent carotenoid.

In some embodiments, a synthesis may be a total synthesis using methods described herein to synthesize carotenoid derivatives and/or analogs. An example may include, but is not limited to, a 3S,3'S all-E carotenoid derivative, where the parent carotenoid is astaxanthin. The synthetic sequence may include protecting and subsequently deprotecting various functionalities of the carotenoid and/or substituent precursor. When derivates or analogs are prepared from alcohol-functionalized carotenoids, a base catalyzed reaction may be used to react the alcohol functional groups with the substituent precursor. Substituent precursors include precursors that include a functional group that may act as a leaving group for a substitution reaction. The base may include any non-nucleophilic base known to one skilled in the art such as, for example, tertiary amines, pyridine, pyrrolidine, etc. The alcohol may act as a nucleophile reacting with the substituent precursor, displacing the leaving group. Leaving groups may include, but are not limited to; I, Cl, Br, tosyl, brosyl, mesyl, or trifyl. These are only a few examples of leaving groups that may be used, many more are known and would be apparent to one skilled in the art. In some embodiments, a base may be used to deprotonate the alcohol. For example, reaction with alkyl lithium bases, alkali metal hydroxide, or alkali metal alcohol salts may deprotonate a hydroxy group of the carotenoid. In other examples the leaving group may be internal and may subsequently be included in the final structure of the carotenoid derivative, a non-limiting example may include anhydrides or strained cyclic ethers. For example, the alcohol may be reacted with succinic anhydride.

In an embodiment, the disuccinic acid ester of astaxanthin may be further converted to the disodium salt. Examples of synthetic sequences for the preparation of some of the specific embodiments depicted are described in the Examples section. The example depicted below is a generic non-limiting example of a synthetic sequence for the preparation of astaxanthin carotenoid derivatives.

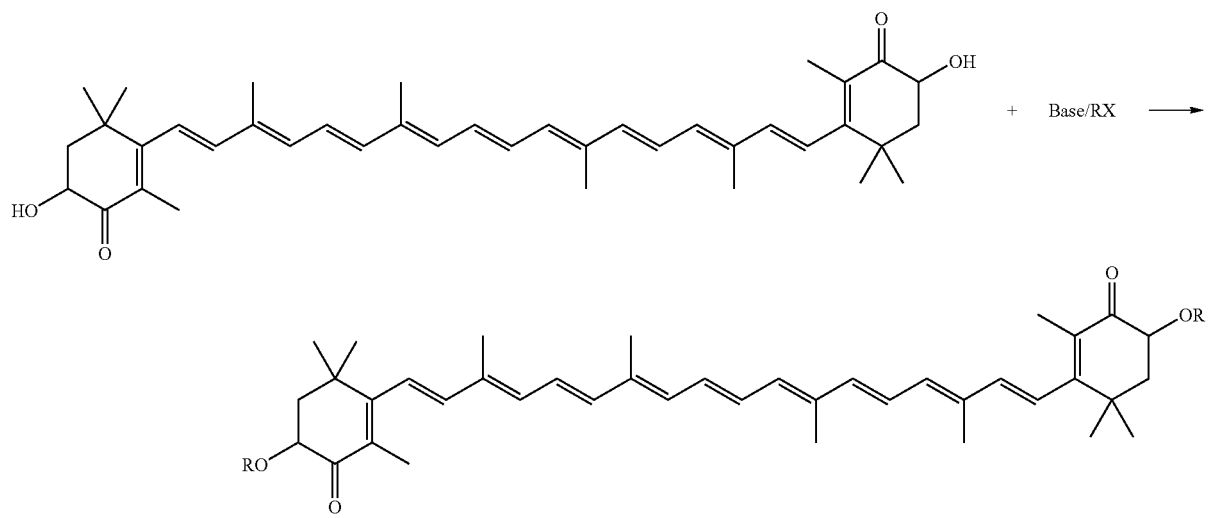

In some embodiments, one or more of the conversions and/or reactions discussed herein may be carried out within one reaction vessel increasing the overall efficiency of the synthesis of the final product. In some embodiments, a product of one reaction during a total synthesis may not be fully worked up before continuing on with the following reaction. In general, fully working up a reaction implies completely isolating and purify the product from a reaction. A reaction may instead only partially be worked up. For example, solid impurities, which fall out of solution during the course of a reaction, may be filtered off and the filtrate washed with solvent to ensure all of the resulting product is washed through and collected. In such a case the resulting collected product still in solution may not be isolated, but may then be combined with another reagent and further transformed. In some cases multiple transformations may be carried out in a single reaction flask simply by adding reagents one at a time without working up intermediate products. These types of "shortcuts" will improve the overall efficiency of a synthesis, especially when dealing with larger quantity reactions (e.g., along the lines of pilot plant scale and/or plant scale).

In some embodiments, an alcohol-functionalized carotenoid may provide a skeleton with a useful handle with which to appropriately derivative a carotenoid based water dispersible end product. The example depicted above is a generic non-limiting example; examples depicted in Schemes 1 and 2 provide more specific examples of the synthesis of water-soluble and/or water-dispersible carotenoid analogs or derivatives. Schemes 1 and 2 depict the syntheses of two water-dispersible lutein derivatives, the sodium salts of lutein disuccinate and lutein diphosphate. Derivatizing hydrophobic carotenoids may impart water-dispersibility.

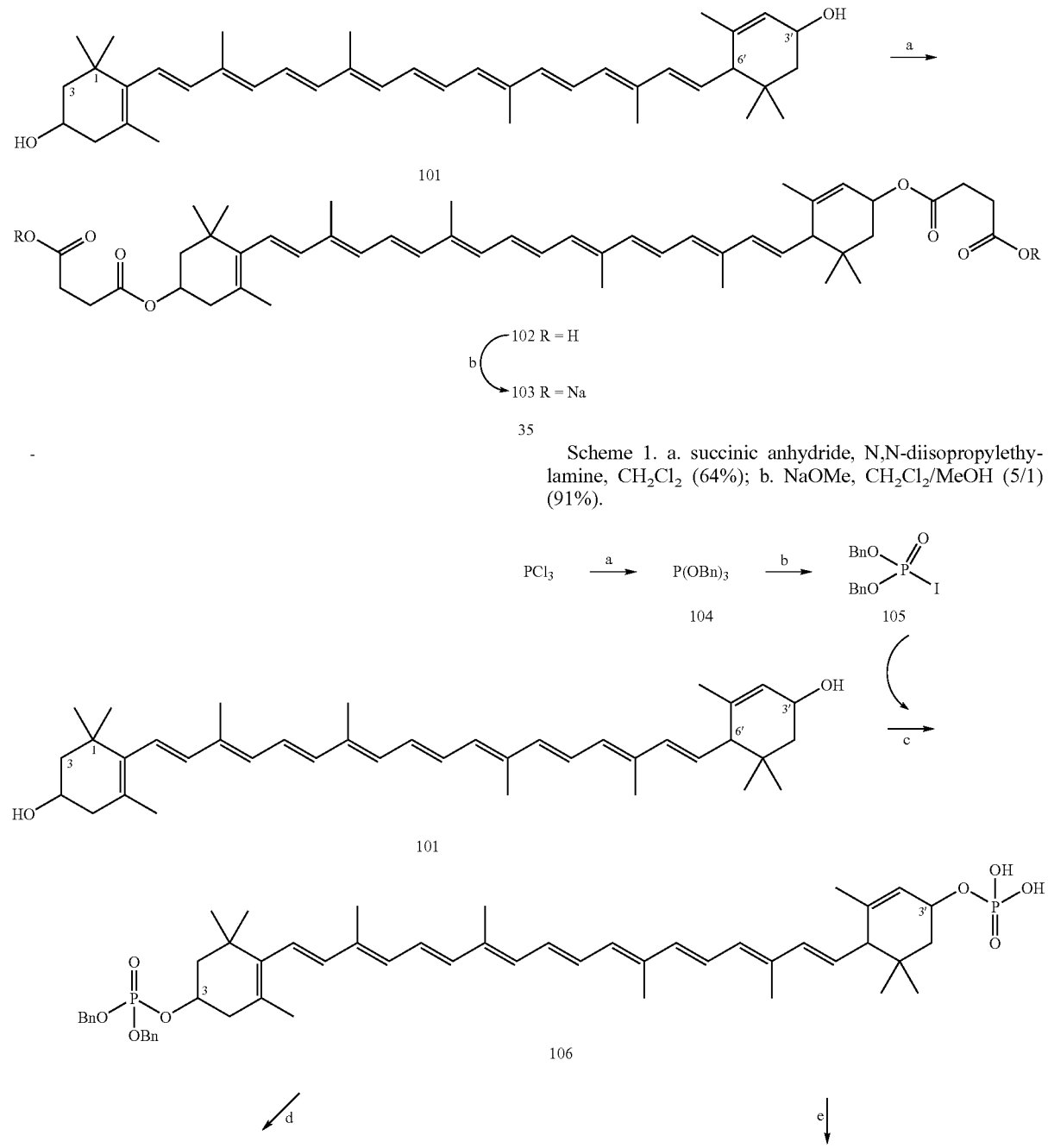

Scheme 1. a. succinic anhydride, N,N-diisopropylethylamine, $CH_2Cl_2$ (64%); b. NaOMe, $CH_2Cl_2$/MeOH (5/1) (91%).

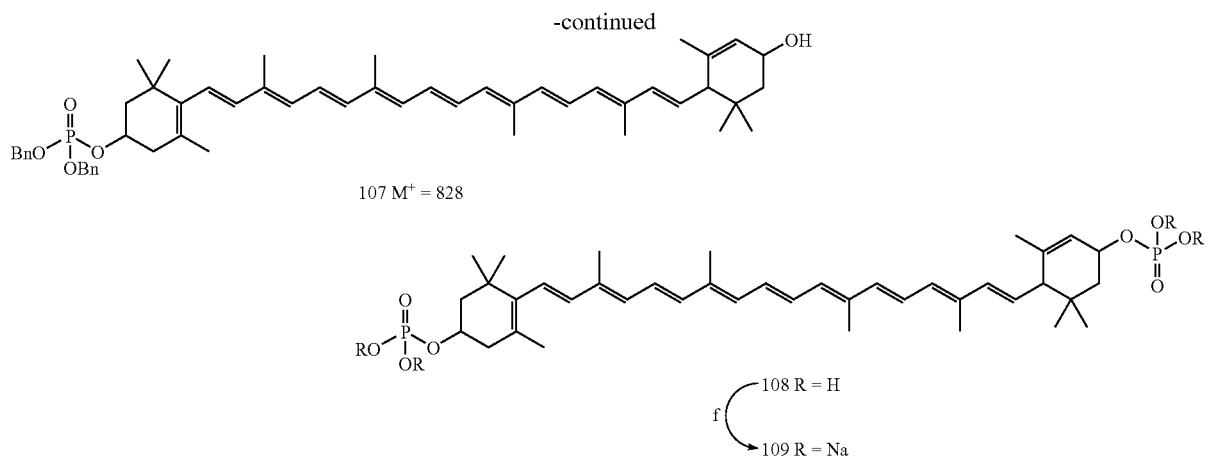

107 M+ = 828

108 R = H
109 R = Na

Scheme 2. a. benzyl alcohol, triethylamine, Et$_2$O (83%); b. I$_2$, CH$_2$Cl$_2$; c. 101, pyridine, CH$_2$Cl$_2$ then 105; d. LiOH—H$_2$O, tetrahydrofuran/H$_2$O (2/1); e. bromotrimethylsilane, N,O-bis(trimethylsilyl)acetamide, CH$_2$Cl$_2$;f. NaOMe, MeOH (80% for 3 steps).

As seen in Scheme 1, the synthesis of disuccinate salt 103 began with succinylation of natural source lutein using succinic anhydride and Hünig base (N,N'-diisopropylethylamine). Reactions may be run in polar organic solvents. Disuccinylation of lutein was optimized by running the reaction in a concentrated fashion and using modest excesses of anhydride and base. Using high concentrations of reagents may allow easier extraction of impurities and side products once the reaction is complete. Aqueous acidic workup yielded disuccinate 102, such that excess reagents and reaction byproducts were removed by copiously extracting the organic layer with dilute HCl. The resulting viscous, red-orange oil was washed or slurried with hexanes to remove non-polar impurities. A successfully functionalized carotenoid may be transformed into an ionic salt derivative or analog in order to increase the water solubility. A carotenoid may be transformed into an ionic salt derivative or analog by reacting the carotenoid with a base. Bases may include alkali metal hydroxides (e.g., sodium hydroxide) or tertiary amines (e.g., triethylamine). In some embodiments, bases, upon deprotonation of one or more moieties of the carotenoid may result in by products which are easily removed (e.g., removed under reduced pressure, extracted). The water-dispersible derivative 103 was generated by treating compound 102 with methanolic sodium methoxide. The reaction was quenched with water and the resulting red-orange aqueous layer was first extracted with Et$_2$O, then lyophilized to provide the sodium salt in good yield.

In some embodiments, a carotenoid may be phosphorylated to increase water solubility and/or dispersibility. In some embodiments, a carotenoid may be diphosphorylated to increase water solubility and/or dispersibility. Successful diphosphorylation of lutein may be achieved using dimethyl phosphoroiodidate. Dimethyl phosphoroiodidate may be formed in situ. Dimethyl phosphoroiodidate may be formed by reacting commercially available trimethyl phosphite with iodine. In some embodiments, a certain degree of success in removing all four diphosphate methyl groups may be realized when using bromotrimethylsilane in the presence of N,O-bis (trimethylsilyl)acetamde. However, this deprotection protocol may not be optimal in that methyl group dealkylation was usually accompanied by the significant decomposition of lutein phosphate.

In some embodiments, a three-step method to provide the tetra-sodium salt of lutein diphosphate 109 may be achieved using benzyl esters as protecting groups for the lutein phosphoric acids (Scheme 2). Lutein (e.g., natural source) may be phosphorylated using dibenzyl phosphoroiodidate. Dibenzyl phosphoroiodidate may be formed in situ. Dibenzyl phosphoroiodidate may be formed by reacting tribenzyl phosphite with iodine. As seen in Scheme 2, tribenzyl phosphite may be prepared by the addition of benzyl alcohol to phosphorus trichloride in the presence of triethylamine. In some embodiments, silica gel chromatography of the crude reaction mixture may yield tribenzyl phosphite in good yield. Compound 106 was formed by treating lutein with freshly prepared dibenzyl phosphoroiodidate in the presence of pyridine. Aqueous workup of the reaction followed by the removal of pyridine by azeotropic distillation using toluene may provide a crude red oil. Contaminations, excess reagents, and reaction byproducts may be removed during work up of the reaction or at a later time (e.g., after a subsequent reaction). Non-polar impurities may be removed from the crude product mixture by alternately washing or slurrying with hexanes and Et$_2$O to give 106.

In some embodiments, dealkylation of one or more of the four benzyl esters of the phosphoric acid moieties may occur during the phosphorylation reaction. Dealkylation may occur at the more sensitive allylic 3' phosphate positions. As seen in Scheme 2, the attempted removal of the phosphoric acid benzyl esters of 106 using LiOH—H$_2$O may result in the generation of a less polar product versus compound 106, exhibiting a molecular ion of 828 as noted by LC/MS analysis. Under these reaction conditions, dephosphorylation at one of the two hydroxyls of the lutein derivative may occur rather than the desired debenzylation to give compound 107. Such data indirectly support compound 106's structure and thus the occurrence of bis-dealkylation at one phosphate versus mono-dealkylation at both phosphates as an additional result of the phosphorylation of lutein. If mono-dealkylation at both phosphates occurred during phosphorylation, then treatment of the resulting product with LiOH—H$_2$O would have produced a lutein derivative possessing one phosphoric acid containing only one benzyl ester, exhibiting a molecular ion of 738 upon LC/MS analysis.

In some embodiments, successful dealkylation of the phosphate protecting groups of 106 may be achieved using bromotrimethylsilane in the presence of N,O-bis(trimethylsilyl) acetamide (see Scheme 2). A significant amount of excess reagents and reaction byproducts may be removed from the resulting red oil by alternately washing or slurrying the crude mixture with ethyl acetate and $CH_2Cl_2$ to provide diphosphate 108 as an orange oil.

In some embodiments, the sodium salt of lutein diphosphate (109) may be generated by treating 108 with methanolic sodium methoxide (see Scheme 2). The resulting crude orange solid may be washed or slurried with methanol and then dissolved in water. The aqueous layer may be extracted first with $CH_2Cl_2$, then with ethyl acetate, and again with $CH_2Cl_2$. Lyophilization of the red-orange aqueous solution may give the sodium salt as an orange, hygroscopic solid. The phosphorylation process may provide the desired water-dispersible lutein derivative 109 in good yield over the three steps.

The synthetic preparation of carotenoid derivatives or analogs such as disodium disuccinate astaxanthin 162 at multigram scale (e.g., 200 g to 1 kg) is necessary if one wishes to produce these molecules commercially. Synthetic modifications of carotenoids, with the goal of increasing aqueous solubility and/or dispersibility, have been sparingly reported in the literature. At the time process development began, surveys of the peer-reviewed and patent literature indicated that neither a synthetic sequence nor an efficient process for the synthesis of 160 or 162 had been reported. Therefore, the bench-scale synthetic sequence and later the scale-up to multigram scale were optimized to improve both the yield and purity of the desired compound. Examples of synthetic preparation of carotenoids and carotenoid derivatives or analogs are illustrated in U.S. Patent Application Ser. No. 60/615,032 filed on Oct. 1, 2004, entitled "METHODS FOR SYNTHESIS OF CAROTENOIDS, INCLUDING ANALOGS, DERIVATIVES, AND SYNTHETIC AND BIOLOGICAL INTERMEDIATES" to Lockwood et al. which is incorporated by reference as if fully set forth herein.

The disodium disuccinate derivatives of synthetic astaxanthin were successfully synthesized in gram amounts and at high purity (>90%) area under the curve (AUC) by HPLC. The compound in "racemic" form demonstrated water "dispersibility" of 8.64 mg/mL, a significant improvement over the parent compound astaxanthin, which is insoluble in water. Initial biophysical characterization demonstrated that Cardax™ derivatives (as both the statistical mixture of stereoisomers and as individual stereoisomers) were potent direct scavengers of superoxide anion in the aqueous phase, the first such description in this model system for a C40 carotenoid. Plasma-protein binding studies in vitro revealed that the meso-(3R,3'S)-disodium disuccinate astaxanthin derivative bound immediately and preferentially to human serum albumin (HSA) at a binding site, suggesting that beneficial ligand-binding associations might take place in vivo after parenteral administration of the compound. The single- and multiple-dose pharmacokinetics of an oral preparation of the racemic compound (in lipophilic emulsion) were then investigated in a murine model, and significant plasma and tissue levels of nonesterified astaxanthin were achieved. Proof-of-concept studies in ischemia-reperfusion injury performed in rodents subsequently revealed that intravenous pretreatment with Cardax™ was significantly cardioprotective and achieved myocardial salvage in this experimental infarction model (e.g., up to 56% at the highest dose tested). The test material for three of the studies described above was obtained from a single pilot batch of compound (>200 g single batch at >97% purity by HPLC).

In some embodiments, it may be advantageous to be able to efficiently separate out individual stereoisomers of a racemic mixture of a chemical compound. Efficiently separating out individual stereoisomers on a relatively large scale may advantageously increase availability of starting materials.

In some embodiments, chromatographic separation techniques may be used to separate stereoisomers of a racemic mixture. In some embodiments pure optically active stereoisomers may be reacted with a mixture of stereoisomers of a chemical compound to form a mixture of diastereomers. Diastereomers may have different physical properties as opposed to stereoisomers, thus making it easier to separate diastereomers.

For example it may be advantageous to separate out stereoisomers from a racemic mixture of astaxanthin. In some embodiments, astaxanthin may be coupled to an optically active compound (e.g., dicamphanic acid). Coupling astaxanthin to optically active compounds produces diastereomers with different physical properties. The diastereomers produced may be separated using chromatographic separation techniques as described herein.

Bulk chromatographic separation of the diastereomeric dicamphanic acid ester(s) of synthetic astaxanthin at preparative chromatography scale was performed to subsequently make gram-scale quantities of each stereoisomer of disodium disuccinate ester astaxanthin.

As used herein the terms "structural carotenoid analogs or derivatives" may be generally defined as carotenoids and the biologically active structural analogs or derivatives thereof. "Derivative" in the context of this application is generally defined as a chemical substance derived from another substance either directly or by modification or partial substitution. "Analog" in the context of this application is generally defined as a compound that resembles another in structure but is not necessarily an isomer. Typical analogs or derivatives include molecules which demonstrate equivalent or improved biologically useful and relevant function, but which differ structurally from the parent compounds. Parent carotenoids are selected from the more than 700 naturally occurring carotenoids described in the literature, and their stereo- and geometric isomers. Such analogs or derivatives may include, but are not limited to, esters, ethers, carbonates, amides, carbamates, phosphate esters and ethers, sulfates, glycoside ethers, with or without spacers (linkers).

As used herein the terms "the synergistic combination of more than one structural analog or derivative or synthetic intermediate of carotenoids" may be generally defined as any composition including one structural carotenoid analog or derivative or synthetic intermediate combined with one or more other structural carotenoid analogs or derivatives or synthetic intermediate or co-antioxidants, either as derivatives or in solutions and/or formulations.

In some embodiments, techniques described herein may be applied to the inhibition and/or amelioration of any disease or disease state related to reactive oxygen species ("ROS") and other radical and non-radical species.

In some embodiments, techniques described herein may be applied to the inhibition and/or amelioration of inflammation, including but not limited to ischemic reperfusion injury of a tissue.

An embodiment may include the administration of structural carotenoid analogs or derivatives or synthetic intermediates alone or in combination to a subject such that the occurrence of inflammation is thereby inhibited and/or ameliorated. The structural carotenoid analogs or derivatives or synthetic intermediates may be water-soluble and/or water dispersible derivatives. The carotenoid derivatives may include any substituent that substantially increases the water solubility of the naturally occurring carotenoid. The carotenoid derivatives may retain and/or improve the antioxidant properties of the parent carotenoid. The carotenoid derivatives may retain the non-toxic properties of the parent carotenoid. The carotenoid derivatives may have increased bioavailability, relative to the parent carotenoid, upon administration to a subject. The parent carotenoid may be naturally occurring.

Another embodiments may include the administration of a composition comprised of the synergistic combination of more than one structural analog or derivative or synthetic intermediate of carotenoids to a subject such that the occurrence of a proliferative disorder is thereby reduced. The composition may be a "racemic" (i.e. mixture of the potential stereoisomeric forms) mixture of carotenoid derivatives. Included as well are pharmaceutical compositions comprised of structural analogs or derivatives or synthetic intermediates of carotenoids in combination with a pharmaceutically acceptable carrier. In one embodiment, a pharmaceutically acceptable carrier may be serum albumin. In one embodiment, structural analogs or derivatives or synthetic intermediates of carotenoids may be complexed with human serum albumin (i.e., HSA) in a solvent. HSA may act as a pharmaceutically acceptable carrier.

In some embodiments, a single stereoisomer of a structural analog or derivative or synthetic intermediate of carotenoids may be administered to a human subject in order to ameliorate a pathological condition. Administering a single stereoisomer of a particular compound (e.g., as part of a pharmaceutical composition) to a human subject may be advantageous (e.g., increasing the potency of the pharmaceutical composition). Administering a single stereoisomer may be advantageous due to the fact that only one isomer of potentially many may be biologically active enough to have the desired effect.

In some embodiments, compounds described herein may be administered in the form of nutraceuticals. "Nutraceuticals" as used herein, generally refers to dietary supplements, foods, or medical foods that: 1. possess health benefits generally defined as reducing the risk of a disease or health condition, including the management of a disease or health condition or the improvement of health; and 2. are safe for human consumption in such quantity, and with such frequency, as required to realize such properties. Generally a nutraceutical is any substance that is a food or a part of a food and provides medical or health benefits, including the prevention and treatment of disease. Such products may range from isolated nutrients, dietary supplements and specific diets to genetically engineered designer foods, herbal products, and processed foods such as cereals, soups and beverages. It is important to note that this definition applies to all categories of food and parts of food, ranging from dietary supplements such as folic acid, used for the prevention of spina bifida, to chicken soup, taken to lessen the discomfort of the common cold. This definition also includes a bio-engineered designer vegetable food, rich in antioxidant ingredients, and a stimulant functional food or pharmafood. Within the context of the description herein where the composition, use and/or delivery of pharmaceuticals are described nutraceuticals may also be composed, used, and/or delivered in a similar manner where appropriate.

In some embodiments, compositions may include all compositions of 1.0 gram or less of a particular structural carotenoid analog, in combination with 1.0 gram or less of one or more other structural carotenoid analogs or derivatives or synthetic intermediates and/or co-antioxidants, in an amount which is effective to achieve its intended purpose. While individual subject needs vary, determination of optimal ranges of effective amounts of each component is with the skill of the art. Typically, a structural carotenoid analog or derivative or synthetic intermediates may be administered to mammals, in particular humans, orally at a dose of 5 to 100 mg per day referenced to the body weight of the mammal or human being treated for a particular disease. Typically, a structural carotenoid analog or derivative or synthetic intermediate may be administered to mammals, in particular humans, parenterally at a dose of between 5 to 1000 mg per day referenced to the body weight of the mammal or human being treated for a particular disease. In other embodiments, about 100 mg of a structural carotenoid analog or derivative or synthetic intermediate is either orally or parenterally administered to treat or prevent disease.

The unit oral dose may comprise from about 0.25 mg to about 1.0 gram, or about 5 to 25 mg, of a structural carotenoid analog. The unit parenteral dose may include from about 25 mg to 1.0 gram, or between 25 mg and 500 mg, of a structural carotenoid analog. The unit intracoronary dose may include from about 25 mg to 1.0 gram, or between 25 mg and 100 mg, of a structural carotenoid analog. The unit doses may be administered one or more times daily, on alternate days, in loading dose or bolus form, or titrated in a parenteral solution to commonly accepted or novel biochemical surrogate marker(s) or clinical endpoints as is with the skill of the art.

In addition to administering a structural carotenoid analog or derivative or synthetic intermediate as a raw chemical, the compounds may be administered as part of a pharmaceutical preparation containing suitable pharmaceutically acceptable carriers, preservatives, excipients and auxiliaries which facilitate processing of the structural carotenoid analog or derivative or synthetic intermediates which may be used pharmaceutically. The preparations, particularly those preparations which may be administered orally and which may be used for the preferred type of administration, such as tablets, softgels, lozenges, dragees, and capsules, and also preparations which may be administered rectally, such as suppositories, as well as suitable solutions for administration by injection or orally or by inhalation of aerosolized preparations, may be prepared in dose ranges that provide similar bioavailabihty as described above, together with the excipient. While individual needs may vary, determination of the optimal ranges of effective amounts of each component is within the skill of the art.

The pharmaceutical preparations may be manufactured in a manner which is itself known to one skilled in the art, for example, by means of conventional mixing, granulating, dragee-making, softgel encapsulation, dissolving, extracting, or lyophilizing processes. Thus, pharmaceutical preparations for oral use may be obtained by combining the active compounds with solid and semi-solid excipients and suitable preservatives, and/or co-antioxidants. Optionally, the resulting mixture may be ground and processed. The resulting mixture of granules may be used, after adding suitable auxiliaries, if desired or necessary, to obtain tablets, softgels, lozenges, capsules, or dragee cores.

Suitable excipients may be fillers such as saccharides (e.g., lactose, sucrose, or mannose), sugar alcohols (e.g., mannitol or sorbitol), cellulose preparations and/or calcium phosphates (e.g., tricalcium phosphate or calcium hydrogen phosphate). In addition binders may be used such as starch paste (e.g., maize or corn starch, wheat starch, rice starch, potato starch, gelatin, tragacanth, methyl cellulose, hydroxypropylmethylcellulose, sodium carboxymethylcellulose, and/or polyvinyl pyrrolidone). Disintegrating agents may be added (e.g., the above-mentioned starches) as well as carboxymethyl-starch, cross-linked polyvinyl pyrrolidone, agar, or alginic acid or a salt thereof (e.g., sodium alginate). Auxiliaries are, above all, flow-regulating agents and lubricants (e.g., silica, talc, stearic acid or salts thereof, such as magnesium stearate or calcium stearate, and/or polyethylene glycol, or PEG). Dragee cores are provided with suitable coatings, which, if desired, are resistant to gastric juices. Softgelatin capsules ("softgels") are provided with suitable coatings, which, typically, contain gelatin and/or suitable edible dye(s). Animal component-free and kosher gelatin capsules may be particularly suitable for the embodiments described herein for wide availability of usage and consumption. For this purpose, concentrated saccharide solutions may be used, which may optionally contain gum arabic, talc, polyvinyl pyrrolidone, polyethylene glycol (PEG) and/or titanium dioxide, lacquer solutions and suitable organic solvents or solvent mixtures, including dimethylsulfoxide (DMSO), tetrahydrofuran (THF), acetone, ethanol, or other suitable solvents and co-solvents. In order to produce coatings resistant to gastric juices, solutions of suitable cellulose preparations such as acetylcellulose phthalate or hydroxypropylmethylcellulose phthalate, may be used. Dye stuffs or pigments may be added to the tablets or dragee coatings or softgelatin capsules, for example, for identification or in order to characterize combinations of active compound doses, or to disguise the capsule contents for usage in clinical or other studies.

Other pharmaceutical preparations that may be used orally include push-fit capsules made of gelatin, as well as soft, thermally sealed capsules made of gelatin and a plasticizer such as glycerol or sorbitol. The push-fit capsules may contain the active compounds in the form of granules that may be mixed with fillers such as, for example, lactose, binders such as starches, and/or lubricants such as talc or magnesium stearate and, optionally, stabilizers and/or preservatives. In soft capsules, the active compounds may be dissolved or suspended in suitable liquids, such as fatty oils such as rice bran oil or peanut oil or palm oil, or liquid paraffin. In some embodiments, stabilizers and preservatives may be added.

In some embodiments, pulmonary administration of a pharmaceutical preparation may be desirable. Pulmonary administration may include, for example, inhalation of aerosolized or nebulized liquid or solid particles of the pharmaceutically active component dispersed in and surrounded by a gas.

Possible pharmaceutical preparations, which may be used rectally, include, for example, suppositories, which consist of a combination of the active compounds with a suppository base. Suitable suppository bases are, for example, natural or synthetic triglycerides, or paraffin hydrocarbons. In addition, it is also possible to use gelatin rectal capsules that consist of a combination of the active compounds with a base. Possible base materials include, for example, liquid triglycerides, polyethylene glycols, or paraffin hydrocarbons.

Suitable formulations for parenteral administration include, but are not limited to, aqueous solutions of the active compounds in water-soluble and/or water dispersible form, for example, water-soluble salts, esters, carbonates, phosphate esters or ethers, sulfates, glycoside ethers, together with spacers and/or linkers. Suspensions of the active compounds as appropriate oily injection suspensions may be administered, particularly suitable for intramuscular injection. Suitable lipophilic solvents, co-solvents (such as DMSO or ethanol), and/or vehicles including fatty oils, for example, rice bran oil or peanut oil and/or palm oil, or synthetic fatty acid esters, for example, ethyl oleate or triglycerides, may be used. Aqueous injection suspensions may contain substances that increase the viscosity of the suspension including, for example, sodium carboxymethyl cellulose, sorbitol, dextran, and/or cyclodextrins. Cyclodextrins (e.g., β-cyclodextrin) may be used specifically to increase the water solubility for parenteral injection of the structural carotenoid analog. Liposomal formulations, in which mixtures of the structural carotenoid analog or derivative with, for example, egg yolk phosphotidylcholine (E-PC), may be made for injection. Optionally, the suspension may contain stabilizers, for example, antioxidants such as BHT, and/or preservatives, such as benzyl alcohol.

EXAMPLES

Having now described the invention, the same will be more readily understood through reference to the following example(s), which are provided by way of illustration, and are not intended to be limiting of the present invention.

General. Natural source lutein (90%) was obtained from ChemPacific, Inc. (Baltimore, Md.) as a red-orange solid and was used without further purification. All other reagents and solvents used were purchased from Acros (New Jersey, USA) and were used without further purification. All reactions were performed under $N_2$ atmosphere. All flash chromatographic purifications were performed on Natland International Corporation 230-400 mesh silica gel using the indicated solvents. LC/MS (APCI) and LC/MS (ESI) were recorded on an Agilent 1100 LC/MSD VL system; column: Zorbax Eclipse XDB-C18 Rapid Resolution (4.6×75 mm, 3.5 μm, USUT002736); temperature: 25° C.; starting pressure: 105 bar; flow rate: 1.0 mL/min; mobile phase (% A=0.025% trifluoroacetic acid in $H_2O$, % B=0.025% trifluoroacetic acid in acetonitrile) Gradient program: 70% A/30% B (start), step gradient to 50% B over 5 min, step gradient to 98% B over 8.30 min, hold at 98% B over 25.20 min, step gradient to 30% B over 25.40 min; PDA Detector: 470 nm. The presence of trifluoroacetic acid in the LC eluents acts to protonate synthesized lutein disuccinate and diphosphate salts to give the free di-acid forms, yielding $M^+$=768 for the disuccinate salt sample and $M^+$=728 for the diphosphate salt sample in MS analyses. LRMS: +mode; ESI: electrospray chemical ionization, ion collection using quadrapole; APCI: atmospheric pressure chemical ionization, ion collection using quadrapole. MS (ESI-IT) was recorded on a HCT plus Bruker Daltonics Mass Spectrometer system, LRMS: +mode; ESI-IT: electrospray chemical ionization, ion collection using ion trap. $^1$H NMR analyses were attempted on Varian spectrometers (300 and 500 MHz). NMR analyses of natural source lutein as well as synthesized lutein derivatives yielded only partially discernable spectra, perhaps due to the presence of interfering impurities (natural source lutein), or due to aggregation (natural source lutein and derivatives). In attempts to circumvent the problems associated with NMR analyses, samples were prepared using mixtures of deuterated solvents including methanol/chloroform, methanol/water, methyl sulfoxide/water, and chloroform/methanol/water. However, such attempts failed to give useful data.

Natural source lutein (β,ε-carotene-3,3'-diol), 1. LC/MS (ESI): 9.95 min (2.78%), $\lambda_{max}$ 226 nm (17%), 425 nm (100%); 10.58 min (3.03%), $\lambda_{max}$ 225 nm (21%), 400 nm (100%); 11.10 min (4.17%), $\lambda_{max}$ 225 nm (16%), 447 nm (100%); 12.41 min (90.02%), $\lambda_{max}$ 269 nm (14%), 447 nm (100%), m/z 568 $M^+$ (69%), 551 $[M-H_2O+H]^+$ (100%), 533 $[M-2H_2O+H]^+$ (8%)

β,ε-carotenyl 3,3'-disuccinate, 2. To a solution of natural source lutein (1) (0.50 g, 0.879 mmol) in $CH_2Cl_2$ (8 mL) was added N,N-diisopropylethylamine (3.1 mL, 17.58 mmol) and succinic anhydride (0.88 g, 8.79 mmol). The solution was stirred at RT overnight and then diluted with $CH_2Cl_2$ and quenched with water/1 M HCl (5/1). The aqueous layer was extracted two times with $CH_2Cl_2$ and the combined organic layer was washed three times with cold water/1 M HCl (5/1), dried over $Na_2SO_4$, and concentrated. The resulting red-orange oil was washed (slurried) three times with hexanes to yield disuccinate 2 (0.433 g, 64%) as a red-orange solid; LC/MS (APCI): 10.37 min (4.42%), $\lambda_{max}$ 227 nm (56%), 448 nm (100%), m/z 769 $[M+H]^+$ (8%), 668 $[M-C_4O_3H_4]^+$ (9%), 637 (36%), 138 (100%); 11.50 min (92.40%), $\lambda_{max}$ 269 nm (18%), 447 nm (100%), m/z 769 $[M+H]^+$ (7%), 668 $[M-C_4O_3H_4]^+$ (9%), 651 (100%); 12.03 min (3.18%) $\lambda_{max}$ 227 nm (55%), 446 nm (100%), m/z 668 $[M-C_4O_3H_4]^+$ (15%), 550 (10%), 138 (100%)

β,ε-carotenyl 3,3'-disuccinate sodium salt, 3. To a solution of disuccinate 2 (0.32 g, 0.416 mmol) in $CH_2Cl_2$/methanol (5 mL/1 mL) at 0° C. was added drop-wise sodium methoxide (25% wt in methanol; 0.170 mL, 0.748 mmol). The solution was stirred at RT overnight and then quenched with water and stirred for 5 min. The solution was then concentrated and the aqueous layer was washed four times with $Et_2O$. Lyophilization of the clear, red-orange aqueous solution yielded 3 (0.278 g, 91%) as an orange, hygroscopic solid; LC/MS (APCI): 11.71 min (94.29%), $\lambda_{max}$ 269 nm (18%), 446 nm (100%), m/z 769 $[M-2Na+3H]^+$ (8%), 668 $[M-2Na+2H-C_4O_3H_4]^+$ (6%), 651 (100%); 12.74 min (5.71%), $\lambda_{max}$ 227 nm (30%), 269 nm (18%), 332 nm (39%), 444 nm (100%), m/z 768 $[M-2Na+2H]^+$ (2%), 668 $[M-2Na+2H-C_4O_3H_4]^+$ (3%), 651 (12%), 138 (100%)

Tribenzyl phosphite, 4. To a well-stirred solution of phosphorus trichloride (1.7 mL, 19.4 mmol) in $Et_2O$ (430 mL) at 0° C. was added dropwise a solution of triethylamine (8.4 mL, 60.3 mmol) in $Et_2O$ (20 mL), followed by a solution of benzyl alcohol (8.1 mL, 77.8 mmol) in $Et_2O$ (20 mL). The mixture was stirred at 0° C. for 30 min and then at RT overnight. The mixture was filtered and the filtrate concentrated to give a colorless oil. Silica chromatography (hexanes/$Et_2O$/triethylamine, 4/1/1%) of the crude product yielded 4 (5.68 g, 83%) as a clear, colorless oil that was stored under $N_2$ at −20° C.; $^1H$ NMR: δ 7.38 (15H, m), 4.90 (6H, d)

Dibenzyl phosphoroiodidate, 5. To a solution of tribenzyl phosphite (5.43 g, 15.4 mmol) in $CH_2Cl_2$ (8 mL) at 0° C. was added $I_2$ (3.76 g, 14.8 mmol). The mixture was stirred at 0° C. for 10 min or until the solution became clear and colorless. The solution was then stirred at RT for 10 min and used directly in the next step.

3-(Bis benzyl-phosphoryloxy)-3'-(phosphoryloxy)-β,ε-carotene, 6. To a solution of natural source lutein (1) (0.842 g, 1.48 mmol) in $CH_2Cl_2$ (8 mL) was added pyridine (4.8 mL, 59.2 mmol). The solution was stirred at 0° C. for 5 min and then freshly prepared 5 (14.8 mmol) in $CH_2Cl_2$ (8 mL) was added drop-wise to the mixture at 0° C. The solution was stirred at 0° C. for 1 h and then diluted with $CH_2Cl_2$ and quenched with brine. The aqueous layer was extracted twice with $CH_2Cl_2$ and the combined organic layer was washed once with brine, then dried over $Na_2SO_4$ and concentrated. Pyridine was removed from the crude red oil by azeotropic distillation using toluene. The crude product was alternately washed (slurried) twice with hexanes and $Et_2O$ to yield 6 as a red oil, used in the next step without further purification; LC/MS (ESI): 9.93 min (44.78%), $\lambda_{max}$ 267 nm (33%), 444 nm (100%), m/z 890 $[M-H_2O]^+$ (8%), 811 $[M-PO_3H-H_2O+H]^+$ (73%), 533 (100%); 9.99 min (29.0%), $\lambda_{max}$ 268 nm (24%), 446 nm (100%), m/z 890 $[M-H_2O]^+$ (6%), 811 $[M-PO_3H-H_2O+H]^+$ (72%), 533 (100%); 10.06 min (26.23%), $\lambda_{max}$ 266 nm (15%), 332 nm (22%), 444 nm (100%), m/z 890 $[M-H_2O]^+$ (5%), 811 $[M-PO_3H-H_2O+H]^+$ (90%), 533 (100%)

3-(Bis benzyl-phosphoryloxy)-3'-hydroxy-β,ε-carotene, 7. To a solution of 6 (0.033 mmol) in tetrahydrofuran/water (1 mL/0.5 mL) at 0° C. was added $LiOH-H_2O$ (0.003 g, 0.073 mmol). The solution was stirred at RT for 1 h and then quenched with methanol. The crude reaction mixture was analyzed by LC/MS; LC/MS (ESI): 10.02 min (40.60%), $\lambda_{max}$ 266 nm (12%), 333 nm (25%), 445 nm (100%), m/z 890 $[M-H_2O]^+$ (33%), 811 $[M-PO_3H-H_2O+H]^+$ (50%), 533 (100%); 16.37 min (49.56%) λmax 267 nm (16%), 332 nm (27%), 446 nm (100%), m/z 828 $M^+$ (55%), 550 (44%)

3,3'-Diphosphoryloxy-β,ε-carotene, 8. To a solution of 6 (1.48 mmol) in $CH_2Cl_2$ (10 mL) at 0° C. was added drop-wise N,O-bis(trimethylsilyl)acetamide (3.7 mL, 14.8 mmol) and then bromotrimethylsilane (1.56 mL, 11.8 mmol). The solution was stirred at 0° C. for 1 h, quenched with methanol, diluted with $CH_2Cl_2$, and then concentrated. The resulting red oil was alternately washed (slurried) three times with ethyl acetate and $CH_2Cl_2$ to yield crude phosphate 8 (2.23 g) as a dark orange oil, used in the next step without further purification; LC/MS (ESI): 8.55 min (45.67%), $\lambda_{max}$ 214 nm (25%), 268 nm (28%), 447 nm (100%), m/z 631 $[M-PO_3H-H_2O+H]^+$ (30%), 533 (18%), 279 (13%), 138 (87%); 8.95 min (35.0%), $\lambda_{max}$ 217 mm (14%), 268 nm (23%), 448 nm (100%), m/z 631 $[M-PO_3H-H_2O+H]^+$ (26%), 533 (32%), 279 (18%), 138 (100%); 9.41 min (9.70%), $\lambda_{max}$ 225 nm (37%), 269 nm (23%), 335 nm (19%), 447 nm (100%), m/z 631 $[M-PO_3H-H_2O+H]^+$ (6%), 533 (18%), 279 (13%), 138 (100%)

3,3'-Diphosphoryloxy-β,ε-carotene sodium salt, 9. To a solution of crude 8 (ca 50%; 2.23 g, 3.06 mmol) in methanol (20 mL) at 0° C. was added drop-wise sodium methoxide (25%; 3.5 mL, 15.3 mmol). The solution was stirred at RT for 2 h and the resulting orange solid was washed (slurried) three times with methanol. Water was added to the moist solid and the resulting aqueous layer was extracted with $CH_2Cl_2$, ethyl acetate, and again with $CH_2Cl_2$. Lyophilization of the clear, red-orange aqueous solution yielded 9 (0.956 g, 80% over 3 steps) as an orange, hygroscopic solid; LC/MS (ESI): 7.81 min (22.34%), $\lambda_{max}$ 215 nm (34%), 268 nm (30%), 448 nm (100%), m/z 711 $[M-4Na-H_2O+5H]^+$ (9%), 533 (13%), 306 (100%); 8.33 min (39.56%), $\lambda_{max}$ 217 nm (14%), 268 nm (20%), 448 nm (100%), m/z 711 $[M-4Na-H_2O+5H]^+$ (10%), 533 (11%), 306 (100%); 8.90 min (38.09%), $\lambda_{max}$ 223 nm (45%), 269 nm (30%), 336 nm (26%), 448 nm (100%), m/z 711 $[M-4Na-H_2O+5H]^+$ (8%), 631 $[M-4Na-PO_3H-H_2O+5H]^+$ (18%), 533 (20%), 306 (100%); MS (ESI-IT): m/z 816 $M^+$ (55%), 772 $[M-2Na+2H]^+$ (37%), 728 $[M-4Na+4H]^+$ (74%)

Figure 5:
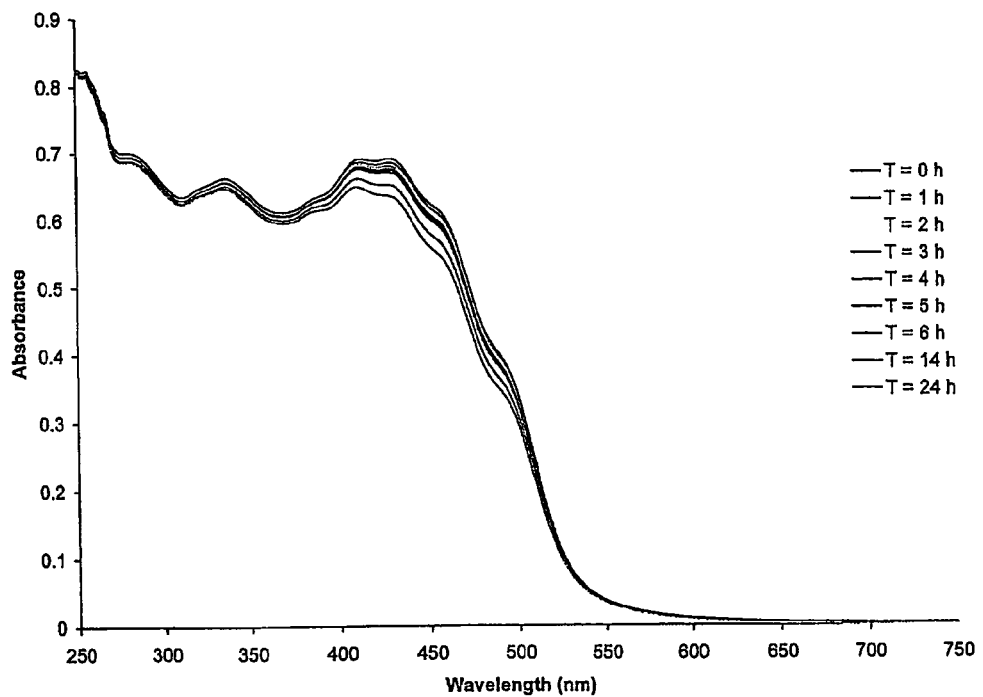
FIG. 5 is a depiction of a time series of the UV/V is absorption spectra of the disodium diphosphate derivative of natural source lutein in water.
Figure 6:
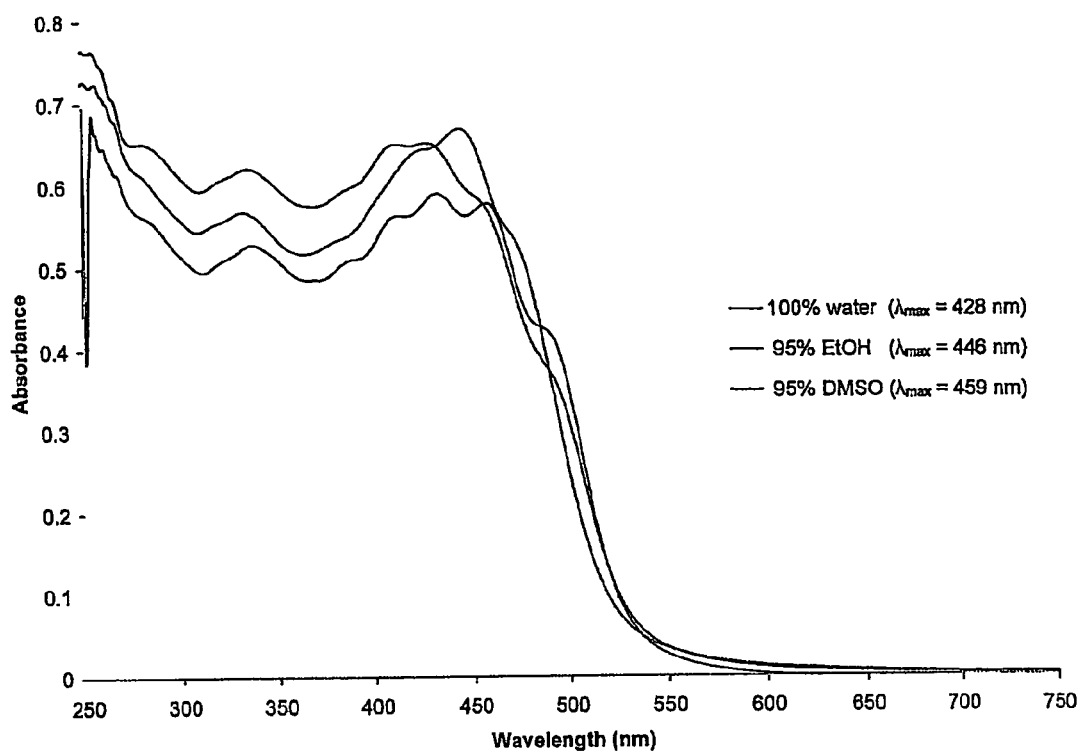
FIG. 6 is a depiction of a UV/V is absorption spectra of the disodium diphosphate derivative of natural source lutein in 95% ethanol ($\lambda_{max}$=446 nm), 95% DMSO ($\lambda_{max}$=459 nm), and water ($\lambda_{max}$=428 nm).
Figure 7:
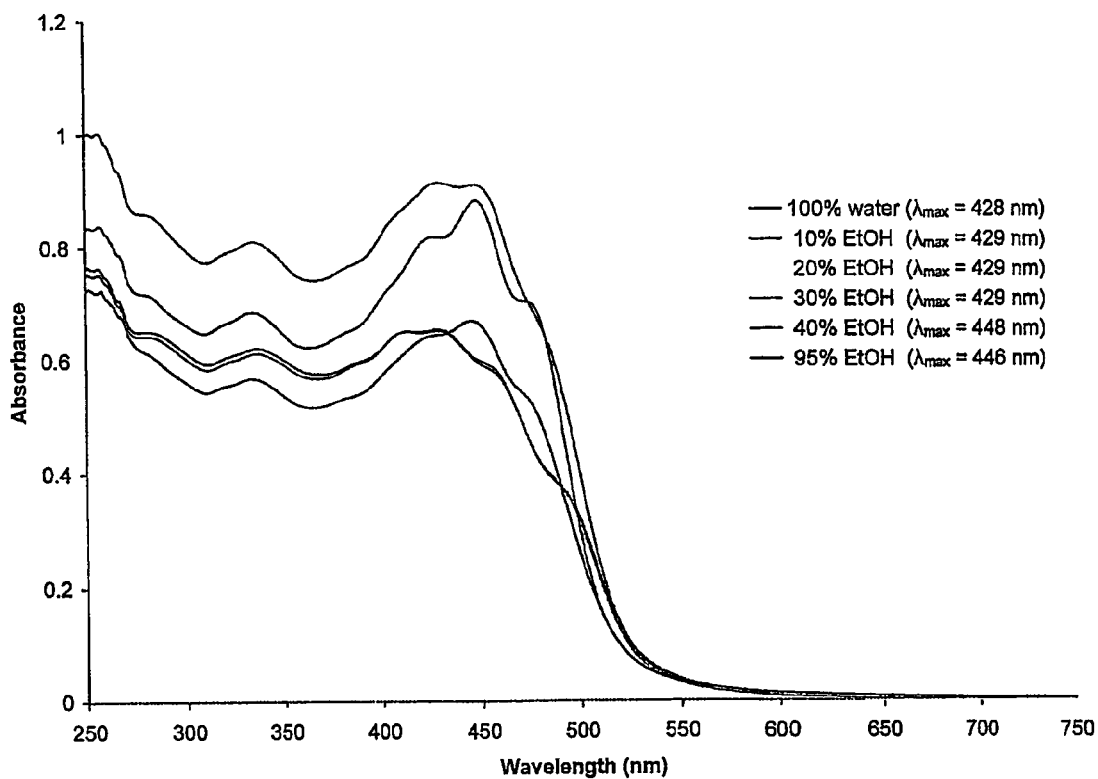
FIG. 7 is a depiction of a UV/V is absorption spectra of the disodium diphosphate derivative of natural source lutein in water ($\lambda_{max}$=428 nm) with increasing concentrations of ethanol.

UV/Visible spectroscopy. For spectroscopic sample preparations, 3 and 9 were dissolved in the appropriate solvent to yield final concentrations of approximately 0.01 mM and 0.2 mM, respectively. The solutions were then added to a rectangular cuvette with 1 cm path length fitted with a glass stopper. The absorption spectrum was subsequently registered between 250 and 750 nm. All spectra were accumulated one time with a bandwidth of 1.0 nm at a scan speed of 370 nm/min. For the aggregation time-series measurements, spectra were obtained at baseline (immediately after solvation; time zero) and then at the same intervals up to and including 24 hours post-solvation (see FIG. 2-FIG. 7). Concentration was held constant in the ethanolic titration of the diphosphate lutein sodium salt, for which evidence of card-pack aggregation was obtained (FIG. 5-FIG. 7).

Determination of aqueous solubility/dispersibility. 30.13 mg of 3 was added to 1 mL of USP-purified water. The sample was rotated for 2 hours, then centrifuged for 5 minutes. After centrifuging, solid was visible in the bottom of the tube. A 125-μL aliquot of the solution was then diluted to 25 mL. The sample was analyzed by UV/Vis spectroscopy at 436 nm, and the absorbance was compared to a standard curve compiled from 4 standards of known concentration. The concentration of the original supernatant was calculated to be 2.85 mg/mL and the absorptivity was 36.94 AU*mL/cm*mg. Slight error may have been introduced by the small size of the original aliquot.

Next, 30.80 mg of 9 was added to 1 mL of USP-purified water. The sample was rotated for 2 hours, then centrifuged for 5 minutes. After centrifuging, solid was visible in the bottom of the tube. A 125-μL aliquot of the solution was then diluted to 25 mL. The sample was analyzed by UV/Vis spectroscopy at 411 nm, and the absorbance was compared to a standard curve compiled from 4 standards of known concentration. The concentration of the original supernatant was calculated to be 29.27 mg/mL and the absorptivity was 2.90 AU*mL/cm*mg. Slight error may have been introduced by the small size of the original aliquot.

Leukocyte Isolation and Preparation. Human polymorphonuclear leukocytes (PMNs) were isolated from freshly sampled venous blood of a single volunteer (S.F.L.) by Percoll density gradient centrifugation as described previously. Briefly, each 10 mL of whole blood was mixed with 0.8 mL of 0.1 M EDTA and 25 mL of saline. The diluted blood was then layered over 9 mL of Percoll at a specific density of 1.080 g/mL. After centrifugation at 400×g for 20 min at 20° C., the plasma, mononuclear cell, and Percoll layers were removed. Erythrocytes were subsequently lysed by addition of 18 mL of ice-cold water for 30 s, followed by 2 mL of 10× PIPES buffer (25 mM PIPES, 110 mM NaCl, and 5 mM KCl, titrated to pH 7.4 with NaOH). Cells were then pelleted at 4° C., the supernatant was decanted, and the procedure was repeated. After the second hypotonic cell lysis, cells were washed twice with PAG buffer [PIPES buffer containing 0.003% human serum albumin (HSA) and 0.1% glucose]. Afterward, PMNs were counted by light microscopy on a hemocytometer. The isolation yielded PMNs with a purity of >95%. The final pellet was then suspended in PAG-CM buffer (PAG buffer with 1 mM $CaCl_2$ and 1 mM $MgCl_2$).

EPR Measurements. All EPR measurements were performed using a Bruker ER 300 EPR spectrometer operating at X-band with a $TM_{110}$ cavity as previously described. The microwave frequency was measured with a Model 575 microwave counter (EIP Microwave, Inc., San Jose, Calif.). To measure superoxide anion ($O_2$) generation from phorbol-ester (PMA)-stimulated PMNs, EPR spin-trapping studies were performed using the spin trap DEPMPO (Oxis, Portland, Oreg.) at 10 mM. $1\times10^6$ PMNs were stimulated with PMA (1 ng/mL) and loaded into capillary tubes for EPR measurements. To determine the radical scavenging ability of 3 and 9 in aqueous and ethanolic formulations, PMNs were pre-incubated for 5 minutes with test compound, followed by PMA stimulation.

Instrument settings used in the spin-trapping experiments were as follows: modulation amplitude, 0.32 G; time constant, 0.16 s; scan time, 60 s; modulation frequency, 100 kHz; microwave power, 20 milliwatts; and microwave frequency, 9.76 GHz. The samples were placed in a quartz EPR flat cell, and spectra were recorded. The component signals in the spectra were identified and quantified as reported previously.

UV/Vis Spectral Properties in Organic and Aqueous Solvents.

Figure 2:
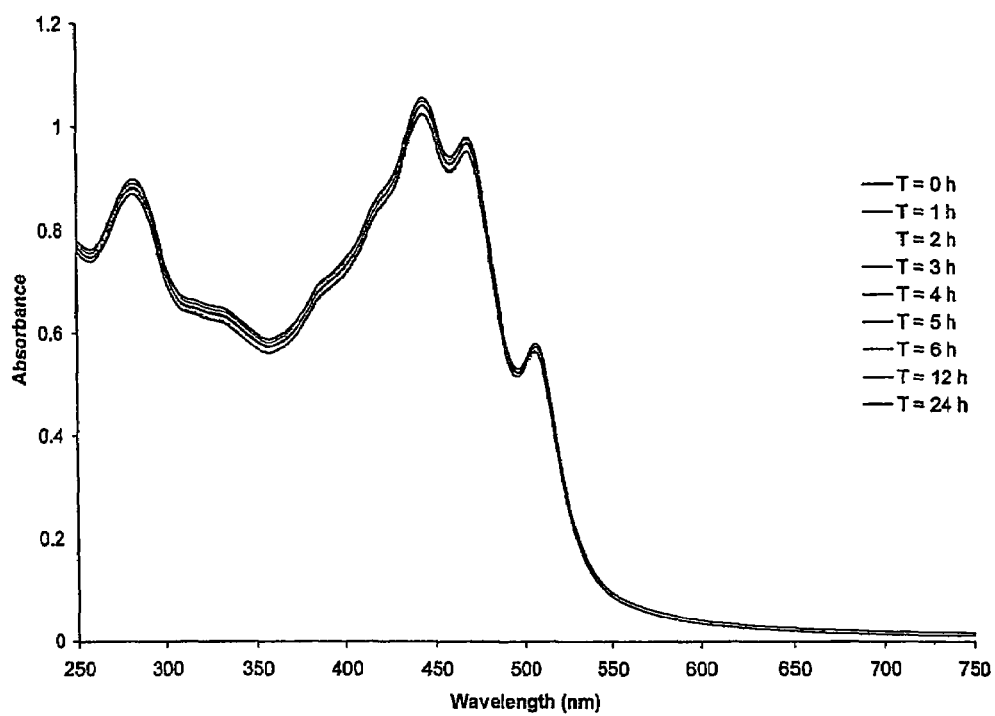
FIG. 2 is a depiction of a time series of the UV/V is absorption spectra of the disodium disuccinate derivative of natural source lutein in water.
Figure 3:
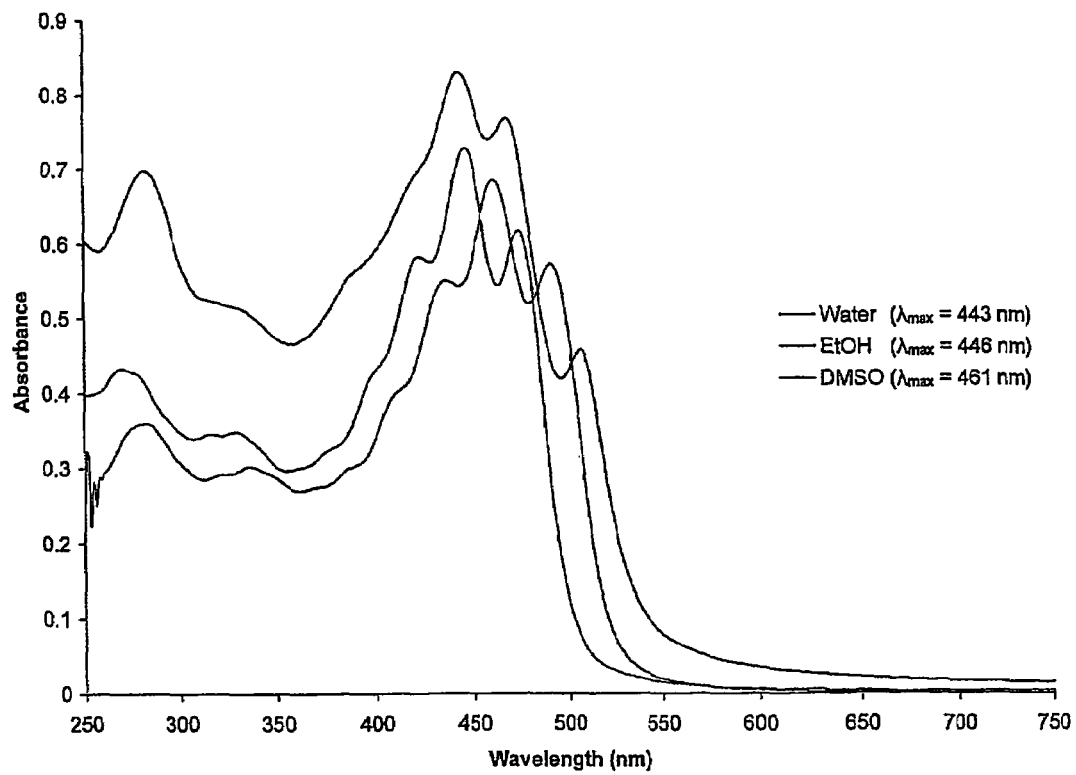
FIG. 3 is a depiction of a UV/V is absorption spectra of the disodium disuccinate derivative of natural source lutein in water ($\lambda_{max}$=443 nm), ethanol ($\lambda_{max}$=446 nm), and DMSO ($\lambda_{max}$=461 nm).
Figure 4:
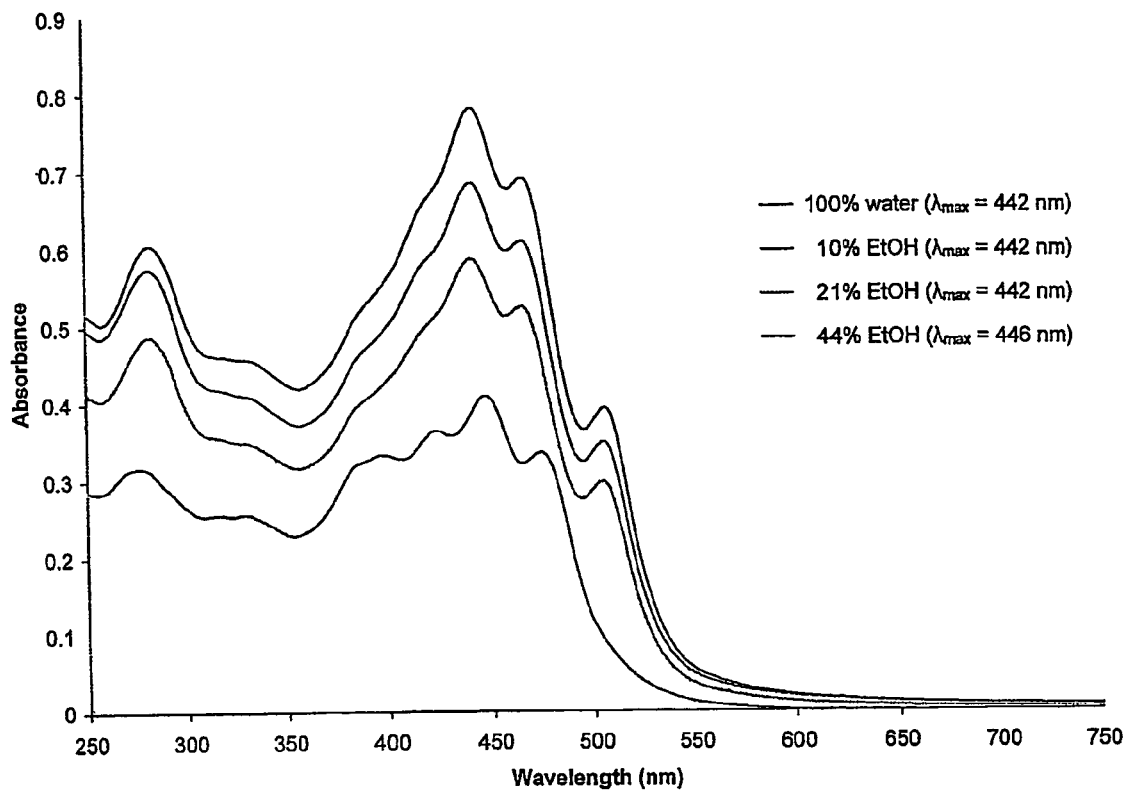
FIG. 4 is a depiction of a UV/V is absorption spectra of the disodium disuccinate derivative of natural source lutein in water ($\lambda_{max}$=442 m-n) with increasing concentrations of ethanol.

UV-Vis spectral evaluation of the disuccinate lutein sodium salt is depicted in FIG. 2-FIG. 4. FIG. 2 depicts a time series of the UV/Vis absorption spectra of the disodium disuccinate derivative of natural source lutein in water. The $\lambda_{max}$ (443 nm) obtained at time zero did not appreciably blue-shift over the course of 24 hours, vibrational fine structure was maintained (% III/II=35%), and the spectra became only slightly hypochromic (i.e. decreased in absorbance intensity) over time, indicating minimal time-dependent supramolecular assembly (aggregation) of the card-pack type during this time period. Existence of head-to-tail (J-type) aggregation in solution cannot be ruled out.

FIG. 3 depicts a UV/Vis absorption spectra of the disodium disuccinate derivative of natural source lutein in water ($\lambda_{max}$=443 nm), ethanol ($\lambda_{max}$=446 nm), and DMSO ($\lambda_{max}$=461 nm). Spectra were obtained at time zero. A prominent cis peak is seen with a maximum at 282 nm in water. The expected bathochromic shift of the spectrum in the more polarizable solvent (DMSO) is seen (461 nm). Only a slight hypsochromic shift is seen between the spectrum in water and that in ethanol, reflecting minimal card-pack aggregation in aqueous solution. Replacement of the main visible absorption band observed in EtOH by an intense peak in the near UV region-narrow and displaying no vibrational fine structure—is not observed in the aqueous solution of this highly water-dispersible derivative, in comparison to the spectrum of pure lutein in an organic/water mixture.

FIG. 4 depicts a UV/Vis absorption spectra of the disodium disuccinate derivative of natural source lutein in water ($\lambda_{max}$=442 nm) with increasing concentrations of ethanol. The $\lambda_{max}$ increases to 446 nm at an EtOH concentration of 44%, at which point no further shift of the absorption maximum occurs (i.e. a molecular solution has been achieved), identical to that obtained in 100% EtOH (See FIG. 3).

UV-Vis spectral evaluation of the diphosphate lutein sodium salt is depicted in FIG. 5-FIG. 7. FIG. 5 depicts a time series of the UV/Vis absorption spectra of the disodium diphosphate derivative of natural source lutein in water. Loss of vibrational fine structure (spectral distribution beginning to approach unimodality) and the blue-shifted lambda max relative to the lutein chromophore in EtOH suggested that card-pack aggregation was present immediately upon solvation. The $\lambda_{max}$ (428 nm) obtained at time zero did not appreciably blue-shift over the course of 24 hours, and the spectra became slightly more hypochromic over time (i.e. decreased in absorbance intensity), indicating additional time-dependent supramolecular assembly (aggregation) of the card-pack type during this time period. This spectrum was essentially maintained over the course of 24 hours (compare with FIG. 2, disuccinate lutein sodium salt).

FIG. 6 depicts a UV/Vis absorption spectra of the disodium diphosphate derivative of natural source lutein in 95% ethanol ($\lambda_{max}$=446 nm), 95% DMSO ($\lambda_{max}$=459 nm), and water ($\lambda_{max}$=428 nm). A red-shift was observed ($\lambda_{max}$ to 446 nm), as was observed with the disuccinate derivate. Wetting of the diphosphate lutein derivative with a small amount of water was required to obtain appreciable solubility in organic solvent (e.g. EtOH and DMSO). Spectra were obtained at time zero. The expected bathochromic shift (in this case to 459 nm) of the spectrum in the more polarizable solvent (95% DMSO) is seen. Increased vibrational fine structure and red-shifting of the spectra were observed in the organic solvents.

FIG. 7 depicts a UV/Vis absorption spectra of the disodium diphosphate derivative of natural source lutein in water ($\lambda_{max}$=428 nm) with increasing concentrations of ethanol. Concentration of the derivative was held constant for each increased concentration of EtOH in solution. The $\lambda_{max}$ increases to 448 nm at an EtOH concentration of 40%, at which no further shift of the absorption maximum occurs (i.e. a molecular solution is reached).

Direct Superoxide Anion Scavenging by EPR Spectroscopy

Figure 8:
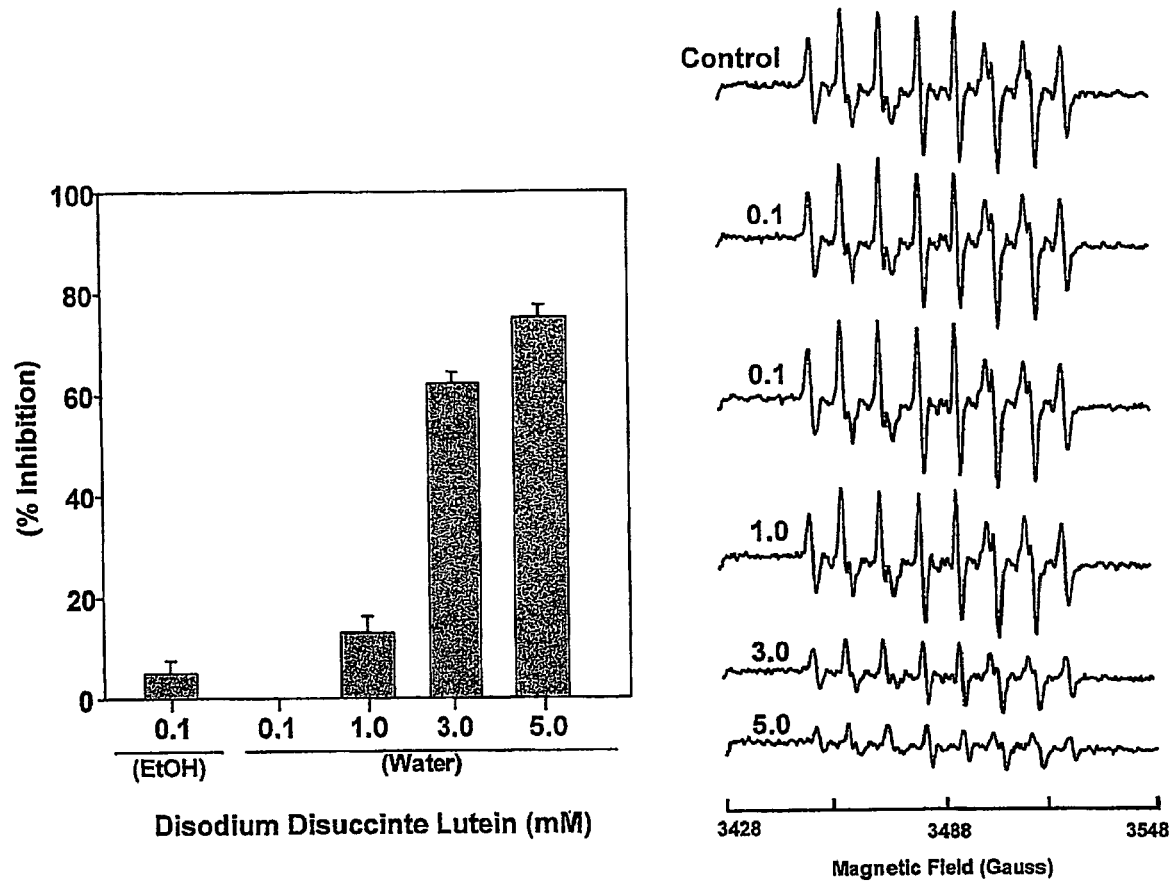
FIG. 8 is a depiction of a mean percent inhibition (±SEM) of superoxide anion signal as detected by DEPMPO spin-trap by the disodium disuccinate derivative of natural source lutein (tested in water).

The mean percent inhibition of superoxide anion signal (±SEM) as detected by DEPMPO spin-trap by the disodium disuccinate derivative of natural source lutein (tested in water) is shown in FIG. 8. A 100 μM formulation (0.1 mM) was also tested in 40% EtOH, a concentration shown to produce a molecular (i.e. non-aggregated) solution. As the concentration of the derivative increased, inhibition of superoxide anion signal increased in a dose-dependent manner. At 5 mM, approximately ¾ (75%) of the superoxide anion signal was inhibited. No significant scavenging (0% inhibition) was observed at 0.1 mM in water. Addition of 40% EtOH to the derivative solution at 0.1 mM did not significantly increase scavenging over that provided by the EtOH vehicle alone (5% inhibition). The millimolar concentration scavenging by the derivative was accomplished in water alone, without the addition of organic co-solvent (e.g., acetone, EtOH), heat, detergents, or other additives. This data suggested that card-pack aggregation for this derivative was not occurring in aqueous solution (and thus limiting the interaction of the aggregated carotenoid derivative with aqueous superoxide anion).

Figure 9:
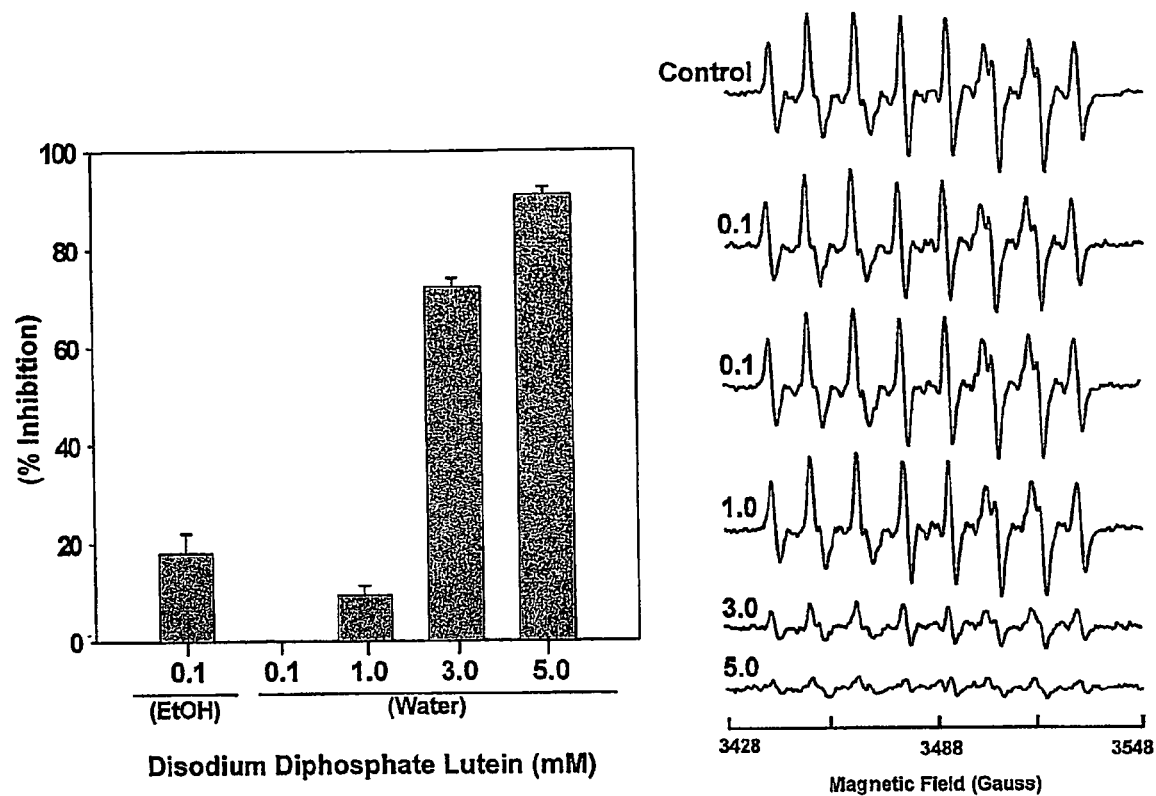
FIG. 9 is a depiction of a mean percent inhibition (±SEM) of superoxide anion signal as detected by DEPMPO spin-trap by the disodium diphosphate derivative of natural source lutein (tested in water).

The mean percent inhibition of superoxide anion signal (±SEM) as detected by DEPMPO spin-trap by the disodium diphosphate derivative of natural source lutein (tested in water) is shown in FIG. 9. A 100 μM formulation (0.1 mM) was also tested in 40% EtOH, a concentration also shown to produce a molecular (i.e. non-aggregated) solution of this derivative. As the concentration of the derivative increased, inhibition of the superoxide anion signal increased in a dose-dependent manner. At 5 mM, slightly more than 90% of the superoxide anion signal was inhibited (versus 75% for the disuccinate lutein sodium salt). As for the disuccinate lutein sodium salt, no apparent scavenging (0% inhibition) was observed at 0.1 mM in water. However, a significant increase over background scavenging by the EtOH vehicle (5%) was observed after the addition of 40% EtOH, resulting in a mean 18% inhibition of superoxide anion signal. This suggested that disaggregation of the compound lead to an increase in scavenging ability by this derivative, pointing to slightly increased scavenging ability of molecular solutions of the more water-dispersible diphosphate derivative relative to the disuccinate derivative. Again, the millimolar concentration scavenging by the derivative was accomplished in water alone, without the addition of organic co-solvent (e.g., acetone, EtOH), heat, detergents, or other additives.

TABLE 1

Descriptive statistics of mean % inhibition of superoxide anion signal for aqueous and ethanolic (40%) formulations of disodium disuccinate derivatives of natural source lutein tested in the current study. Sample sizes of 3 were evaluated for each formulation, with the exception of natural source lutein in 40% EtOH stock solution (N = 1). Mean % inhibition did not increase over background levels until sample concentration reached 1 mM in water; likewise, addition of 40% EtOH at the 0.1 mM concentration did not increase scavenging over background levels attributable to the EtOH vehicle (mean = 5% inhibition).

| Sample | Solvent | Concentration | N | Mean (% inhibition) | S.D. | SEM | Min | Max | Range |
|---|---|---|---|---|---|---|---|---|---|
| Lutein Disuccinate Sodium Salt | 40% EtOH | 0.1 mM | 3 | 5.0 | 4.4 | 2.5 | 0 | 8 | 8 |
| Lutein Disuccinate Sodium Salt | Water | 0.1 mM | 1 | 0.0 | ND | ND | 0 | 0 | 0 |
| Lutein Disuccinate Sodium Salt | Water | 1.0 mM | 3 | 13.0 | 5.6 | 3.2 | 8 | 19 | 11 |
| Lutein Disuccinate Sodium Salt | Water | 3.0 mM | 3 | 61.7 | 4.0 | 2.3 | 58 | 66 | 8 |
| Lutein Disuccinate Sodium Salt | Water | 5.0 mM | 3 | 74.7 | 4.5 | 2.6 | 70 | 79 | 9 |

TABLE 2

Descriptive statistics of mean % inhibition of superoxide anion signal for aqueous and ethanolic (40%) formulations of disodium diphosphate derivatives of natural source lutein tested in the current study. Sample sizes of 3 were evaluated for each formulation, with the exception of lutein diphosphate in water at 100 μM (0.1 mM) where N = 1. Mean % inhibition of superoxide anion signal increased in a dose-dependent manner as the concentration of lutein diphosphate was increased in the test assay. At 100 μM in water, no inhibition of scavenging was seen. The molecular solution in 40% EtOH (mean % inhibition = 18%) was increased above background

| Sample | Solvent | Concentration | N | Mean (% inhibition) | S.D. | SEM | Min | Max | Range |
|---|---|---|---|---|---|---|---|---|---|
| Lutein Diphosphate Sodium Salt | 40% EtOH | 0.1 mM | 3 | 18.0 | 7.0 | 4.0 | 11 | 25 | 14 |
| Lutein Diphosphate Sodium Salt | Water | 0.1 mM | 1 | 0.0 | ND | ND | 0 | 0 | 0 |

TABLE 2-continued

Descriptive statistics of mean % inhibition of superoxide anion signal for aqueous and ethanolic (40%) formulations of disodium diphosphate derivatives of natural source lutein tested in the current study. Sample sizes of 3 were evaluated for each formulation, with the exception of lutein diphosphate in water at 100 µM (0.1 mM) where N = 1. Mean % inhibition of superoxide anion signal increased in a dose-dependent manner as the concentration of lutein diphosphate was increased in the test assay. At 100 µM in water, no inhibition of scavenging was seen. The molecular solution in 40% EtOH (mean % inhibition = 18%) was increased above background

| Sample | Solvent | Concentration | N | Mean (% inhibition) | S.D. | SEM | Min | Max | Range |
|---|---|---|---|---|---|---|---|---|---|
| Lutein Diphosphate Sodium Salt | Water | 1.0 mM | 3 | 9.3 | 3.5 | 2.0 | 6 | 13 | 7 |
| Lutein Diphosphate Sodium Salt | Water | 3.0 mM | 3 | 72.3 | 3.1 | 1.8 | 69 | 75 | 6 |
| Lutein Diphosphate Sodium Salt | Water | 5.0 mM | 3 | 91.0 | 2.6 | 1.5 | 88 | 93 | 5 | scavenging (5%) by the ethanolic vehicle, suggesting that disaggregation increased scavenging at that concentration. Slightly increased scavenging (on a molar basis) may have been obtained with the diphosphate derivative in comparison to disuccinate derivative (see Table 1 and FIG. 8).

In the current study, facile preparations of the disodium disuccinate and tetrasodium phosphate esters of natural source (RRR) lutein are described. These asymmetric C40 carotenoid derivatives exhibited aqueous dispersibility of 2.85 and 29.27 mg/mL, respectively. Evidence for both card-pack (H-type) and head-to-tail (J-type) supramolecular assembly was obtained with UV-Vis spectroscopy for the aqueous solutions of these compounds. Electronic paramagnetic spectroscopy of direct aqueous superoxide scavenging by these derivatives demonstrated nearly identical dose-dependent scavenging profiles, with slightly increased scavenging noted for the diphosphate derivative. In each case, scavenging in the millimolar range was observed. These results show that as parenteral soft drugs with aqueous radical scavenging activity, both compounds are useful in those clinical applications in which rapid and/or intravenous delivery is desired for the desired therapeutic effect(s).

EXPERIMENTAL EXAMPLES

Experimental Methods

Thioglycollate/Zymosan—Induced Peritonitis Model: Wild-type mice were administered either 500 mg/kg body weight of disodium disuccinate astaxanthin (ddAst/Cardax™) in an oil emulsion vehicle, or normal saline (NS) as a negative control, by oral gavage at 24 hours intervals beginning 7 days prior to the induction of peritonitis. Peritonitis was induced experimentally as follows: mice were injected intraperitoneally with 1 ml of 4% by weight thioglycollate (Tg) broth, to induce the recruitment of proinflammatory cells to the peritoneum. Either 16 hours or 72 hours after recruitment, approximately half of the mice were injected intraperitoneally with 250 mg/kg body weight of zymosan (Z) for a further 4 hours. The mice not receiving zymosan underwent no further treatment. Peritoneal lavage was performed in control animals or animals treated with (ddAst) 16 hours post Tg injection, or 20 h following the combination of both Tg injection (16 hours) followed by Z injection (4 hours), as indicated (Tg/Z). Peritoneal lavages were performed with phosphate-buffered saline containing antioxidant (0.1 mM butylated hydroxytoluene (BHT)) and 2 mM of the metal chelator diethylenetriamine pentaacetic acid (DTPA) according to established practices in the art. The lavage suspensions were transferred to screw-capped tubes under an argon atmosphere, and immediately centrifuged at 1000 rpm in a table top microcentrifuge for 10 min at 4° C. to remove whole cells and debris. All analyses of lipid peroxidation products was performed on cell-free lavage supernatants. Cell pellets were resuspended in phosphate-buffered saline containing 0.1 mM BHT and 0.1 mM DTPA, and differential cell counts (macrophages, monocytes, eosinophils, lymphocytes, neutrophils, and erythrocytes) were performed on cytospun preparations of isolated cells according to established procedures in the art.

Experimental Example 1

Electrospray ionization tandem mass spectrometry was used to simultaneously quantify individual molecular species of HETEs, HPETEs, the prostaglandin $PGF_{2\alpha}$, $F_2$-isoprostanoids, hydroxy- and hydroperoxy-octadecadienoic acids (H(P)ODEs), and their precursors, arachidonic acid (AA) and linoleic acid (LA). Additionally, the molar ratios of o-tyrosine (oY/F). were measured.

Experimental Example 2

The following is a general summary of some of the results found in these studies:

1. The levels of LA and AA (pmol) are significantly higher in animals treated with ddAst when compared to animals treated with NS at 16 hours Tg, and at 72 hours Tg/4 hour Z.
2. The following showed a significant decrease with the use of ddAst (compared to NS):
    a. PGF2α/AA ratio at 72 hours Tg/4 hour Z.
    b. 11-HETE/AA ratio at 72 hours Tg/4 hour Z.
    c. 5-HETE/AA ratio at 72 hours Tg/4 hour Z.
    d. 9-HETE/AA ratio at 72 hours Tg/4 hour Z 8-iso-F2α (pmol) at 16 hours Tg/4 hour Z.
    e. 8-iso-F2α/AA ratio at 16 hours Tg/4 hour Z.
    f. 9-HODE/LA (ratio) at 72 hours Tg/4 hour Z.
    g. 5-oxo-EET (pmol) at 72 Tg/4 hour Z. 5-oxo-EET (ratio) at 72 hours Tg/4 hour Z.
    h. oY/F at 16 hours Tg/4 hour Z.

Experimental Example 3

The following tables contain the statistical analyses of in vivo lipid oxidation molecular fingerprint data obtained with the experimentally induced peritonitis model in mice treated with ddAst (Cardax™).

TABLE 3

Arachidonic Acid (pmol)

| PARAMETER | STATISTIC | Drug | | P-VALUE |
|---|---|---|---|---|
| | | NS | Cardax | |
| Baseline | N | 6 | 6 | 1.000 NP |
| | MEAN | 524.36 | 587.46 | |
| | S.D. | 427.783 | 516.759 | |
| | MEDIAN | 308.68 | 323.65 | |
| | (MIN, MAX) | (254.93, 1352.3) | (220.14, 1499.4) | |
| 16 Hour Thio-glycollate | N | 8 | 8 | 0.018 |
| | MEAN | 763.37 | 1791.6 | |
| | S.D. | 274.650 | 1055.11 | |
| | MEDIAN | 706.31 | 1854.3 | |
| | (MIN, MAX) | (473.74, 1311.4) | (523.76, 3620.7) | |

TABLE 3-continued

Arachidonic Acid (pmol)

| PARAMETER | STATISTIC | Drug | | P-VALUE |
|---|---|---|---|---|
| | | NS | Cardax | |
| 16 Hour Thio-glycollate/4 Hour Zymosan | N | 8 | 7 | 0.685 NP |
| | MEAN | 1258.1 | 1208.5 | |
| | S.D. | 551.126 | 513.245 | |
| | MEDIAN | 1546.4 | 1039.6 | |
| | (MIN, MAX) | (249.21, 1716.4) | (697.61, 2127.0) | |
| 72 Hour Thio-glycollate | N | 8 | 7 | 0.524 NP |
| | MEAN | 735.88 | 836.27 | |
| | S.D. | 536.150 | 441.348 | |
| | MEDIAN | 549.73 | 758.43 | |
| | (MIN, MAX) | (307.34, 1911.9) | (443.53, 1736.7) | |
| 72 Hour Thio-glycollate/4 Hour Zymosan | N | 8 | 7 | 0.001 NP |
| | MEAN | 1455.3 | 3554.3 | |
| | S.D. | 383.848 | 2374.36 | |
| | MEDIAN | 1516.5 | 2429.5 | |
| | (MIN, MAX) | (928.93, 1989.1) | (2074.4, 8470.4) | |

P-VALUEs: NP = non-parametric test

TABLE 4

Linoleic Acid (pmol)

| PARAMETER | STATISTIC | Drug | | P-VALUE |
|---|---|---|---|---|
| | | NS | Cardax | |
| Baseline | N | 6 | 6 | 0.843 |
| | MEAN | 8939.0 | 8239.5 | |
| | S.D. | 5859.01 | 6057.96 | |
| | MEDIAN | 6173.2 | 5875.6 | |
| | (MIN, MAX) | (3950.5, 17675) | (2959.8, 18270) | |
| 16 Hour Thioglycollate | N | 8 | 8 | 0.040 |
| | MEAN | 9901.8 | 22739 | |
| | S.D. | 4802.56 | 15321.7 | |
| | MEDIAN | 8556.6 | 22907 | |
| | (MIN, MAX) | (3937.9, 18635) | (5009.1, 46443) | |
| 16 Hour Thioglycollate/4 Hour Zymosan | N | 8 | 7 | 0.557 |
| | MEAN | 14623 | 13158 | |
| | S.D. | 2779.23 | 6225.18 | |
| | MEDIAN | 15308 | 10509 | |
| | (MIN, MAX) | (10101, 17181) | (7657.9, 23387) | |
| 72 Hour Thioglycollate | N | 8 | 7 | 0.603 NP |
| | MEAN | 12800 | 14242 | |
| | S.D. | 8398.75 | 10380.2 | |
| | MEDIAN | 9913.9 | 10076 | |
| | (MIN, MAX) | (6019.9, 29981) | (7626.2, 36785) | |
| 72 Hour Thioglycollate/4 Hour Zymosan | N | 8 | 7 | 0.018 NP |
| | MEAN | 18618 | 33183 | |
| | S.D. | 4688.68 | 21432.9 | |
| | MEDIAN | 17481 | 27585 | |
| | (MIN, MAX) | (13754, 27612) | (19790, 80717) | |

P-VALUEs: NP = non-parametric test

TABLE 5

Prostaglandin F2α (PGF$_{2α}$) (pmol)

| | | Drug | | |
|---|---|---|---|---|
| PARAMETER | STATISTIC | NS | Cardax | P-VALUE |
| Baseline | N | 6 | 6 | 0.158 NP |
| | MEAN | 0.095 | 0.036 | |
| | S.D. | 0.1432 | 0.0808 | |
| | MEDIAN | 0.049 | 0.000 | |
| | (MIN, MAX) | (0.000, 0.381) | (0.000, 0.200) | |
| 16 Hour Thio-glycollate | N | 8 | 8 | 0.172 |
| | MEAN | 0.020 | 0.037 | |
| | S.D. | 0.0167 | 0.0292 | |
| | MEDIAN | 0.019 | 0.033 | |
| | (MIN, MAX) | (0.000, 0.049) | (0.000, 0.089) | |
| 16 Hour Thio-glycollate/4 Hour Zymosan | N | 8 | 7 | 0.250 |
| | MEAN | 0.058 | 0.038 | |
| | S.D. | 0.0414 | 0.0135 | |
| | MEDIAN | 0.047 | 0.035 | |
| | (MIN, MAX) | (0.000, 0.119) | (0.025, 0.061) | |
| 72 Hour Thio-glycollate | N | 8 | 7 | 0.726 |
| | MEAN | 0.025 | 0.021 | |
| | S.D. | 0.0190 | 0.0213 | |
| | MEDIAN | 0.019 | 0.018 | |
| | (MIN, MAX) | (0.000, 0.064) | (0.000, 0.063) | |
| 72 Hour Thio-glycollate/4 Hour Zymosan | N | 8 | 7 | 0.629 |
| | MEAN | 0.047 | 0.040 | |
| | S.D. | 0.0233 | 0.0327 | |
| | MEDIAN | 0.039 | 0.039 | |
| | (MIN, MAX) | (0.023, 0.089) | (0.000, 0.082) | |

P-VALUEs: NP = non-parametric test

TABLE 6

PGF2a/AA (ratio)

| | | Drug | | |
|---|---|---|---|---|
| PARAMETER | STATISTIC | NS | Cardax | P-VALUE |
| Baseline | N | 6 | 6 | 0.081 NP |
| | MEAN | 0.159 | 0.033 | |
| | S.D. | 0.1231 | 0.0559 | |
| | MEDIAN | 0.184 | 0.000 | |
| | (MIN, MAX) | (0.000, 0.282) | (0.000, 0.134) | |
| 16 Hour Thio-glycollate | N | 8 | 8 | 0.986 |
| | MEAN | 0.034 | 0.034 | |
| | S.D. | 0.0335 | 0.0359 | |
| | MEDIAN | 0.025 | 0.018 | |
| | (MIN, MAX) | (0.000, 0.100) | (0.000, 0.102) | |
| 16 Hour Thio-glycollate/4 Hour Zymosan | N | 8 | 7 | 0.685 NP |
| | MEAN | 0.067 | 0.038 | |
| | S.D. | 0.0704 | 0.0257 | |
| | MEDIAN | 0.042 | 0.025 | |
| | (MIN, MAX) | (0.000, 0.200) | (0.015, 0.087) | |
| 72 Hour Thio-glycollate | N | 8 | 7 | 0.542 |
| | MEAN | 0.040 | 0.030 | |
| | S.D. | 0.0324 | 0.0257 | |
| | MEDIAN | 0.032 | 0.033 | |
| | (MIN, MAX) | (0.000, 0.103) | (0.000, 0.064) | |
| 72 Hour Thio-glycollate/4 Hour Zymosan | N | 8 | 7 | 0.010 |
| | MEAN | 0.035 | 0.011 | |
| | S.D. | 0.0197 | 0.0085 | |
| | MEDIAN | 0.037 | 0.012 | |
| | (MIN, MAX) | (0.013, 0.070) | (0.000, 0.022) | |

P-VALUEs: NP = non-parametric test

TABLE 7

11-HETE (pmol)

| | | Drug | | |
|---|---|---|---|---|
| PARAMETER | STATISTIC | NS | Cardax | P-VALUE |
| Baseline | N | 6 | 6 | 0.471 NP |
| | MEAN | 0.091 | 0.121 | |
| | S.D. | 0.0873 | 0.0934 | |
| | MEDIAN | 0.056 | 0.073 | |
| | (MIN, MAX) | (0.034, 0.265) | (0.048, 0.240) | |
| 16 Hour Thio-glycollate | N | 8 | 8 | 0.372 NP |
| | MEAN | 0.711 | 0.434 | |
| | S.D. | 1.4514 | 0.3930 | |
| | MEDIAN | 0.132 | 0.329 | |
| | (MIN, MAX) | (0.054, 4.275) | (0.100, 1.274) | |
| 16 Hour Thio-glycollate/4 Hour Zymosan | N | 8 | 7 | 0.862 NP |
| | MEAN | 0.614 | 0.654 | |
| | S.D. | 0.4010 | 0.4004 | |
| | MEDIAN | 0.450 | 0.450 | |
| | (MIN, MAX) | (0.203, 1.285) | (0.385, 1.438) | |
| 72 Hour Thio-glycollate | N | 8 | 7 | 0.741 |
| | MEAN | 0.101 | 0.112 | |
| | S.D. | 0.0552 | 0.0688 | |
| | MEDIAN | 0.095 | 0.100 | |
| | (MIN, MAX) | (0.031, 0.193) | (0.034, 0.232) | |
| 72 Hour Thio-glycollate/4 Hour Zymosan | N | 8 | 7 | 0.862 NP |
| | MEAN | 0.651 | 0.837 | |
| | S.D. | 0.2373 | 0.5531 | |
| | MEDIAN | 0.654 | 0.703 | |
| | (MIN, MAX) | (0.200, 0.974) | (0.367, 2.004) | |

P-VALUEs: NP = non-parametric test

TABLE 8

11-HETE/AA (ratio)

| | | Drug | | |
|---|---|---|---|---|
| PARAMETER | STATISTIC | NS | Cardax | P-VALUE |
| Baseline | N | 6 | 6 | 0.290 |
| | MEAN | 0.176 | 0.219 | |
| | S.D. | 0.0743 | 0.0584 | |
| | MEDIAN | 0.169 | 0.218 | |
| | (MIN, MAX) | (0.078, 0.289) | (0.154, 0.302) | |
| 16 Hour Thio-glycollate | N | 8 | 8 | 0.793 NP |
| | MEAN | 0.815 | 0.239 | |
| | S.D. | 1.5380 | 0.1319 | |
| | MEDIAN | 0.275 | 0.195 | |
| | (MIN, MAX) | (0.069, 4.577) | (0.081, 0.499) | |
| 16 Hour Thio-glycollate/4 Hour Zymosan | N | 8 | 7 | 0.954 NP |
| | MEAN | 0.588 | 0.669 | |
| | S.D. | 0.4410 | 0.6333 | |
| | MEDIAN | 0.459 | 0.453 | |
| | (MIN, MAX) | (0.235, 1.545) | (0.198, 2.061) | |
| 72 Hour Thio-glycollate | N | 8 | 7 | 0.512 |
| | MEAN | 0.193 | 0.151 | |
| | S.D. | 0.1401 | 0.0912 | |
| | MEDIAN | 0.179 | 0.132 | |
| | (MIN, MAX) | (0.027, 0.432) | (0.037, 0.277) | |
| 72 Hour Thio-glycollate/4 Hour Zymosan | N | 8 | 7 | 0.008 |
| | MEAN | 0.446 | 0.253 | |
| | S.D. | 0.1341 | 0.1022 | |
| | MEDIAN | 0.473 | 0.237 | |
| | (MIN, MAX) | (0.209, 0.617) | (0.122, 0.386) | |

P-VALUEs: NP = non-parametric test

TABLE 9

13-HODE (pmol)

| PARAMETER | STATISTIC | Drug NS | Cardax | P-VALUE |
|---|---|---|---|---|
| Baseline | N | 6 | 6 | 0.271 |
| | MEAN | 15.703 | 26.618 | |
| | S.D. | 5.8689 | 22.1597 | |
| | MEDIAN | 14.507 | 23.554 | |
| | (MIN, MAX) | (9.949, 25.391) | (4.819, 59.825) | |
| 16 Hour Thio-glycollate | N | 8 | 8 | 0.982 |
| | MEAN | 18.692 | 18.838 | |
| | S.D. | 12.6914 | 13.1484 | |
| | MEDIAN | 20.007 | 15.191 | |
| | (MIN, MAX) | (1.458, 35.610) | (3.592, 43.157) | |
| 16 Hour Thio-glycollate/4 Hour Zymosan | N | 8 | 7 | 0.165 |
| | MEAN | 11.896 | 5.689 | |
| | S.D. | 10.4317 | 4.1488 | |
| | MEDIAN | 6.823 | 4.768 | |
| | (MIN, MAX) | (2.745, 28.542) | (2.392, 13.819) | |
| 72 Hour Thio-glycollate | N | 8 | 7 | 0.393 |
| | MEAN | 4.319 | 5.552 | |
| | S.D. | 2.1160 | 3.2430 | |
| | MEDIAN | 4.438 | 5.520 | |
| | (MIN, MAX) | (1.520, 7.499) | (2.182, 10.441) | |
| 72 Hour Thio-glycollate/4 Hour Zymosan | N | 8 | 7 | 0.271 |
| | MEAN | 5.543 | 7.181 | |
| | S.D. | 1.6033 | 3.6626 | |
| | MEDIAN | 5.806 | 6.732 | |
| | (MIN, MAX) | (3.050, 8.104) | (3.032, 13.828) | |

TABLE 10

13-HODE/AA (ratio)

| PARAMETER | STATISTIC | Drug NS | Cardax | P-VALUE |
|---|---|---|---|---|
| Baseline | N | 6 | 6 | 0.391 |
| | MEAN | 2.300 | 2.976 | |
| | S.D. | 1.2346 | 1.3748 | |
| | MEDIAN | 2.392 | 2.848 | |
| | (MIN, MAX) | (0.766, 3.803) | (1.628, 5.453) | |
| 16 Hour Thio-glycollate | N | 8 | 8 | 0.096 |
| | MEAN | 2.660 | 0.905 | |
| | S.D. | 2.7623 | 0.3258 | |
| | MEDIAN | 2.141 | 0.920 | |
| | (MIN, MAX) | (0.140, 8.357) | (0.379, 1.389) | |
| 16 Hour Thio-glycollate/4 Hour Zymosan | N | 8 | 7 | 0.772 NP |
| | MEAN | 0.939 | 0.456 | |
| | S.D. | 0.9061 | 0.2492 | |
| | MEDIAN | 0.457 | 0.376 | |
| | (MIN, MAX) | (0.167, 2.284) | (0.119, 0.805) | |
| 72 Hour Thio-glycollate | N | 8 | 7 | 0.968 |
| | MEAN | 0.496 | 0.504 | |
| | S.D. | 0.3196 | 0.3926 | |
| | MEDIAN | 0.578 | 0.363 | |
| | (MIN, MAX) | (0.052, 0.945) | (0.158, 1.250) | |
| 72 Hour Thio-glycollate/4 Hour Zymosan | N | 8 | 7 | 0.118 NP |
| | MEAN | 0.297 | 0.229 | |
| | S.D. | 0.0498 | 0.0775 | |
| | MEDIAN | 0.296 | 0.186 | |
| | (MIN, MAX) | (0.218, 0.383) | (0.153, 0.325) | |

P-VALUEs: NP = non-parametric test

TABLE 11

5-HETE (pmol)

| PARAMETER | STATISTIC | Drug NS | Cardax | P-VALUE |
|---|---|---|---|---|
| Baseline | N | 6 | 6 | 0.471 NP |
| | MEAN | 0.058 | 0.096 | |
| | S.D. | 0.0884 | 0.1143 | |
| | MEDIAN | 0.027 | 0.047 | |
| | (MIN, MAX) | (0.000, 0.237) | (0.012, 0.306) | |
| 16 Hour Thio-glycollate | N | 8 | 8 | 0.318 NP |
| | MEAN | 0.548 | 0.334 | |
| | S.D. | 1.1317 | 0.2613 | |
| | MEDIAN | 0.085 | 0.255 | |
| | (MIN, MAX) | (0.028, 3.326) | (0.069, 0.942) | |
| 16 Hour Thio-glycollate/4 Hour Zymosan | N | 8 | 7 | 0.900 |
| | MEAN | 1.128 | 1.082 | |
| | S.D. | 0.8203 | 0.5021 | |
| | MEDIAN | 1.000 | 0.953 | |
| | (MIN, MAX) | (0.187, 2.439) | (0.529, 1.637) | |
| 72 Hour Thio-glycollate | N | 8 | 7 | 0.325 NP |
| | MEAN | 0.080 | 0.129 | |
| | S.D. | 0.0498 | 0.1029 | |
| | MEDIAN | 0.065 | 0.082 | |
| | (MIN, MAX) | (0.033, 0.180) | (0.035, 0.322) | |
| 72 Hour Thio-glycollate/4 Hour Zymosan | N | 8 | 7 | 0.385 NP |
| | MEAN | 1.269 | 1.236 | |
| | S.D. | 0.4050 | 0.7544 | |
| | MEDIAN | 1.353 | 0.997 | |
| | (MIN, MAX) | (0.435, 1.877) | (0.598, 2.820) | |

P-VALUEs: NP = non-parametric test

TABLE 12

5-HETE/AA (ratio)

| PARAMETER | STATISTIC | Drug NS | Cardax | P-VALUE |
|---|---|---|---|---|
| Baseline | N | 6 | 6 | 0.302 |
| | MEAN | 0.092 | 0.129 | |
| | S.D. | 0.0571 | 0.0603 | |
| | MEDIAN | 0.095 | 0.145 | |
| | (MIN, MAX) | (0.000, 0.175) | (0.049, 0.204) | |
| 16 Hour Thio-glycollate | N | 8 | 8 | 0.875 NP |
| | MEAN | 0.617 | 0.218 | |
| | S.D. | 1.2027 | 0.1479 | |
| | MEDIAN | 0.129 | 0.151 | |
| | (MIN, MAX) | (0.040, 3.561) | (0.070, 0.485) | |
| 16 Hour Thio-glycollate/4 Hour Zymosan | N | 8 | 7 | 1.000 NP |
| | MEAN | 1.231 | 0.997 | |
| | S.D. | 1.4615 | 0.6014 | |
| | MEDIAN | 0.647 | 0.770 | |
| | (MIN, MAX) | (0.216, 4.688) | (0.499, 2.165) | |
| 72 Hour Thio-glycollate | N | 8 | 7 | 0.793 |
| | MEAN | 0.153 | 0.170 | |
| | S.D. | 0.1226 | 0.1339 | |
| | MEDIAN | 0.119 | 0.082 | |
| | (MIN, MAX) | (0.035, 0.368) | (0.047, 0.383) | |
| 72 Hour Thio-glycollate/4 Hour Zymosan | N | 8 | 7 | 0.002 NP |
| | MEAN | 0.875 | 0.369 | |
| | S.D. | 0.2294 | 0.1329 | |
| | MEDIAN | 0.916 | 0.333 | |
| | (MIN, MAX) | (0.455, 1.202) | (0.270, 0.644) | |

P-VALUEs: NP = non-parametric test

TABLE 13

9-HETE (pmol)

| PARAMETER | STATISTIC | Drug NS | Drug Cardax | P-VALUE |
|---|---|---|---|---|
| Baseline | N | 6 | 6 | 0.810 NP |
|  | MEAN | 0.290 | 0.510 |  |
|  | S.D. | 0.1279 | 0.4753 |  |
|  | MEDIAN | 0.248 | 0.272 |  |
|  | (MIN, | (0.161, | (0.163, |  |
|  | MAX) | 0.526) | 1.332) |  |
| 16 Hour Thiog-lycollate | N | 8 | 8 | 0.958 NP |
|  | MEAN | 1.375 | 0.826 |  |
|  | S.D. | 2.0521 | 0.6223 |  |
|  | MEDIAN | 0.661 | 0.718 |  |
|  | (MIN, | (0.142, | (0.138, |  |
|  | MAX) | 6.271) | 2.129) |  |
| 16 Hour Thio-glycollate/4 Hour Zymosan | N | 8 | 7 | 0.354 |
|  | MEAN | 0.735 | 0.559 |  |
|  | S.D. | 0.4453 | 0.1982 |  |
|  | MEDIAN | 0.586 | 0.612 |  |
|  | (MIN, | (0.310, | (0.271, |  |
|  | MAX) | 1.466) | 0.825) |  |
| 72 Hour Thio-glycollate | N | 8 | 7 | 0.117 |
|  | MEAN | 0.164 | 0.274 |  |
|  | S.D. | 0.1051 | 0.1467 |  |
|  | MEDIAN | 0.158 | 0.299 |  |
|  | (MIN, | (0.000, | (0.079, |  |
|  | MAX) | 0.334) | 0.440) |  |
| 72 Hour Thio-glycollate/4 Hour Zymosan | N | 8 | 7 | 0.118 NP |
|  | MEAN | 0.505 | 0.917 |  |
|  | S.D. | 0.1360 | 0.7809 |  |
|  | MEDIAN | 0.506 | 0.687 |  |
|  | (MIN, | (0.248, | (0.421, |  |
|  | MAX) | 0.724) | 2.657) |  |

P-VALUEs: NP = non-parametric test

TABLE 14

9-HETE/AA (ratio)

| PARAMETER | STATISTIC | Drug NS | Drug Cardax | P-VALUE |
|---|---|---|---|---|
| Baseline | N | 6 | 6 | 0.418 |
|  | MEAN | 0.711 | 0.879 |  |
|  | S.D. | 0.3306 | 0.3554 |  |
|  | MEDIAN | 0.774 | 0.887 |  |
|  | (MIN, | (0.257, | (0.484, |  |
|  | MAX) | 1.095) | 1.506) |  |
| 16 Hour Thio-glycollate | N | 8 | 8 | 0.227 NP |
|  | MEAN | 1.716 | 0.476 |  |
|  | S.D. | 2.1878 | 0.2471 |  |
|  | MEDIAN | 0.990 | 0.448 |  |
|  | (MIN, | (0.199, | (0.179, |  |
|  | MAX) | 6.715) | 0.843) |  |
| 16 Hour Thio-glycollate/4 Hour Zymosan | N | 8 | 7 | 0.272 NP |
|  | MEAN | 0.665 | 0.529 |  |
|  | S.D. | 0.3375 | 0.3129 |  |
|  | MEDIAN | 0.708 | 0.472 |  |
|  | (MIN, | (0.200, | (0.229, |  |
|  | MAX) | 1.250) | 1.183) |  |
| 72 Hour Thio-glycollate | N | 8 | 7 | 0.862 NP |
|  | MEAN | 0.336 | 0.348 |  |
|  | S.D. | 0.2698 | 0.1912 |  |
|  | MEDIAN | 0.327 | 0.241 |  |
|  | (MIN, | (0.000, | (0.162, |  |
|  | MAX) | 0.719) | 0.581) |  |
| 72 Hour Thio-glycollate/4 Hour Zymosan | N | 8 | 7 | 0.056 NP |
|  | MEAN | 0.354 | 0.253 |  |
|  | S.D. | 0.0909 | 0.0711 |  |
|  | MEDIAN | 0.335 | 0.244 |  |
|  | (MIN, | (0.259, | (0.162, |  |
|  | MAX) | 0.562) | 0.331) |  |

P-VALUEs: NP = non-parametric test

TABLE 15

9-HODE (pmol)

| PARAMETER | STATISTIC | Drug NS | Drug Cardax | P-VALUE |
|---|---|---|---|---|
| Baseline | N | 6 | 6 | 0.920 |
|  | MEAN | 1.869 | 1.791 |  |
|  | S.D. | 1.1514 | 1.4605 |  |
|  | MEDIAN | 1.645 | 1.579 |  |
|  | (MIN, | (0.812, | (0.325, |  |
|  | MAX) | 4.056) | 3.698) |  |
| 16 Hour Thio-glycollate | N | 8 | 8 | 0.120 |
|  | MEAN | 2.783 | 5.367 |  |
|  | S.D. | 2.2096 | 3.8201 |  |
|  | MEDIAN | 2.200 | 3.831 |  |
|  | (MIN, | (0.364, | (1.255, |  |
|  | MAX) | 6.519) | 11.829) |  |
| 16 Hour Thio-glycollate/4 Hour Zymosan | N | 8 | 7 | 0.299 |
|  | MEAN | 3.350 | 2.767 |  |
|  | S.D. | 1.0722 | 1.0055 |  |
|  | MEDIAN | 3.319 | 2.825 |  |
|  | (MIN, | (2.010, | (1.622, |  |
|  | MAX) | 4.858) | 4.151) |  |
| 72 Hour Thio-glycollate | N | 8 | 7 | 0.349 |
|  | MEAN | 2.481 | 1.831 |  |
|  | S.D. | 1.4168 | 1.1302 |  |
|  | MEDIAN | 2.241 | 1.585 |  |
|  | (MIN, | (0.602, | (0.680, |  |
|  | MAX) | .264) | 4.094) |  |
| 72 Hour Thio-glycollate/4 Hour Zymosan | N | 8 | 7 | 0.772 NP |
|  | MEAN | 3.750 | 4.747 |  |
|  | S.D. | 1.2838 | 4.4064 |  |
|  | MEDIAN | 3.936 | 3.683 |  |
|  | (MIN, | (2.142, | (1.662, |  |
|  | MAX) | 5.911) | 14.412) |  |

P-VALUES: NP = non-parametric test

TABLE 16

9-HODE/LA (ratio)

| PARAMETER | STATISTIC | Drug NS | Drug Cardax | P-VALUE |
|---|---|---|---|---|
| Baseline | N | 6 | 6 | 0.298 NP |
|  | MEAN | 0.229 | 0.212 |  |
|  | S.D. | 0.0785 | 0.1469 |  |
|  | MEDIAN | 0.229 | 0.168 |  |
|  | (MIN, | (0.112, | (0.110, |  |
|  | MAX) | 0.342) | 0.505) |  |
| 16 Hour Thio-glycollate | N | 8 | 8 | 0.564 NP |
|  | MEAN | 0.419 | 0.292 |  |
|  | S.D. | 0.5406 | 0.1670 |  |
|  | MEDIAN | 0.240 | 0.255 |  |
|  | (MIN, | (0.035, | (0.070, |  |
|  | MAX) | 1.655) | 0.610) |  |
| 16 Hour Thio-glycollate/4 Hour Zymosan | N | 8 | 7 | 0.862 NP |
|  | MEAN | 0.251 | 0.245 |  |
|  | S.D. | 0.1367 | 0.1418 |  |
|  | MEDIAN | 0.207 | 0.201 |  |
|  | (MIN, | (0.129, | (0.089, |  |
|  | MAX) | 0.480) | 0.542) |  |
| 72 Hour Thio-glycollate | N | 8 | 7 | 0.275 |
|  | MEAN | 0.285 | 0.180 |  |
|  | S.D. | 0.1879 | 0.1632 |  |
|  | MEDIAN | 0.315 | 0.109 |  |
|  | (MIN, | (0.020, | (0.043, |  |
|  | MAX) | 0.563) | 0.490) |  |
| 72 Hour Thio-glycollate/4 Hour Zymosan | N | 8 | 7 | 0.006 |
|  | MEAN | 0.198 | 0.132 |  |
|  | S.D. | 0.0319 | 0.0466 |  |
|  | MEDIAN | 0.204 | 0.134 |  |
|  | (MIN, | (0.153, | (0.084, |  |
|  | MAX) | 0.247) | 0.190) |  |

P-VALUEs: NP = non-parametric test

TABLE 17

8-iso-F2a (pmol)

| PARAMETER | STATISTIC | Drug NS | Cardax | P-VALUE |
|---|---|---|---|---|
| Baseline | N | 6 | 6 | 0.354 |
| | MEAN | 0.087 | 0.156 | |
| | S.D. | 0.1091 | 0.1335 | |
| | MEDIAN | 0.060 | 0.175 | |
| | (MIN, MAX) | (0.000, 0.293) | (0.000, 0.360) | |
| 16 Hour Thio-glycollate | N | 8 | 8 | 0.874 NP |
| | MEAN | 0.075 | 0.052 | |
| | S.D. | 0.0603 | 0.0458 | |
| | MEDIAN | 0.052 | 0.069 | |
| | (MIN, MAX) | (0.031, 0.213) | (0.000, 0.115) | |
| 16 Hour Thio-glycollate/4 Hour Zymosan | N | 8 | 7 | 0.036 NP |
| | MEAN | 0.067 | 0.012 | |
| | S.D. | 0.0502 | 0.0166 | |
| | MEDIAN | 0.073 | 0.000 | |
| | (MIN, MAX) | (0.000, 0.152) | (0.000, 0.040) | |
| 72 Hour Thio-glycollate | N | 8 | 7 | 0.334 NP |
| | MEAN | 0.005 | 0.010 | |
| | S.D. | 0.0142 | 0.0145 | |
| | MEDIAN | 0.000 | 0.000 | |
| | (MIN, MAX) | (0.000, 0.040) | (0.000, 0.037) | |
| 72 Hour Thio-glycollate/4 Hour Zymosan | N | 8 | 7 | 0.502 NP |
| | MEAN | 0.072 | 0.057 | |
| | S.D. | 0.1408 | 0.0621 | |
| | MEDIAN | 0.000 | 0.037 | |
| | (MIN, MAX) | (0.000, 0.406) | (0.000, 0.147) | |

P-VALUEs: NP = non-parametric test

TABLE 18

8-iso-F2a/AA (ratio)

| PARAMETER | STATISTIC | Drug NS | Cardax | P-VALUE |
|---|---|---|---|---|
| Baseline | N | 6 | 6 | 0.292 |
| | MEAN | 0.163 | 0.307 | |
| | S.D. | 0.1423 | 0.2840 | |
| | MEDIAN | 0.196 | 0.266 | |
| | (MIN, MAX) | (0.000, 0.369) | (0.000, 0.718) | |
| 16 Hour Thio-glycollate | N | 8 | 8 | 0.065 NP |
| | MEAN | 0.117 | 0.044 | |
| | S.D. | 0.1311 | 0.0495 | |
| | MEDIAN | 0.068 | 0.034 | |
| | (MIN, MAX) | (0.035, 0.433) | (0.000, 0.135) | |
| 16 Hour Thio-glycollate/4 Hour Zymosan | N | 8 | 7 | 0.049 NP |
| | MEAN | 0.053 | 0.011 | |
| | S.D. | 0.0437 | 0.0167 | |
| | MEDIAN | 0.049 | 0.000 | |
| | (MIN, MAX) | (0.000, 0.126) | (0.000, 0.038) | |
| 72 Hour Thio-glycollate | N | 8 | 7 | 0.334 NP |
| | MEAN | 0.013 | 0.016 | |
| | S.D. | 0.0375 | 0.0212 | |
| | MEDIAN | 0.000 | 0.000 | |
| | (MIN, MAX) | (0.000, 0.106) | (0.000, 0.049) | |
| 72 Hour Thio-glycollate/4 Hour Zymosan | N | 8 | 7 | 0.760 NP |
| | MEAN | 0.070 | 0.017 | |
| | S.D. | 0.1465 | 0.0234 | |
| | MEDIAN | 0.000 | 0.011 | |
| | (MIN, MAX) | (0.000, 0.425) | (0.000, 0.068) | |

P-VALUEs: NP = non-parametric test

TABLE 19

5-oxo-ETE (pmol)

| PARAMETER | STATISTIC | Drug NS | Cardax | P-VALUE |
|---|---|---|---|---|
| Baseline | N | 6 | 6 | 0.789 NP |
| | MEAN | 0.115 | 0.020 | |
| | S.D. | 0.2568 | 0.0349 | |
| | MEDIAN | 0.009 | 0.000 | |
| | (MIN, MAX) | (0.000, 0.638) | (0.000, 0.086) | |
| 16 Hour Thio-glycollate | N | 8 | 8 | 0.113 |
| | MEAN | 0.045 | 0.128 | |
| | S.D. | 0.0398 | 0.1322 | |
| | MEDIAN | 0.030 | 0.078 | |
| | (MIN, MAX) | (0.000, 0.118) | (0.000, 0.363) | |
| 16 Hour Thio-glycollate/4 Hour Zymosan | N | 8 | 7 | 0.815 |
| | MEAN | 0.091 | 0.085 | |
| | S.D. | 0.0581 | 0.0262 | |
| | MEDIAN | 0.088 | 0.083 | |
| | (MIN, MAX) | (0.000, 0.174) | (0.045, 0.121) | |
| 72 Hour Thio-glycollate | N | 8 | 7 | 0.824 NP |
| | MEAN | 0.018 | 0.026 | |
| | S.D. | 0.0409 | 0.0506 | |
| | MEDIAN | 0.000 | 0.000 | |
| | (MIN, MAX) | (0.000, 0.116) | (0.000, 0.132) | |
| 72 Hour Thio-glycollate/4 Hour Zymosan | N | 8 | 7 | 0.073 NP |
| | MEAN | 0.495 | 0.148 | |
| | S.D. | 0.7773 | 0.1810 | |
| | MEDIAN | 0.208 | 0.116 | |
| | (MIN, MAX) | (0.060, 2.377) | (0.000, 0.535) | |

P-VALUEs: NP = non-parametric test

TABLE 20

5-oxo-ETE (ratio)

| PARAMETER | STATISTIC | Drug NS | Cardax | P-VALUE |
|---|---|---|---|---|
| Baseline | N | 6 | 6 | 0.532 NP |
| | MEAN | 0.200 | 0.033 | |
| | S.D. | 0.4033 | 0.0566 | |
| | MEDIAN | 0.030 | 0.000 | |
| | (MIN, MAX) | (0.000, 1.017) | (0.000, 0.138) | |
| 16 Hour Thio-glycollate | N | 8 | 8 | 0.998 |
| | MEAN | 0.056 | 0.056 | |
| | S.D. | 0.0375 | 0.0430 | |
| | MEDIAN | 0.047 | 0.067 | |
| | (MIN, MAX) | (0.000, 0.127) | (0.000, 0.100) | |
| 16 Hour Thio-glycollate/4 Hour Zymosan | N | 8 | 7 | 0.954 NP |
| | MEAN | 0.092 | 0.080 | |
| | S.D. | 0.0976 | 0.0400 | |
| | MEDIAN | 0.062 | 0.081 | |
| | (MIN, MAX) | (0.000, 0.319) | (0.038, 0.157) | |
| 72 Hour Thio-glycollate | N | 8 | 7 | 0.941 NP |
| | MEAN | 0.024 | 0.021 | |
| | S.D. | 0.0439 | 0.0354 | |
| | MEDIAN | 0.000 | 0.000 | |
| | (MIN, MAX) | (0.000, 0.104) | (0.000, 0.076) | |
| 72 Hour Thio-glycollate/4 Hour Zymosan | N | 8 | 7 | 0.013 NP |
| | MEAN | 0.288 | 0.063 | |
| | S.D. | 0.3784 | 0.0890 | |
| | MEDIAN | 0.156 | 0.048 | |
| | (MIN, MAX) | (0.062, 1.195) | (0.000, 0.258) | |

P-VALUEs: NP = non-parametric test

TABLE 21

ALV MAC %

| PARAMETER | STATISTIC | Drug NS | Cardax | P-VALUE |
|---|---|---|---|---|
| Baseline | N | 0 | 0 | N/A |
|  | MEAN |  |  |  |
|  | S.D. |  |  |  |
|  | MEDIAN |  |  |  |
|  | (MIN, MAX) |  |  |  |
| 16 Hour Thio-glycollate | N | 4 | 3 | 0.318 |
|  | MEAN | 13.500 | 3.000 |  |
|  | S.D. | 15.9687 | 1.0000 |  |
|  | MEDIAN | 7.000 | 3.000 |  |
|  | (MIN, MAX) | (3.000, 37.000) | (2.000, 4.000) |  |
| 16 Hour Thio-glycollate/4 Hour Zymosan | N | 0 | 0 | N/A |
|  | MEAN |  |  |  |
|  | S.D. |  |  |  |
|  | MEDIAN |  |  |  |
|  | (MIN, MAX) |  |  |  |
| 72 Hour Thio-glycollate | N | 3 | 3 | 0.668 |
|  | MEAN | 12.667 | 15.667 |  |
|  | S.D. | 10.0664 | 5.0332 |  |
|  | MEDIAN | 14.000 | 15.000 |  |
|  | (MIN, MAX) | (2.000, 22.000) | (11.000, 21.000) |  |
| 72 Hour Thio-glycollate/4 Hour Zymosan | N | 0 | 0 | N/A |
|  | MEAN |  |  |  |
|  | S.D. |  |  |  |
|  | MEDIAN |  |  |  |
|  | (MIN, MAX) |  |  |  |

TABLE 22

EOSIN %

| PARAMETER | STATISTIC | Drug NS | Cardax | P-VALUE |
|---|---|---|---|---|
| Baseline | N | 0 | 0 | N/A |
|  | MEAN |  |  |  |
|  | S.D. |  |  |  |
|  | MEDIAN |  |  |  |
|  | (MIN, MAX) |  |  |  |
| 16 Hour Thio-glycollate | N | 4 | 3 | 0.199 NP |
|  | MEAN | 2.750 | 6.000 |  |
|  | S.D. | 1.5000 | 4.3589 |  |
|  | MEDIAN | 2.000 | 4.000 |  |
|  | (MIN, MAX) | (2.000, 5.000) | (3.000, 11.000) |  |
| 16 Hour Thio-glycollate/4 Hour Zymosan | N | 0 | 0 | N/A |
|  | MEAN |  |  |  |
|  | S.D. |  |  |  |
|  | MEDIAN |  |  |  |
|  | (MIN, MAX) |  |  |  |
| 72 Hour Thio-glycollate | N | 4 | 3 | 0.326 |
|  | MEAN | 3.750 | 1.667 |  |
|  | S.D. | 2.7538 | 2.0817 |  |
|  | MEDIAN | 3.500 | 1.000 |  |
|  | (MIN, MAX) | (1.000, 7.000) | (0.000, 4.000) |  |
| 72 Hour Thio-glycollate/4 Hour Zymosan | N | 0 | 0 | N/A |
|  | MEAN |  |  |  |
|  | S.D. |  |  |  |
|  | MEDIAN |  |  |  |
|  | (MIN, MAX) |  |  |  |

P-VALUEs: NP = non-parametric test

TABLE 23

LYMPHS %

| PARAMETER | STATISTIC | Drug NS | Cardax | P-VALUE |
|---|---|---|---|---|
| Baseline | N | 0 | 0 | N/A |
|  | MEAN |  |  |  |
|  | S.D. |  |  |  |
|  | MEDIAN |  |  |  |
|  | (MIN, MAX) |  |  |  |
| 16 Hour Thio-glycollate | N | 4 | 3 | 0.037 |
|  | MEAN | 44.000 | 23.000 |  |
|  | S.D. | 10.8628 | 7.8102 |  |
|  | MEDIAN | 44.500 | 19.000 |  |
|  | (MIN, MAX) | (31.000, 56.000) | (18.000, 32.000) |  |
| 16 Hour Thio-glycollate/4 Hour Zymosan | N | 0 | 0 | N/A |
|  | MEAN |  |  |  |
|  | S.D. |  |  |  |
|  | MEDIAN (Q1, Q3) |  |  |  |
|  | (MIN, MAX) |  |  |  |
| 72 Hour Thio-glycollate | N | 4 | 3 | 0.838 |
|  | MEAN | 50.500 | 53.000 |  |
|  | S.D. | 18.6994 | 7.2111 |  |
|  | MEDIAN | 46.500 | 55.000 |  |
|  | (MIN, MAX) | (33.000, 76.000) | (45.000, 59.000) |  |
| 72 Hour Thio-glycollate/4 Hour Zymosan | N | 0 | 0 | N/A |
|  | MEAN |  |  |  |
|  | S.D. |  |  |  |
|  | MEDIAN |  |  |  |
|  | (MIN, MAX) |  |  |  |

TABLE 24

MONOS %

| PARAMETER | STATISTIC | Drug NS | Cardax | P-VALUE |
|---|---|---|---|---|
| Baseline | N | 0 | 0 | N/A |
|  | MEAN |  |  |  |
|  | S.D. |  |  |  |
|  | MEDIAN |  |  |  |
|  | (MIN, MAX) |  |  |  |
| 16 Hour Thio-glycollate | N | 4 | 3 | 0.139 |
|  | MEAN | 23.750 | 39.667 |  |
|  | S.D. | 9.6047 | 14.5717 |  |
|  | MEDIAN | 25.000 | 35.000 |  |
|  | (MIN, MAX) | (12.000, 33.000) | (28.000, 56.000) |  |
| 16 Hour Thio-glycollate/4 Hour Zymosan | N | 0 | 0 | N/A |
|  | MEAN |  |  |  |
|  | S.D. |  |  |  |
|  | MEDIAN |  |  |  |
|  | (MIN, MAX) |  |  |  |
| 72 Hour Thio-glycollate | N | 4 | 3 | 0.607 |
|  | MEAN | 32.250 | 27.000 |  |
|  | S.D. | 14.1745 | 9.5394 |  |
|  | MEDIAN | 28.000 | 32.000 |  |
|  | (MIN, MAX) | (21.000, 52.000) | (16.000, 33.000) |  |
| 72 Hour Thio-glycollate/4 Hour Zymosan | N | 0 | 0 | N/A |
|  | MEAN |  |  |  |
|  | S.D. |  |  |  |
|  | MEDIAN |  |  |  |
|  | (MIN, MAX) |  |  |  |

TABLE 25

NEUTRO %

| PARAMETER | STATISTIC | Drug NS | Drug Cardax | P-VALUE |
|---|---|---|---|---|
| Baseline | N | 0 | 0 | N/A |
|  | MEAN |  |  |  |
|  | S.D. |  |  |  |
|  | MEDIAN (MIN, MAX) |  |  |  |
| 16 Hour Thio-glycollate | N | 4 | 3 | 0.196 |
|  | MEAN | 10.500 | 25.333 |  |
|  | S.D. | 8.2664 | 17.8979 |  |
|  | MEDIAN (MIN, MAX) | 10.500 (2.000, 19.000) | 21.000 (10.000, 45.000) |  |
| 16 Hour Thio-glycollate/4 Hour Zymosan | N | 0 | 0 | N/A |
|  | MEAN |  |  |  |
|  | S.D. |  |  |  |
|  | MEDIAN (MIN, MAX) |  |  |  |
| 72 Hour Thio-glycollate | N | 4 | 3 | 0.267 |
|  | MEAN | 2.000 | 0.000 |  |
|  | S.D. | 2.7080 | 0.0000 |  |
|  | MEDIAN (MIN, MAX) | 1.000 (0.000, 6.000) | 0.000 (0.000, 0.000) |  |
| 72 Hour Thio-glycollate/4 Hour Zymosan | N | 0 | 0 | N/A |
|  | MEAN |  |  |  |
|  | S.D. |  |  |  |
|  | MEDIAN (MIN, MAX) |  |  |  |

TABLE 26

OTHER %

| PARAMETER | STATISTIC | Drug NS | Drug Cardax | P-VALUE |
|---|---|---|---|---|
| Baseline | N | 0 | 0 | N/A |
|  | MEAN |  |  |  |
|  | S.D. |  |  |  |
|  | MEDIAN (MIN, MAX) |  |  |  |
| 16 Hour Thio-glycollate | N | 4 | 3 | 0.359 NP |
|  | MEAN | 5.500 | 2.667 |  |
|  | S.D. | 3.6968 | 1.1547 |  |
|  | MEDIAN (MIN, MAX) | 5.000 (2.000, 10.000) | 2.000 (2.000, 4.000) |  |
| 16 Hour Thio-glycollate/4 Hour Zymosan | N | 0 | 0 | N/A |
|  | MEAN |  |  |  |
|  | S.D. |  |  |  |
|  | MEDIAN (MIN, MAX) |  |  |  |
| 72 Hour Thio-glycollate | N | 4 | 3 | 0.095 NP |
|  | MEAN | 0.750 | 2.333 |  |
|  | S.D. | 0.9574 | 0.5774 |  |
|  | MEDIAN (MIN, MAX) | 0.500 (0.000, 2.000) | 2.000 (2.000, 3.000) |  |
| 72 Hour Thio-glycollate/4 Hour Zymosan | N | 0 | 0 | N/A |
|  | MEAN |  |  |  |
|  | S.D. |  |  |  |
|  | MEDIAN (MIN, MAX) |  |  |  |

P-VALUEs: NP = non-parametric test

TABLE 27

REACTIVE %

| PARAMETER | STATISTIC | Drug NS | Drug Cardax | P-VALUE |
|---|---|---|---|---|
| Baseline | N | 0 | 0 | N/A |
|  | MEAN |  |  |  |
|  | S.D. |  |  |  |
|  | MEDIAN (MIN, MAX) |  |  |  |
| 16 Hour Thio-glycollate | N | 4 | 3 | 0.386 NP |
|  | MEAN | 0.000 | 0.333 |  |
|  | S.D. | 0.0000 | 0.5774 |  |
|  | MEDIAN (MIN, MAX) | 0.000 (0.000, 0.000) | 0.000 (0.000, 1.000) |  |
| 16 Hour Thio-glycollate/4 Hour Zymosan | N | 0 | 0 | N/A |
|  | MEAN |  |  |  |
|  | S.D. |  |  |  |
|  | MEDIAN (MIN, MAX) |  |  |  |
| 72 Hour Thio-glycollate | N | 4 | 3 | 0.266 NP |
|  | MEAN | 1.500 | 0.333 |  |
|  | S.D. | 1.2910 | 0.5774 |  |
|  | MEDIAN (MIN, MAX) | 1.500 (0.000, 3.000) | 0.000 (0.000, 1.000) |  |
| 72 Hour Thio-glycollate/4 Hour Zymosan | N | 0 | 0 | N/A |
|  | MEAN |  |  |  |
|  | S.D. |  |  |  |
|  | MEDIAN (MIN, MAX) |  |  |  |

P-VALUEs: NP = non-parametric test

TABLE 28

RES EP %

| PARAMETER | STATISTIC | Drug NS | Drug Cardax | P-VALUE |
|---|---|---|---|---|
| Baseline | N | 0 | 0 | N/A |
|  | MEAN |  |  |  |
|  | S.D. |  |  |  |
|  | MEDIAN (MIN, MAX) |  |  |  |
| 16 Hour Thio-glycollate | N | 4 | 3 | N/A |
|  | MEAN | 0.000 | 0.000 |  |
|  | S.D. | 0.0000 | 0.0000 |  |
|  | MEDIAN (MIN, MAX) | 0.000 (0.000, 0.000) | 0.000 (0.000, 0.000) |  |
| 16 Hour Thio-glycollate/4 Hour Zymosan | N | 0 | 0 | N/A |
|  | MEAN |  |  |  |
|  | S.D. |  |  |  |
|  | MEDIAN (MIN, MAX) |  |  |  |
| 72 Hour Thio-glycollate | N | 4 | 3 | 0.564 NP |
|  | MEAN | 0.500 | 0.000 |  |
|  | S.D. | 1.0000 | 0.0000 |  |
|  | MEDIAN (MIN, MAX) | 0.000 (0.000, 2.000) | 0.000 (0.000, 0.000) |  |
| 72 Hour Thio-glycollate/4 Hour Zymosan | N | 0 | 0 | N/A |
|  | MEAN |  |  |  |
|  | S.D. |  |  |  |
|  | MEDIAN (MIN, MAX) |  |  |  |

P-VALUEs: NP = non-parametric test

TABLE 29

RBC

| PARAMETER | STATISTIC | Drug | | P-VALUE |
|---|---|---|---|---|
| | | NS | Cardax | |
| Baseline | N | 0 | 0 | N/A |
| | MEAN | | | |
| | S.D. | | | |
| | MEDIAN (MIN, MAX) | | | |
| 16 Hour Thio-glycollate | N | 4 | 3 | 0.035 |
| | MEAN | 11.250 | 449.33 | |
| | S.D. | 14.6373 | 315.937 | |
| | MEDIAN | 6.500 | 350.00 | |
| | (MIN, MAX) | (0.000, 32.000) | (195.00, 803.00) | |
| 16 Hour Thio-glycollate/4 Hour Zymosan | N | 0 | 0 | N/A |
| | MEAN | | | |
| | S.D. | | | |
| | MEDIAN (MIN, MAX) | | | |
| 72 Hour Thio-glycollate | N | 4 | 3 | 0.152 |
| | MEAN | 3216.3 | 90.333 | |
| | S.D. | 3130.03 | 41.3562 | |
| | MEDIAN | 2665.0 | 69.000 | |
| | (MIN, MAX) | (95.000, 7440.0) | (64.000, 138.00) | |
| 72 Hour Thio-glycollate/4 Hour Zymosan | N | 0 | 0 | N/A |
| | MEAN | | | |
| | S.D. | | | |
| | MEDIAN (MIN, MAX) | | | |

TABLE 30

WBC

| PARAMETER | STATISTIC | Drug | | P-VALUE |
|---|---|---|---|---|
| | | NS | Cardax | |
| Baseline | N | 0 | 0 | N/A |
| | MEAN | | | |
| | S.D. | | | |
| | MEDIAN (MIN, MAX) | | | |
| 16 Hour Thio-glycollate | N | 4 | 3 | 0.890 |
| | MEAN | 556.00 | 528.67 | |
| | S.D. | 110.761 | 365.467 | |
| | MEDIAN | 540.00 | 475.00 | |
| | (MIN, MAX) | (451.00, 693.00) | (193.00, 918.00) | |
| 16 Hour Thio-glycollate/4 Hour Zymosan | N | 0 | 0 | N/A |
| | MEAN | | | |
| | S.D. | | | |
| | MEDIAN (MIN, MAX) | | | |
| 72 Hour Thio-glycollate | N | 4 | 3 | 0.377 NP |
| | MEAN | 316.50 | 435.33 | |
| | S.D. | 83.5244 | 134.448 | |
| | MEDIAN | 351.50 | 448.00 | |
| | (MIN, MAX) | (193.00, 370.00) | (295.00, 563.00) | |
| 72 Hour Thio-glycollate/4 Hour Zymosan | N | 0 | 0 | N/A |
| | MEAN | | | |
| | S.D. | | | |
| | MEDIAN (MIN, MAX) | | | |

P-VALUEs: NP = non-parametric test

TABLE 31 oY/F (mmol/mol)

| PARAMETER | STATISTIC | Drug | | P-VALUE |
|---|---|---|---|---|
| | | NS | Cardax | |
| Baseline | N | 6 | 6 | 0.475 |
| | MEAN | 0.797 | 0.595 | |
| | S.D. | 0.5958 | 0.3001 | |
| | MEDIAN | 0.602 | 0.565 | |
| | (MIN, MAX) | (0.171, 1.600) | (0.196, 1.074) | |
| 16 Hour Thio-glycollate | N | 8 | 8 | 0.128 NP |
| | MEAN | 0.314 | 0.678 | |
| | S.D. | 0.1671 | 0.4693 | |
| | MEDIAN | 0.385 | 0.521 | |
| | (MIN, MAX) | (0.106, 0.491) | (0.219, 1.562) | |
| 16 Hour Thio-glycollate/4 Hour Zymosan | N | 7 | 7 | 0.021 NP |
| | MEAN | 0.501 | 0.145 | |
| | S.D. | 0.4623 | 0.0679 | |
| | MEDIAN | 0.220 | 0.117 | |
| | (MIN, MAX) | (0.161, 1.218) | (0.092, 0.280) | |
| 72 Hour Thio-glycollate | N | 8 | 7 | 0.742 |
| | MEAN | 0.281 | 0.257 | |
| | S.D. | 0.1309 | 0.1461 | |
| | MEDIAN | 0.277 | 0.198 | |
| | (MIN, MAX) | (0.099, 0.525) | (0.094, 0.541) | |
| 72 Hour Thio-glycollate/4 Hour Zymosan | N | 8 | 7 | 0.385 NP |
| | MEAN | 0.162 | 0.249 | |
| | S.D. | 0.1000 | 0.3448 | |
| | MEDIAN | 0.149 | 0.118 | |
| | (MIN, MAX) | (0.028, 0.383) | (0.090, 1.030) | |

P-VALUES: NP = non-parametric test

In this patent, certain U.S. patents, U.S. patent applications, and other materials (e.g., articles) have been incorporated by reference. The text of such U.S. patents, U.S. patent applications, and other materials is, however, only incorporated by reference to the extent that no conflict exists between such text and the other statements and drawings set forth herein. In the event of such conflict, then any such conflicting text in such incorporated by reference U.S. patents, U.S. patent applications, and other materials is specifically not incorporated by reference in this patent.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

REFERENCES

The following references are specifically incorporated herein by reference:

U.S. Patent Applications

U.S. patent application Ser. No. 10/793,670; Filed: Mar. 4, 2004; Inventor(s): Lockwood et al.; Title: "CAROTENOID ANALOGS OR DERIVATIVES FOR THE INHIBITION AND AMELIORATION OF DISEASE"

U.S. Patent Documents

U.S. Pat. No. 5,871,766 February, 1999 Hennekens

OTHER REFERENCES

Axford-Gatley, R. A, and Wilson, J. G. (1991). Reduction of experimental myocardial infarct size by oral administration of alpha-tocopherol. Cardiovasc Res 25: 89-92.

Baxter, G. F., and Yellon, D. M. (1993). Attenuation of reperfusion-induced ventricular fibrillation in the rat isolated hypertrophied heart by preischemic diltiazem treatment. Cardiovasc Drugs Ther 7: 225-231.

Blaustein, A. S., Schine, L., Brooks, W. W., Franburg, B. L, and Bing, O. H. (1986). Influence of exogenously generated oxidant species on myocardial function. Am J Physiol 250: H595-H599.

Bolli, R., Patel, B. S., Zhu, W. X., et al. (1987). The iron chelator desferioxamine attenuates postischemic ventricular dysfunction. Am J Physiol 253: H1372-H1380.

Bolli, R., Zhu, W. X., and Hartley, C. J. (1987). Attenuation of dysfunction in the postischemic "stunned" myocardium by dimethylurea. Circulation 76: 458-468.

Bolli, R., Jeroudi, M. O., Patel, B. S., et al. (1989). Direct evidence that oxygen-derived free radicals contribute to post-ischemic myocardial dysfunction in the intact dog. Proc Natl Acad Sci USA 86: 4695-4699.

Chopra, M., McMurray, J., Stewart, J., Dargie, H. J., and Smith, W. E. (1990). Free radical scavenging: potentially beneficial action of thiol-containing angiotensin-converting enzyme inhibitors. Biochem Soc Trans 18: 1184-1185.

Conorev, E. A., Sharov, V. G., and Saks, V. A. (1991). Improvement of contractile recovery of isolated rat heart after cardioplegic ischemic arrest with endogenous phosphocreatine: involvement of antiperoxidative effect? Cardiovasc Res 25: 164-171.

Duilio, C., Ambrosio, G., Kuppusamy, P., Dipaula, A., Becker, L. C., and Zweier, J. L. (2001). Neutrophils are primary source of $O_2$ radicals during reperfusion after prolonged myocardial ischemia. Am J Physiol Heart Circ Physiol 280: H2649-H2657.

Goto, S., Kogure, K., Abe, K., Kimata, Y., Kitahama, K., Yamashita, E., and Terada, H. (2001). Efficient radical trapping at the surface and inside the phospholipids membrane is responsible for highly potent antiperoxidative activity of the carotenoid astaxanthin. Biochimica et Biophysica Acta 1512: 251-258.

Hearse, D. J., Manning, A. S., Downey, J. M., and Yellon, D. M. (1986). Xanthine oxidase: a critical mediator of myocardial injury during ischemia and reperfusion. Acta Physiol Scand 548: 65-74.

Horwitz, L. D., Kong, Y., and Robertson, A. D. (1999). Timing of treatment for myocardial reperfusion injury. J Cardiovasc Pharmacol 33 (1): 19-29.

Johansson, M. H., Deinum, J., Marklund, S. L., and Sjodquist, P. O. (1990). Recombinant human extracellular superoxide dismutase reduces concentration of oxygen free radicals in the reperfused rat heart. Cardiovasc Res 24: 500-503.

Kimura, Y., Engelman, R. M., Rousou, J., Flack, J., Iyengar, J., and Das, D. K. (1992). Moderation of myocardial ischeraia reperfusion injury by calcium channel and calmodulin receptor inhibition. Heart Vessels 7: 189-195.

Levy; Y., Bartha, P., Ben-Amotz, A., Brook, J. G., Dankner, G., Lin, S., and Hammerman, H. (1998). Plasma antioxidants and lipid peroxidation in acute myocardial infarction and thrombolysis. J Am Coll Nutr 17 (4): 337-341.

Mahaffey, K. W., Puma, J. A., Barbagelata, N. A., DiCarli, M. F., Leesar, M. A., Browne, K. F., Eisenberg, P. R., Bolli, R., Casas, C., Molina-Viamonte, V., Orlandi, C., Blevins, R., Gibbons, R. J., Califf, R. M., Granger, C. B. (1999). Adenosine as an adjunct to thrombolytic therapy for acute myocardial infarction. J Am Coll Cardiol 34(6): 1711-1720.

McMurray, J., and Chopra, M. (1991). Influence of ACE inhibitors on free radicals and reperfusion injury: pharmacological curiosity or therapeutic hope? Br J Pharmacol 31: 373-379.

Petty, M. A., Dow, J., Grisar, J. M., and De-Jong, W. Effect of a cardioselective alpha-tocopherol analogue on reperfusion injury in rats induced by myocardial ischemia. Eur J Pharmacol 192: 383-388.

Sajkowska, A., Wykretowicz, A., Szczepanik, A., Kempa, M., Minczykowski, A., and Wysocki, H. (1999). Fibrinolytic therapy and n-acetylcysteine in the treatment of patients with acute myocardial infarction: its influence on authentic plasma hydroperoxide levels and polymorphonuclear neutrophil oxygen metabolism. Cardiology 91: 60-65.

Schaer, G. L., Spaccavento, L. J., Browne, K. F., Krueger, K. A., Krichbau, D., Phelan, J. M., Fletcher, W. O., Grines, C. L., Edwards, S., Jolly, M. K., and Gibbons, R. J. (1996). Beneficial effects of RheothRx injection in patients receiving thrombolytic therapy for acute myocardial infarction. Results of a randomized, double-blind, placebo-controlled trial. Circulation 94(3): 298-307.

Sethi, R., Takeda, N., Nagano, M., and Dhalla, N. S. (2000). Beneficial effects of vitamin E treatment in acute myocardial infarction. J Cardiovasc Pharmacol Ther 5: 51-58.

Shuter, S. L., Davies, M. J., Garlick, P. B, Hearse, D. J., and Slater, T. F. (1990). Studies on the effects of of antioxidants and inhibitors of radical generation on free radical production in the reperfused rat heart using electron spin resonance spectroscopy. Free Radic Res Commun 9: 223-232.

Simpson, P. J., and Lucchesi, B. R. (1987). Free radicals and myocardial ischemia and reperfusion injury. J Lab Clin Med 110: 13-30.

Singh, R. B., Niaz, M. A., Sharma, J. P., Kumar, R., Bishnoi, I., and Begom, R. (1994). Plasma levels of antioxidant vitamins and oxidative stress in patients with acute myocardial infarction. Acta Cardiologica Vol. XLIX 5: 441-452.

Such, L., Morcillo, E., Chorro, F. J., et al. Beneficial effects of N-acetylcysteine on acute myocardial infarction in open chest dogs. Arch Pharmacol Toxicol 12: 37-40.

Rogers, M., Berestecky, J. M., Hossain, M. Z., Guo, H., Kadle, R., Nicholson, B. J., and Bertram, J. S. (1990). Retinoid-enhanced gap junctional communication is achieved by increased levels of connexin 43 mRNA and protein. Molecular Carcinogenesis 3: 335-343.

Bertram, J. S. (1999). Carotenoids and gene regulation. Nutrition Reviews 57(6): 182-191.

Gutstein, D. E., Morley, G. E., Tamaddon, H., Vaidya, D., Schneider, M. D., Chen, J., Chien, K. R., Stuhlmann, H., Fishman, G. I. (2001). Conduction slowing and sudden arrhythmic death in mice with cardiac-restricted inactivation of connexin 43. Circulation Research: 333-339.

Dulio, C., Ambrosio, G., Kuppusamy, P., Dipaula, A., Becker, L. C., Zweier, J. L. (2001). Neutrophils are primary source of $O_2$ radicals during reperfusion after prolonged myocardial ischemia. Am J Physiol Heart Circ Physiol 280: H2649-H2657.

Liao, M.-L., Wang, S. Y., Chung, C., Liang, Y.-T., Sejb, P. A., (1988). Synthesis of L-Ascorbate 6-Phosphate. Carbohydrate Research 176: 73-77.

Bock, K., Lundt, I., Pedersen, C., (1979). Preparation of Some Bromodeoxyaldonic Acids. Carbohydrate Research 68: 313-319.

Stuber, H. A., Tolbert, B. M., (1978). A New Synthesis of L-threo-Hex-2-Enaro-1,4-Lactone ("Saccharoascorbic" Acid): A Method for the Protection of the Enediol of Ascorbic Acid. Carbohydrate Research 60: 251-258.

G. Britton, Structure and properties of carotenoids in relation to function, FASEB J. 9 (1995) 1551-1558.

A. M. Papas, Antioxidant status: diet, health and disease; Part I: Factors affecting antioxidant status and its role, Mature Medicine (1999) 315-319.

W. Miki, Biological functions and activities of animal carotenoids, Pure Appl. Chemistry 63 (1991) 141-146.

S. F. Lockwood, S. O'Malley, G. L. Mosher, Improved aqueous solubility of crystalline astaxanthin (3,3'-dihydroxy-beta, beta-carotene-4,4'-dione) by Captisol(R) (sulfobutyl ether beta-cyclodextrin), J. Pharm. Sci. 92 (2003) 922-926.

M. Buchwaldt, W. P. Jencks, Optical properties of astaxanthin solutions and aggregates, Biochemistry 7 (1968) 834-843.

V. Salares, N. Young, P. Carey, H. Bernstein, Excited state (exciton) interactions in polyene aggregates, J. Raman Spectr. 6 (1977) 282-288.

F. Zsila, Z. Bikádi, J. Deli, M. Simonyi, Chiral detection of carotenoid assemblies, Chirality 13 (2001) 446-453.

R. K. Müller, K. Bernhard, H. Mayer, A. Ruttimann, M. Vecchi, Contribution to the analytical separation and the synthesis of 3-hydroxy-4-oxocarotenoids, Helv. Chim. Acta 63 (1980) 1654-1664.

F. Zsila, Z. Bikádi, M. Simonyi, Induced chirality upon crocetin binding to human serum albumin: origin and nature, Tetrahedron: Assymmetry 12 (2001) 3125-3137.

T. Peters, All About Albumin, Academic Press, San Diego (CA), 1996.

H. Watanabe, S. Tanase, K. Nakajou, T. Maruyama, U. Kragh-Hansen, M. Otagiri, Role of Arg-410 and Tyr-411 in human serum albumin for ligand binding and esterase-like activity, Biochem. J. 349 (2000) 813-819.

U. Kragh-Hansen, V. Chuang, M. Otagiri, Practical aspects of the ligand-binding and enzymatic properties of human serum albumin, Biol. Pharm. Bull. 25 (2002) 695-704.

F. Zsila, Z. Bikádi, Z. Keresztes, J. Deli, M. Simonyi, Investigation of the self-organization of lutein and lutein diacetate by electronic absorption, circular dichroism spectroscopy, and atomic force microscopy, J. Phys. Chem. B 105 (2001) 9413-9421.

K. Bernhard, G. Englert, H. Mayer, R. K. Muller, A. Ruttimann, M. Vecchi, E. Widmer E, R. Zell, Synthesis of optically-active natural carotenoids and structurally related-compounds. 9. Synthesis of (3R)-hydroxyechinenone, (3R,3'R)-adonixanthin and (3R,3'S)-adonixanthin, (3R)-adonirubin, their optical antipodes and related-compounds, Helv. Chim. Acta 64 (1981) 2469-2484.

V. Sturzenegger, R. Buchecker, G. Wagniere, Classification of the CD spectra of carotenoids, Helv. Chim. Acta 63 (1980) 1074-1092.

A. G. Andrewes, G. Borch, S. Liaaen-Jensen, G. Snatzke, Animal carotenoids. 9. On the absolute configuration of astaxanthin and actinioerythrin, Acta Chem Scand. B 28 (1974) 730-736.

B. F. Lutnaes, O. R. Gautun, S. Liaaen-Jensen, Is (9Z)-"meso"-zeaxanthin optically active? Chirality 13 (2001) 224-229.

Z. Bikádi, F. Zsila, J. Deli, G. Mády, M. Simonyi, The supramolecular structure of self-assembly formed by capsanthin derivatives, Enantiomer 7 (2002) 67-76.

K. Noack, A. J. Thomson, Conformation and optical-activity of all-trans, mono-cis, and di-cis carotenoids-temperature-dependent circular-dichroism, Helv. Chim. Acta 62 (1979) 1902-1921.

K. Noack, A. J. Thomson, Temperature and concentration dependent circular-dichroism of mono-cis and di-cis isomers of (3R,3'S)-astaxanthin diacetate, Helv. Chim. Acta 64 (1981) 2383-2392.

N. Harada, K. Nakanishi, Circular Dichroic Spectroscopy—Exciton Coupling in Organic Stereochemistry, University Science Books, Mill Valley (Calif.), 1983.

N. Harada, Y. Takuma, H. Uda, Circular dichroic power due to chiral exciton coupling between two polyacene chromophores, J. Am. Chem. Soc. 100 (1978) 4029-4036.

J-K. Choi, J. Ho, S. Curry, D. Qin, R. Bittman, J. Hamilton, Interactions of very long-chain saturated fatty acids with serum albumin, J. Lipid Res. 43 (2002) 1000-1010.

S. Curry, P. Brick, N. P. Franks, Fatty acid binding to human serum albumin: new insights from crystallographic studies, Biochim Biophys. Acta 1441 (1999) 131-140.

I. Petitpas, T. Grüne, A. Bhattacharya, S. Curry, Crystal structures of human serum albumin complexed with monounsaturated and polyunsaturated fatty acids, J. Mol. Biol. 314 (2001) 955-960.

A. A. Bhattacharya, T. Grüne, S. Curry, Crystallographic analysis reveals common modes of binding of medium and long-chain fatty acids to human serum albumin, J. Mol. Biol. 303 (2000) 721-732.

Cross, C. E., B. Halliwell, E. T. Borish, W. A. Pryor, B. N. Ames, R. L. Saul, J. M. McCord, and D. Harman. (1987) Oxygen radicals and human disease. *Ann. Intern. Med.,* 107:526-545.

Zhang, L.-X., Cooney, R. V., and Bertram, J. S. (1992) Carotenoids up-regulate connexin 43 gene expression independent of their pro-vitamin A or antioxidant properties. *Cancer Res.,* 52, 5707-5712.

Peters, N. S. (1995) Myocardial gap junction organization in ischemia and infarction. *Microsc. Res. Tech.,* 31, 375-386.

Zhang, L.-X. and Bertram J. S. (1994) Assays for Regulation of Gap Junctional Communication and Connexin expression by Carotenoids. In Packer, L. (ed.) *Oxygen radicals in biological systems, Part C. In: Methods in Enzymology:* Vol 234. Academic Press, Orlando, pp 235-44.

Hossain, M. Z., Zhang, L.-X., and Bertram, J. S. (1993) Retinoids and carotenoids upregulate gap junctional communication: correlation with enhanced growth control and cancer prevention. In Hall, J. E., Zampighi, G. A., and Davies, R. M. (eds.) *Progess in Cell Research Vol.* 3: *Gap Junctions.* Elsiever, Amsterdam, pp 301-9.

Perkins, G., Goodenough, D., and Sosinsky, G. (1997) Three-dimensional structure of the gap junction connexon. *Biophysical Journal*, 72, 533-544.

Saez, J. C., Martinez, A. D., Branes, M. C., and Gonzalez, H. E. (1998) Regulation of gap junctions by protein phosphorylation. *Braz. J. Med. Biol. Res.*, 31, 593-600.

A. S. Moore, and A. M. Papas, Biochemistry and health significance of Vitamin E, J. Adv. Med. 9 (1996) 11-29.

P. Di Mascio, T. P. Devasagayam, S. Kaiser, and H. Sies, Carotenoids, tocopherols and thiols as biological singlet molecular oxygen quenchers, Biochem. Soc. Trans. 18 (1990) 1054-1056.

P. Di Mascio, M. E. Murphy, and H. Sies, Antioxidant defense systems: the role of carotenoids, tocopherols, and thiols, Am. J. Clin. Nutr. 53 (1991) 194S-200S.

J. H. Tinkler, F. Böhm, W. Schalch, and T. G. Truscott, Dietary carotenoids protect human cells from damage, J. Photochem. Photobiol. B. 26 (1994) 283-285.

H. Jyonouchi, S. Sun, K. Iijima, and M. D. Gross, Antitumor activity of astaxanthin and its mode of action, Nutr. Cancer 36 (2000) 59-65.

A. Kistler, H. Liechti, L. Pichard, E. Wolz, G. Oesterhelt, A. Hayes, and P. Maurel, Metabolism and CYP-inducer properties of astaxanthin in man and primary human hepatocytes, Arch. Toxicol. 75 (2002) 665-675.

A. Mortensen, L. H. Skibsted, J. Sampson, C. Rice-Evans, and S. A. Everett, Comparative mechanisms and rates of free radical scavenging by carotenoid antioxidants, FEBS Lett. 418 (1997) 91-97.

J. Terao, Antioxidant activity of beta-carotene-related carotenoids in solution, Lipids 24 (1989) 659-661.

P. Palozza, and N. I. Krinsky, Astaxanthin and canthaxanthin are potent antioxidants in a membrane model, Arch. Biochem. Biophys. 297 (1992) 291-295.

B. P. Lim, A. Nagao, J. Terao, K. Tanaka, T. Suzuki, and K. Takama, Antioxidant activity of xanthophylls on peroxyl radical-mediated phospholipid peroxidation, Biochim. Biophys. Acta 1126 (1992) 178-184.

B. N. Ames, M. K. Shigenaga, and T. M. Hagen, Oxidants, antioxidants, and the degenerative diseases of aging, Proc. Natl. Acad. Sci. U.S.A. 90 (1993) 7915-7922.

S. Mayne, Beta-carotene, carotenoids, and disease prevention in humans, FASEB J. 10 (1996) 690-701.

V. R. Salares, N. M. Young, H. J. Bernstein, and P. R. Carey, Resonance Raman spectra of lobster shell carotenoproteins and a model astaxanthin aggregate. A possible photobiological function for the yellow protein, Biochemistry 16 (1977) 4751-4756.

F. Zsila, J. Deli, Z. Bikadi, and M. Simonyi, Supramolecular assemblies of carotenoids, Chirality 13 (2001) 739-744.

Z. Bikadi, F. Zsila, J. Deli, G. Mady, and M. Simonyi, The supramolecular structure of self-assembly formed by capsanthin derivatives, Enantiomer 7 (2002) 67-76.

C. V. Serrano, Jr., E. A. Mikhail, P. Wang, B. Noble, P. Kuppusamy, and J. L. Zweier, Superoxide and hydrogen peroxide induce CD18-mediated adhesion in the postischemic heart, Biochim. Biophys. Acta 1316 (1996) 191-202.

E. W. Gabrielson, P. Kuppusamy, A. C. Povey, J. L. Zweier, and C. C. Harris, Measurement of neutrophil activation and epidermal cell toxicity by palytoxin and 12-O-tetradecanoylphorbol-13-acetate, Carcinogenesis 13 (1992) 1671-1674.

C. Lee, K. Miura, X. Liu, and J. L. Zweier, Biphasic regulation of leukocyte superoxide generation by nitric oxide and peroxynitrite, J. Biol. Chem. 275 (2000) 38965-38972.

M. Kurashige, E. Okimasu, M. Inoue, and K. Utsumi, Inhibition of oxidative injury of biological membranes by astaxanthin, Physiol. Chem. Phys. Med. NMR 22 (1990) 27-38.

E. Oliveros, A. M. Braun, T. Aminian-Saghafi, and H. R. Sliwka, Quenching of singlet oxygen by carotenoid derivatives: kinetic analysis by near-infrared luminescence, New J. Chem. 18 (1994) 535-539.

F. Zsila, J. Deli, and M. Simonyi, Color and chirality: carotenoid self-assemblies in flower petals, Planta 213 (2001) 937-942.

Osterlie M, Bjerkeng B, Liaaen-Jensen S. 2000. Plasma appearance and distribution of astaxanthin E/Z and R/S isomers in plasma lipoproteins of men after single dose administration of astaxanthin. J. Nutr. Biochem. 10: 482-490.

Jewell C, O'Brien N M. 1999. Effect of dietary supplementation with carotenoids on xenobiotic metabolizing enzymes in the liver, lung, kidney and small intestine of the rat. Br. J. Nutr. 81(3): 235-42.

Kurihara H, Koda H, Asami S, Kiso Y, Tanaka T. 2002. Contribution of the antioxidative property of astaxanthin to its protective effect on the promotion of cancer metastasis in mice treated with restraint stress. Life Sci. (21): 2509-20.

Kang J O, Kim S J, Kim H. 2001. Effect of astaxanthin on the hepatotoxicity, lipid peroxidation and antioxidative enzymes in the liver of CCl4-treated rats. Methods Find Exp Clin Pharmacol. 23(2): 79-84.

Kim H P, Kim S Y, Lee E J, Kim Y C, Kim Y C. 1997. Zeaxanthin dipalmitate from *Lycium chinense* has hepatoprotective activity. Res. Comm. Mol. Path. Pharm. 97: 301-314.

Leist M, Gantner F, Bohlinger I, Tiegs G, Germann P G, Wendel A. 1995. Tumor necrosis factor-induced hepatocyte apoptosis precedes liver failure in experimental murine shock models. Am. J. Pathol. 146: 1220-1234.

Ding, Y. J. Chem. Soc., Perkin Trans. 1, 2000, 1651-1655.

Bertram, J. S., Pung, A., Churley, M., Kappock, T. J. I., Wilkins, L. R., and Cooney, R. V. (1991) Diverse carotenoids protect against chemically induced neoplastic transformation. *Carcinogenesis*, 12, 671-678.

Pung, A., Rundhaug, J. E., Yoshizawa, C. N., and Bertram, J. S. (1988) b-Carotene and canthaxanthin inhibit chemically- and physically-induced neoplastic transformation in 10T1/2 cells. *Carcinogenesis*, 9, 1533-1539.

Reznikoff, C. A., Bertram, J. S., Brankow, D. W., and Heidelberger, C. (1973) Quantitative and Qualitative Studies of Chemical Transformation of Cloned C3H Mouse Embryo Cells Sensitive to Postconfluence Inhibition of Cell Division. *Cancer Research*, 33, 2339-2349.

R. Merriman and J. S. Bertram. Reversible inhibition by retinoids of 3-methylcholanthrene-induced neoplastic transformation in C3H10T1/2 cells. *Cancer Res.* 39:1661-1666, 1979.

J. S. Bertram. Neoplastic Transformation in Cell Cultures: In Vitro/In-Vivo Correlations. *IARC Sci. Pub.* 67:77-91, 1985.

J. S. Bertram, M. Z. Hossain, A. Pung, and J. E. Rundhaug. Development of in vitro systems for chemoprevention research. *Prev. Med.* 18:562-575, 1989.

W. Aoi, Y. Naito, K. Sakuma, M. Kuchide, H. Tokuda, T. Maoka, S. Toyokuni, S. Oka, M. Yasuhura, and T. Toshikawa. Astaxanthin limits exercise-induced skeletal and cardiac muscle damage in mice. *Antioxidants & Redox Signaling* 5(1):139-144, 2003.

K. Ohgami, K. Shiratori, S. Kotake, T. Nishida, N. Mizuki, K. Yazawa, and S. Ohno. Effects of astaxanthin on lipopolysaccharide-induced inflammation in vitro and in vivo. *Investigative Ophthalmology & Visual Science* 44(6): 2694-2701, 2003.

Barrett, T. D., Hennan, J. K., Marks, R. M., and Lucchesi, B. R. (2002). C-reactive protein associated increase in myocardial infarct size after ischemia/reperfusion. *Journal of Pharmacology and Experimental Therapeutics* 303(3): 1007-1013.

A. A. Spector, J A Gordon and S A Moore (1988) "Hydroxyeicosatetraenoic Acids (HETEs)". Prog. Lipid res. vol 27, pp 271-323.

J M Drazen, E Isreal and P M O'Byrne (1999) "Treatment of Asthma with Drugs Modifying the Leukotriene Pathway". New Engl. J. Med. vol. 340(3), pp 197-206.

What is claimed is:

1. A method of inhibiting or reducing an inflammatory response in a subject comprising administering to a subject in need thereof an effective amount of a pharmaceutically acceptable formulation comprising a synthetic carotenoid analog or a carotenoid derivative;

wherein the carotenoid analog or derivative has the structure

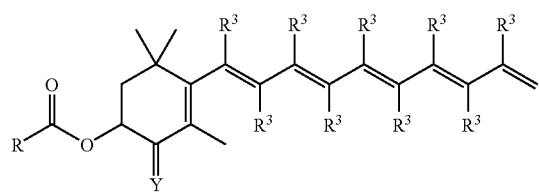

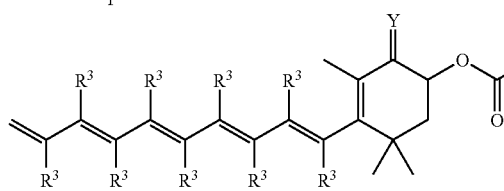

wherein each $R^3$ is independently hydrogen or methyl;
where each Y is independently O or $H_2$;
where each R is independently -alkyl-$NR^2_3{}^+$, -alkyl-$NR^2_2$, -aryl-$NR^2_3{}^+$, -alkyl-$CO_2{}^-$, -aryl-$CO_2{}^-$, -alkyl-$CO_2R^6$, -alkyl-$CO_2R^7$, —$OR^8$, -amino acid-$NH_2$, -amino acid-$NH_3{}^+$, -phosphorylated amino acid-$NH_3{}^+$, polyethylene glycol, dextran, H, alkyl, aryl, -alkyl-O—$PO_2$—O-alkyl-$NR^2_3{}^+$,

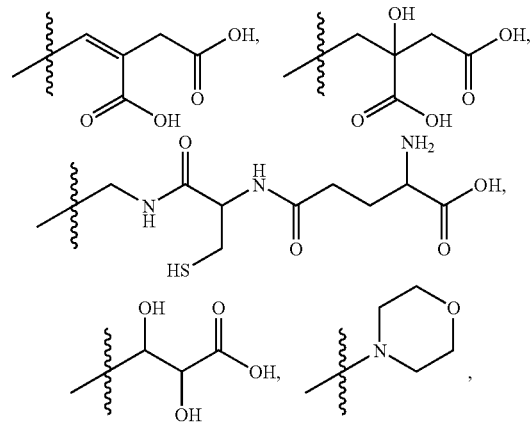

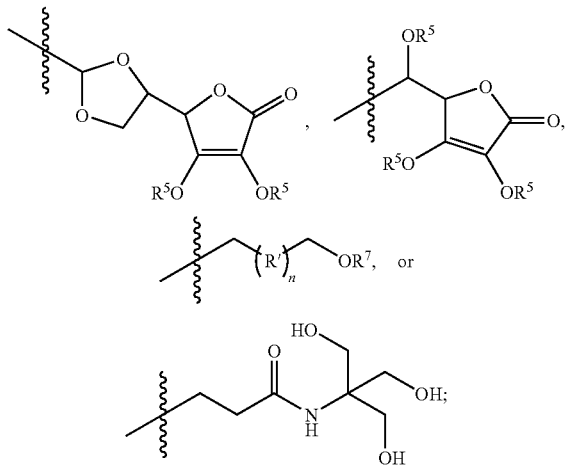

where each $R^2$ is independently H, alkyl, or aryl;
wherein R' is -alkyl-O, alkyl, or aryl;
wherein n is 1 to 9
wherein each $R^5$ is independently H;
wherein $R^6$ is alkyl, —$CH_2$—CH(OH)—$CH_2$—O—$PO_2$—O-alkyl-$NR^2_3{}^+$,

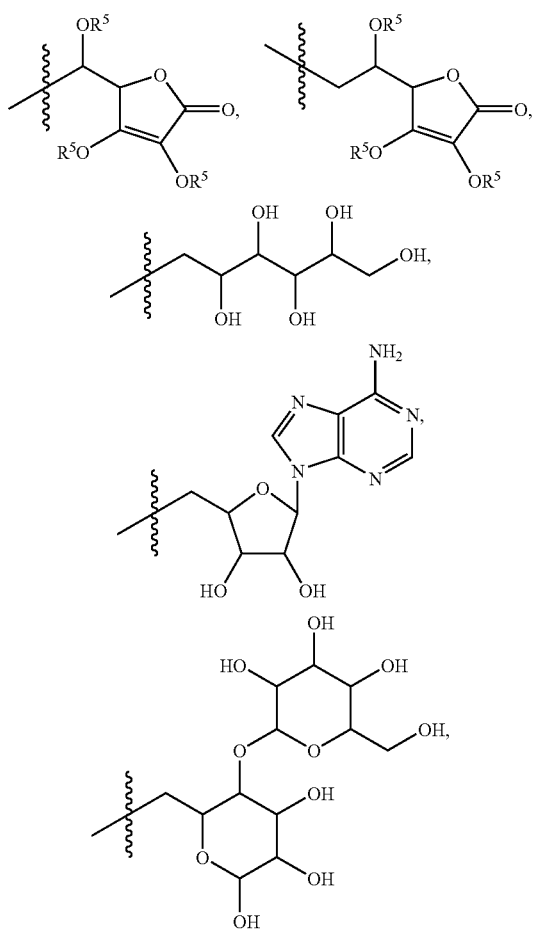

-continued

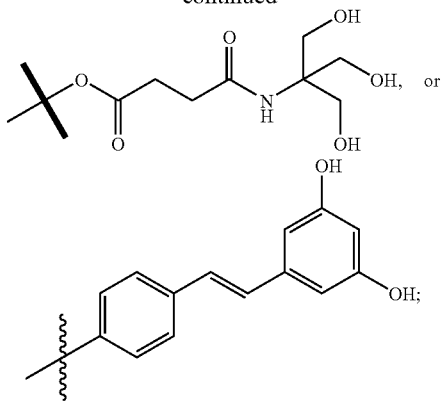

and wherein $R^7$ is -alkyl-$NR^2_3{}^+$, -aryl-$NR^2_3{}^+$, -alkyl-$CO_2{}^-$, -aryl-$CO_2{}^-$, -amino acid-$NH_3{}^+$, -phosphorylated amino acid-$NH_3{}^+$, polyethylene glycol, dextran, H, alkyl,

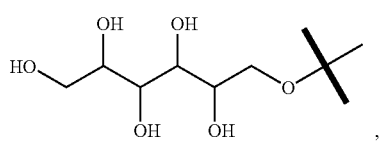

Group IA metal, or aryl;

where each $R^8$ is independently -alkyl-$NR^2_3{}^+$, -alkyl-$NR^2_2$, -aryl-$NR^2_3{}^+$, -alkyl-$CO_2{}^-$, -aryl-$CO_2{}^-$, -alkyl-$CO_2H$, -alkyl-$CO_2R^6$, -alkyl-$CO_2R^7$, —$OR^7$, -amino acid-$NH_2$, -amino acid-$NH_3{}^+$, -phosphorylated amino acid-$NH_3{}^+$, polyethylene glycol, dextran, H, alkyl, or aryl; and wherein said effective amount is sufficient to reduce the amount of at least one eicosanoid resulting from 5-Lipoxygenase activity.

2. The method of claim 1, wherein the formulation is administered to the subject prior to the onset of an inflammatory response or during an inflammatory response.

3. The method of claim 1, wherein the subject is a mammal.

4. The method of claim 1, wherein the subject is human.

5. The method of claim 1, wherein the dosage of the carotenoid analog or derivative comprising the formulation that is administered to the subject is in the range of about 10 mg/kg body weight to about 1000 mg/kg body weight.

6. The method of claim 1, wherein the formulation is adapted to be administered orally.

7. The method of claim 1, wherein the formulation is adapted to be administered parenterally.

8. The method of claim 1, wherein the formulation is administered to the subject parenterally, wherein the formulation comprises a dosage of the carotenoid analog or derivative in the range of about 5 mg to about 1000 mg per day.

9. The method of claim 1, wherein the formulation is administered to the subject parenterally, wherein the formulation comprises a dosage of the carotenoid analog or derivative in the range of about 0.25 mg to about 500 mg per day.

10. The method of claim 1, wherein the formulation is administered as an aqueous preparation.

11. The method of claim 1, wherein the formulation is administered intravenously.

12. The method of claim 1, wherein the formulation is administered intravascularly.

13. The method of claim 1, wherein the formation is administered by intramuscular injection.

14. The method of claim 1, wherein the formulation is administered subcutaneously.

15. The method of claim 1, wherein the formulation is administered transdermally.

16. The method of claim 1, wherein the formulation is administered as an aerosol.

17. The method of claim 1, wherein the carotenoid analog or derivative is administered in the form of an emulsion.

18. The method of claim 17, wherein the emulsion comprises water, oil and lecithin.

19. The method of claim 1, wherein the formulation comprises at least two different carotenoid analogs or derivatives.

20. The method of claim 1, wherein at least one O—C(O)—R group is

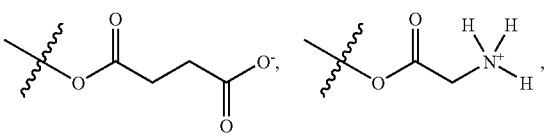

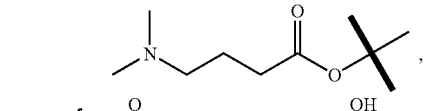

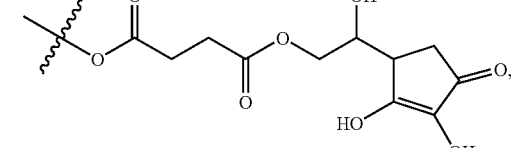

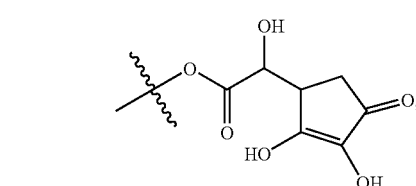

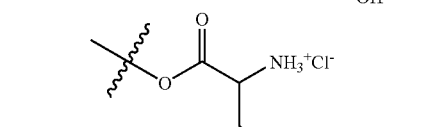

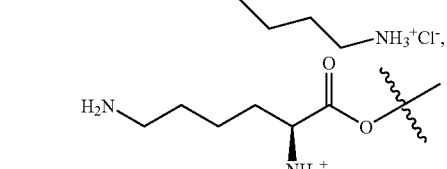

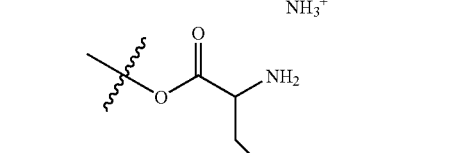

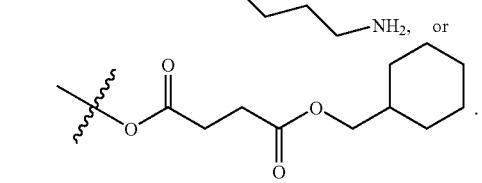

21. The method of claim 1, wherein the carotenoid analog or derivative has the structure

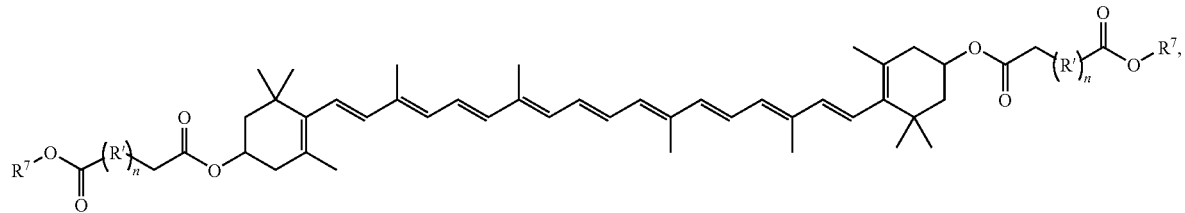

wherein each $R^7$ is independently H, alkyl, aryl, benzyl, or a Group IA metal.

22. The method of claim 1, wherein the carotenoid analog or derivative has the structure

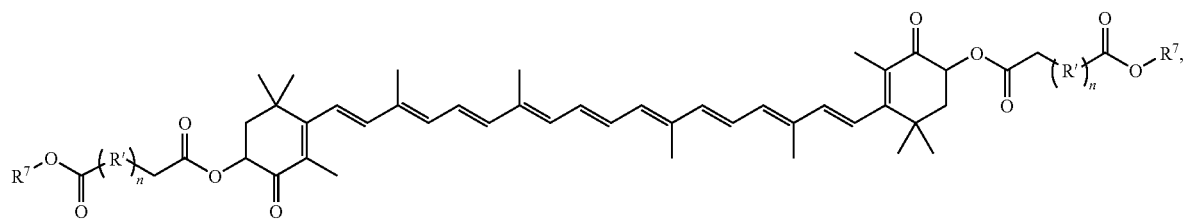

wherein each $R^7$ is independently H, alkyl, aryl, benzyl, or a Group IA metal.

23. The method of claim 1, wherein the carotenoid analog or derivative has the structure

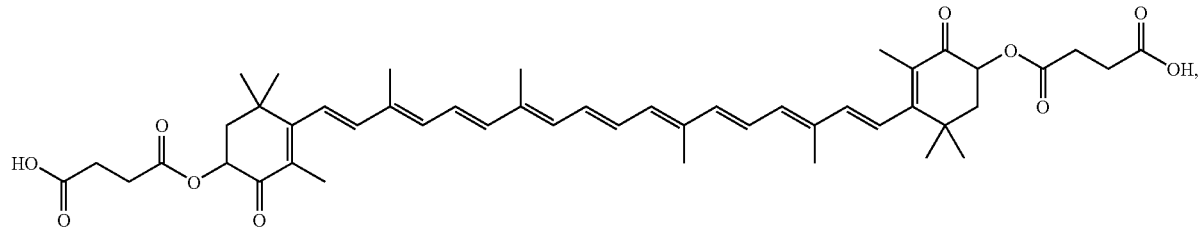

or a pharmaceutically acceptable salt thereof.

24. The method of claim 1, wherein the carotenoid analog or derivative has the structure

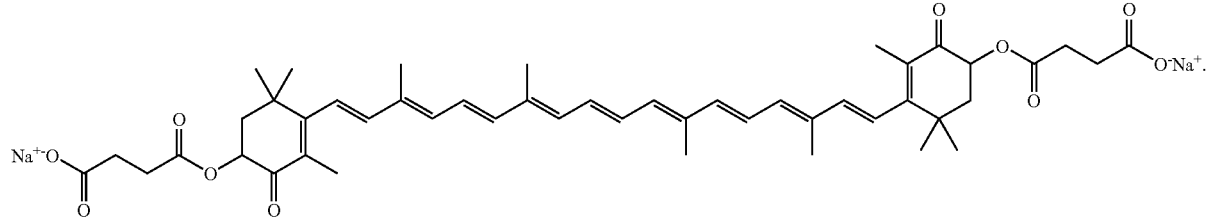

25. The method of claim 1, wherein the carotenoid analog or derivative has the structure

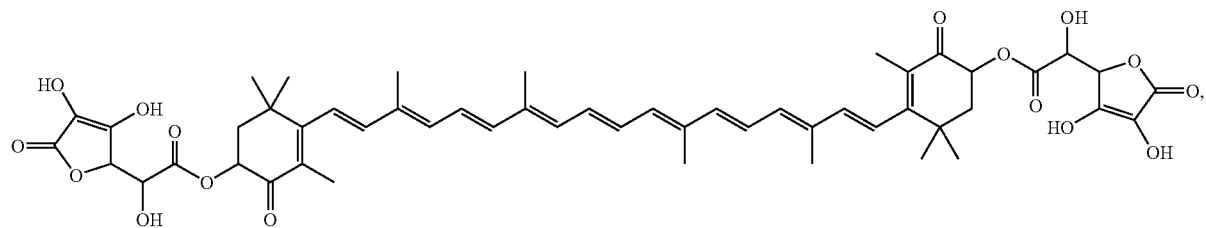

or a pharmaceutically acceptable salt thereof.

26. The method of claim 1, wherein the carotenoid analog or derivative has the structure

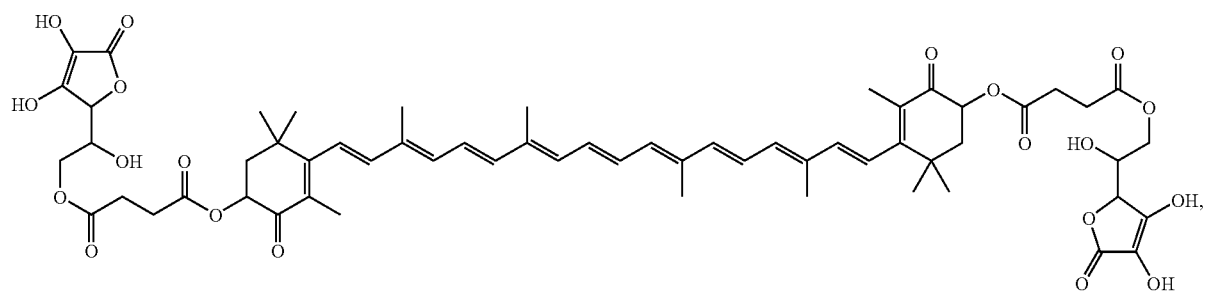

or a pharmaceutically acceptable salt thereof.

27. The method of claim 1, wherein the carotenoid analog or derivative has the structure

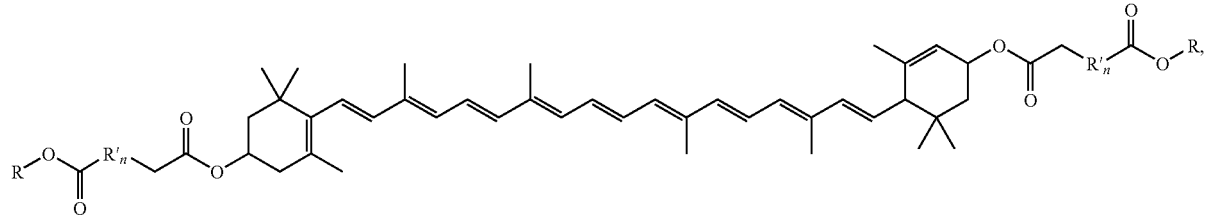

wherein each R is independently H, alkyl, aryl, benzyl, or a Group IA metal.

28. The method of claim 1, wherein the subject is administered a unit oral dose of synthetic carotenoid analog or a carotenoid derivative in the range of about 0.25 mg to about 1.0 g at least once daily.

29. The method of claim 1, wherein the subject is administered a unit oral dose of synthetic carotenoid analog or a carotenoid derivative in the range of about 5 mg to about 25 mg at least once daily.

30. The method of claim 1, wherein the subject is administered a unit parenteral dose of synthetic carotenoid analog or a carotenoid derivative in the range of about 25 mg to about 1.0 g at least once daily.

31. The method of claim 1, wherein the subject is administered a unit parenteral dose of synthetic carotenoid analog or a carotenoid derivative in the range of about 25 mg to about 500 mg at least once daily.

32. The method of claim 1, wherein the formulation is administered to the subject by intrapulmonary administration.

33. The method of claim 1, wherein the formulation is administered by inhalation.

34. The method of claim 1, wherein R is -alkyl-$NR^2_3{}^+$ or -alkyl-$NR^2_2$.

* * * * *